United States Patent
Ohta et al.

(10) Patent No.: US 7,470,717 B2
(45) Date of Patent: *Dec. 30, 2008

(54) INDAZOLE DERIVATIVES

(75) Inventors: Yoshihisa Ohta, Yokohama (JP); Fumihiko Kanai, Sunto-gun (JP); Shinji Nara, Sunto-gun (JP); Yutaka Kanda, Tokyo (JP); Hiroshi Umehara, Sunto-gun (JP); Yukimasa Shiotsu, Sunto-gun (JP); Tomoki Naoe, Nagoya (JP); Hitoshi Kiyoi, Nagoya (JP); Keiko Kawashima, Numazu (JP); Hiromi Ando, Sunto-gun (JP); Motoki Miyama, Sunto-gun (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 526 days.

This patent is subject to a terminal disclaimer.

(21) Appl. No.: 10/548,475

(22) PCT Filed: Jul. 30, 2004

(86) PCT No.: PCT/JP2004/011287

§ 371 (c)(1),
(2), (4) Date: Sep. 12, 2005

(87) PCT Pub. No.: WO2005/012257

PCT Pub. Date: Feb. 10, 2005

(65) Prior Publication Data

US 2007/0117856 A1    May 24, 2007

(30) Foreign Application Priority Data

Jul. 30, 2003    (JP) ............................. 2003-203508

(51) Int. Cl.
*A61K 31/416* (2006.01)
*C07D 231/56* (2006.01)

(52) U.S. Cl. ................. 514/406; 548/356.1; 548/358.1; 548/360.1; 548/361.1; 548/362.5; 514/403; 544/358; 544/359

(58) Field of Classification Search ............. 548/356.1, 548/358.1, 360.1, 361.1, 362.5; 514/403, 514/406; 544/358, 359
See application file for complete search history.

(56) References Cited

U.S. PATENT DOCUMENTS

| | | | |
|---|---|---|---|
| 6,555,539 B2 | 4/2003 | Reich et al. ............. 514/252.02 |
| 6,884,890 B2 * | 4/2005 | Kania et al. ............... 546/275.7 |
| 6,897,231 B2 | 5/2005 | Bhagwat et al. ............. 514/403 |
| 6,919,461 B2 | 7/2005 | Reich et al. ............. 548/362.5 |
| 2002/0091116 A1 | 7/2002 | Zhu et al. ............... 514/211.15 |
| 2002/0103229 A1 | 8/2002 | Bhagwat et al. ............. 514/338 |
| 2002/0161022 A1 | 10/2002 | Reich et al. ................. 514/314 |
| 2003/0139463 A1 | 7/2003 | Reich et al. ................. 514/403 |
| 2004/0077877 A1 | 4/2004 | Bhagwat et al. ............. 548/250 |
| 2004/0107457 A1 | 6/2004 | Kuvshinov et al. .......... 800/278 |
| 2004/0127536 A1 | 7/2004 | Bhagwat et al. ............. 514/406 |
| 2004/0127538 A1 | 7/2004 | Oinuma et al. ............. 514/406 |
| 2005/0009876 A1 | 1/2005 | Bhagwat et al. ............. 514/338 |
| 2005/0208582 A1 | 9/2005 | Ohi et al. ....................... 435/7.1 |
| 2005/0239855 A1 | 10/2005 | Reich et al. ................. 514/394 |
| 2005/0261339 A1 | 11/2005 | Ohi et al. ..................... 514/314 |
| 2005/0282880 A1 | 12/2005 | Oinuma et al. ............. 514/406 |
| 2006/0058366 A1 | 3/2006 | Kanai et al. |

FOREIGN PATENT DOCUMENTS

JP         32059      2/1990
JP    2003-503481    1/2003

OTHER PUBLICATIONS

Chemical Abstracts, vol. 89 (1978), p. 570.

* cited by examiner

*Primary Examiner*—Golam M Shameem
(74) *Attorney, Agent, or Firm*—Fitzpatrick, Cella, Harper & Scinto

(57) ABSTRACT

The present invention provides a compound represented by Formula (I):

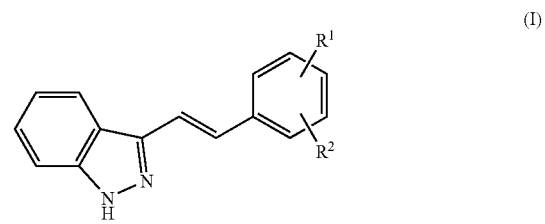

(I)

[wherein $R^1$ represents $CONR^{1a}R^{1b}$ (wherein $R^{1a}$ and $R^{1b}$ may be the same or different and each represents a hydrogen atom, substituted or unsubstituted lower alkyl, substituted or unsubstituted aryl, substituted or unsubstituted ararkyl or a substituted or unsubstituted heterocyclic group, or $R^{1a}$ and $R^{1b}$ are combined together with the adjacent nitrogen atom thereto to form a substituted or unsubstituted heterocyclic group) or the like,
$R^2$ represents a hydrogen atom, $CONR^{2a}R^{2b}$ (wherein $R^{2a}$ and $R^{2b}$ may be the same or different and each represents a hydrogen atom, substituted or unsubstituted lower alkyl, substituted or unsubstituted aryl, substituted or unsubstituted ararkyl or a substituted or unsubstituted heterocyclic group, or $R^{2a}$ and $R^{2b}$ are combined together with the adjacent nitrogen atom thereto to form a substituted or unsubstituted heterocyclic group), $NR^{2c}R^{2d}$ (wherein $R^{2c}$ and $R^{2d}$ may be the same or different and each represents a hydrogen atom, substituted or unsubstituted lower alkyl, substituted or unsubstituted lower alkanoyl, substituted or unsubstituted aroyl, substituted or unsubstituted heteroaroyl, substituted or unsubstituted ararkyl, substituted or unsubstituted lower alkylsulfonyl or substituted or unsubstituted lower arylsulfonyl) or the like].

15 Claims, No Drawings

INDAZOLE DERIVATIVES

TECHNICAL FIELD

The present invention relates to indazole derivatives or pharmaceutically acceptable salts thereof which have antitumor activities or the like.

BACKGROUND ART

As indazole derivatives, various compounds have been known [Japanese Published Unexamined Patent Application (Kokai) No. 32059/1990; WO 01/53268; WO 02/10137; and Khimiya Geterotsiklicheskikh Soedinenii, vol. 7, pages 957-959 (1978)].

In Japanese published Unexamined Patent Application (Kokai) No. 32059/1990, compounds represented by Formula (II)

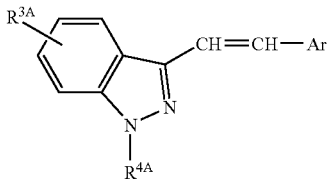

(II)

{wherein $R^{3A}$ represents a hydrogen atom, nitro, $NR^{3A1}R^{3A2}$ [wherein $R^{3A1}$ and $R^{3A2}$ may be the same or different and each represents a hydrogen atom, substituted or unsubstituted lower alkyl (the carbon number in the lower alkyl is 1 to 6), lower alkanoyl (the carbon number in the lower alkanoyl is 1 to 6) or the like] or the like, $R^{4A}$ represents a hydrogen atom or the like, Ar represents pyridyl, substituted or unsubstituted 2-oxochromenyl [the 2-oxochromenyl is bonded to ethenyl (—CH=CH—) on its benzene ring, and the substituent(s) on the 2-oxochromenyl is lower alkyl having 1 to 6 carbon atom(s) or lower alkoxy having 1 to 6 carbon atom(s)], or substituted or unsubstituted phenyl [substituents $Q^{5A1}$, $Q^{5A2}$ and $Q^{5A3}$ in the substituted phenyl may be the same or different and each represents a hydrogen atom, halogen, nitro, nitroso, hydroxy, carboxy, lower alkyl having 1 to 6 carbon atom(s), lower alkoxy having 1 to 6 carbon atom(s), lower alkoxycarbonyl having 1 to 6 carbon atom(s), $NR^{5A1}R^{5A2}$ (wherein $R^{5A1}$ and $R^{5A2}$ have the same meanings as $R^{3A1}$ and $R^{3A2}$ defined above, respectively), or $O(CH_2)_{nd}NR^{5A3}R^{5A4}$ (wherein nd represents an integer of 1 to 6 and $R^{5A3}$ and $R^{5A4}$ have the same meanings as $R^{3A1}$ and $R^{3A2}$ defined above, respectively), or any two from the groups $Q^{5A1}$ to $Q^{5A3}$ are combined together to form —O(CR$^{5A5}$R$^{5A6}$)O— (wherein two terminal oxygen atoms are bonded to the phenyl at adjacent carbon atoms on the phenyl and $R^{5A5}$ and $R^{5A6}$ may be the same or different and each represents a hydrogen atom or lower alkyl having 1 to 6 carbon atom(s), or $R^{5A5}$ and $R^{5A6}$ are combined together to form alkylene having 4 or 5 carbon atoms), provided that the $Q^{5A1}$, $Q^{5A2}$ and $Q^{5A3}$ which are the substituents in the substituted phenyl are not simultaneously hydrogen atoms]} are disclosed.

In WO 01/53268, compounds having suppressive activity on cell differentiation represented by Formula (III)

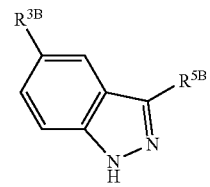

(III)

[wherein $R^{5B}$ represents CH=CH—$R^{5B1}$ (wherein $R^{5B1}$ represents substituted or unsubstituted alkyl, substituted or unsubstituted aryl, a substituted or unsubstituted heterocyclic group or the like) and $R^{3B}$ represents alkyl, aryl, CH=CH—$R^{5B2}$ (wherein $R^{5B2}$ represents substituted or unsubstituted aryl, substituted or unsubstituted heteroaryl or the like)] are disclosed.

In WO 02/10137, compounds having inhibitory activity against c-jun N-terminal Kinase (JNK) represented by Formula (IV)

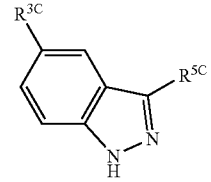

(IV)

[wherein $R^{5C}$ represents CH=CH—$R^{5C1}$ (wherein $R^{5C1}$ represents substituted or unsubstituted aryl, substituted or unsubstituted heteroaryl or the like) and $R^{3C}$ represents halogen, hydroxy, amino or the like] are disclosed.

In Khimiya Geterotsiklicheskikh Soedinenii, vol. 7, pages 957-959 (1978), compounds represented by Formula (V)

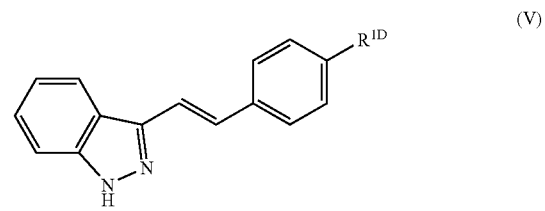

(V)

(wherein $R^{1D}$ represents methoxy or nitro) are disclosed.

DISCLOSURE OF THE INVENTION

An object of the present invention is to provide indazole derivatives or pharmaceutically acceptable salts thereof which are useful as an antitumor agent or the like.

The present invention relates to following (1) to (24).

(1) An indazole derivative represented by Formula (I)

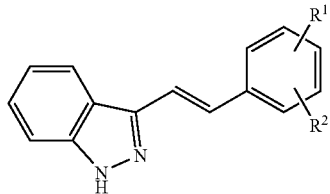

[wherein $R^1$ represents $CONR^{1a}R^{1b}$ (wherein $R^{1a}$ and $R^{1b}$ may be the same or different and each represents a hydrogen atom, substituted or unsubstituted lower alkyl, substituted or unsubstituted aryl, substituted or unsubstituted aralkyl, or a substituted or unsubstituted heterocyclic group, or $R^{1a}$ and $R^{1b}$ are combined together with the adjacent nitrogen atom thereto to form a substituted or unsubstituted heterocyclic group) or $NR^{1c}R^{1d}$ (wherein $R^{1c}$ represents substituted or unsubstituted lower alkylsulfonyl or substituted or unsubstituted arylsulfonyl and $R^{1d}$ represents a hydrogen atom or substituted or unsubstituted lower alkyl) and $R^2$ represents a hydrogen atom, halogen, cyano, nitro, hydroxy, carboxy, lower alkoxycarbonyl, substituted or unsubstituted lower alkyl, substituted or unsubstituted lower alkoxy, substituted or unsubstituted lower alkanoyl, $CONR^{2a}R^{2b}$ (wherein $R^{2a}$ and $R^{2b}$ may be the same or different and each represents a hydrogen atom, substituted or unsubstituted lower alkyl, substituted or unsubstituted aryl, substituted or unsubstituted aralkyl or a substituted or unsubstituted heterocyclic group, or $R^{2a}$ and $R^{2b}$ are combined together with the adjacent nitrogen atom thereto to form a substituted or unsubstituted heterocyclic group) or $NR^{2c}R^{2d}$ (wherein $R^{2c}$ and $R^{2d}$ may be the same or different and each represents a hydrogen atom, substituted or unsubstituted lower alkyl, substituted or unsubstituted lower alkanoyl, substituted or unsubstituted aroyl, substituted or unsubstituted heteroaroyl, substituted or unsubstituted aralkyl, substituted or unsubstituted lower alkylsulfonyl or substituted or unsubstituted arylsulfonyl)], or a pharmaceutically acceptable salt thereof.

(2) The indazole derivative or the pharmaceutically acceptable salt thereof according to (1), wherein $R^1$ is $CONR^{1a}R^{1b}$ (wherein $R^{1a}$ and $R^{1b}$ have the same meanings as defined above, respectively) and $R^2$ is a hydrogen atom or substituted or unsubstituted lower alkoxy.

(3) The indazole derivative or the pharmaceutically acceptable salt thereof according to (1), wherein $R^1$ is $NR^{1c}R^{1d}$ (wherein $R^{1c}$ and $R^{1d}$ have the same meanings as defined above, respectively) and $R^2$ is substituted or unsubstituted lower alkoxy.

(4) The indazole derivative or the pharmaceutically acceptable salt thereof according to (1), wherein $R^1$ is $CONR^{1a}R^{1b}$ (wherein $R^{1a}$ and $R^{1b}$ have the same meanings as defined above, respectively) and $R^2$ is halogen or substituted or unsubstituted lower alkyl.

(5) The indazole derivative or the pharmaceutically acceptable salt thereof according to (1), wherein $R^1$ is $NR^{1c}R^{1d}$ (wherein $R^{1c}$ and $R^{1d}$ have the same meanings as defined above, respectively) and $R^2$ is a hydrogen atom.

(6) A pharmaceutical composition which comprises, as an active ingredient, the indazole derivative or the pharmaceutically acceptable salt thereof according to any of (1) to (5).

(7) An antitumor agent which comprises, as an active ingredient, the indazole derivative or the pharmaceutically acceptable salt thereof according to any of (1) to (5).

(8) A therapeutic agent for hematopoietic tumor which comprises, as an active ingredient, the indazole derivative or the pharmaceutically acceptable salt thereof according to any of (1) to (5).

(9) A therapeutic agent for leukemia which comprises, as an active ingredient, the indazole derivative or the pharmaceutically acceptable salt thereof according to any of (1) to (5).

(10) A therapeutic agent for myeloma or lymphoma which comprises, as an active ingredient, the indazole derivative or the pharmaceutically acceptable salt thereof according to any of (1) to (5).

(11) A therapeutic agent for solid carcinoma which comprises, as an active ingredient, the indazole derivative or the pharmaceutically acceptable salt thereof according to any of (1) to (5).

(12) A therapeutic agent for cancer derived from mammary cancer, uterine body cancer, uterine cervix cancer, prostatic cancer, bladder cancer, renal cancer, gastric cancer, esophageal cancer, hepatic cancer, biliary tract cancer, colon cancer, rectal cancer, pancreatic cancer, lung cancer, oral cavity and pharynx cancer, osteosarcoma, melanoma or brain neoplasm, which comprises, as an active ingredient, the indazole derivative or the pharmaceutically acceptable salt thereof according to any of (1) to (5).

(13) Use of the indazole derivative or the pharmaceutically acceptable salt thereof according to any of (1) to (5) for the manufacture of an antitumor agent.

(14) Use of the indazole derivative or the pharmaceutically acceptable salt thereof according to any of (1) to (5) for the manufacture of a therapeutic agent for hematopoietic tumor.

(15) Use of the indazole derivative or the pharmaceutically acceptable salt thereof according to any of (1) to (5) for the manufacture of a therapeutic agent for leukemia.

(16) Use of the indazole derivative or the pharmaceutically acceptable salt thereof according to any of (1) to (5) for the manufacture of a therapeutic agent for myeloma or lymphoma.

(17) Use of the indazole derivative or the pharmaceutically acceptable salt thereof according to any of (1) to (5) for the manufacture of a therapeutic agent for solid carcinoma.

(18) Use of the indazole derivative or the pharmaceutically acceptable salt thereof according to any of (1) to (5) for the manufacture of a therapeutic agent for cancer derived from mammary cancer, uterine body cancer, uterine cervix cancer, prostatic cancer, bladder cancer, renal cancer, gastric cancer, esophageal cancer, hepatic cancer, biliary tract cancer, colon cancer, rectal cancer, pancreatic cancer, lung cancer, oral cavity and pharynx cancer, osteosarcoma, melanoma or brain neoplasm.

(19) A method for treating tumor, comprising a step of administering an effective amount of the indazole derivative or the pharmaceutically acceptable salt thereof according to any of (1) to (5).

(20) A method for treating hematopoietic tumor, comprising a step of administering an effective amount of the indazole derivative or the pharmaceutically acceptable salt thereof according to any of (1) to (5).

(21) A method for treating leukaemia, comprising a step of administering an effective amount of the indazole derivative or the pharmaceutically acceptable salt thereof according to any of (1) to (5).

(22) A method for treating myeloma or lymphoma, comprising a step of administering an effective amount of the indazole derivative or the pharmaceutically acceptable salt thereof according to any of (1) to (5).

(23) A method for treating solid carcinoma, comprising a step of administering an effective amount of the indazole derivative or the pharmaceutically acceptable salt thereof according to any of (1) to (5).

(24) A method for treating cancer derived from mammary cancer, uterine body cancer, uterine cervix cancer, prostatic cancer, bladder cancer, renal cancer, gastric cancer, esophageal cancer, hepatic cancer, biliary tract cancer, colon cancer, rectal cancer, pancreatic cancer, lung cancer, oral cavity and pharynx cancer, osteosarcoma, melanoma or brain neoplasm, comprising a step of administering an effective amount of the indazole derivative or the pharmaceutically acceptable salt thereof according to any of (1) to (5).

The compounds represented by General Formula (I) are hereinafter referred to as Compound (I). The same is true for compounds represented by other formula number.

In the definitions for each groups in Formula (I):

(i) The halogen includes fluorine, chlorine, bromine, and iodine atoms.

(ii) Examples of the lower alkyl and the lower alkyl moieties of the lower alkoxy, the lower alkoxycarbonyl and the lower alkylsulfonyl include, for example, linear, branched or cyclic alkyl or alkyl comprising these alkyls in combination, having 1 to 10 carbon atom(s). More specific examples thereof are as follows.

(ii-a) Examples of the linear or branched lower alkyl include, for example, methyl, ethyl, n-propyl, isopropyl, n-butyl, isobutyl, se c-butyl, tert-butyl, n-pentyl, neopentyl, n-hexyl, n-heptyl, n-octyl, n-nonyl and n-decyl;

(ii-b) examples of the cyclic lower alkyl include, for example, cyclopropyl, cyclobutyl, cyclopentyl, cyclohexyl, cycloheptyl, cyclooctyl, cyclodecyl, noradamantyl, adamantyl, bicyclo[2.2.1]heptyl, bicyclo[2.2.2]octyl, bicyclo[3.3.0]octyl and bicyclo[3.3.1]nonyl; and (ii-c) examples of the lower alkyl comprising linear or branched alkyl and cyclic alkyl include, for example, cyclopropylmethyl, cyclopentylmethyl and cyclooctylethyl.

(iii) The alkylene moiety of the aralkyl has the same meaning as the group formed by removing one hydrogen atom from the linear or branched lower alkyl (ii-a) in the definition of the lower alkyl defined above.

(iv) Examples of the aryl and the aryl moieties of the aroyl, the arylsulfonyl and the aralkyl include, for example, monocyclic aryls or fused aryl in which two or more rings are fused, and more specific examples include aryl having 6 to 14 carbon atoms as ring-constituting members, such as phenyl, naphthyl, indenyl or anthranyl.

(v) Examples of the lower alkanoyl include, for example, linear, branched, or cyclic lower alkanyol, or lower alkanoyl comprising these lower alkanoyls in combination, having 1 to 8 carbon atom(s), such as formyl, acetyl, propionyl, butyryl, isobutyryl, valeryl, isovaleryl, pivaloyl, hexanoyl, heptanoyl, octanoyl, cyclopropylcarbonyl, cyclobutylcarbonyl, cyclopropylmethylcarbonyl, cyclopentylcarbonyl, cyclohexylcarbonyl, 1-methylcyclopropylcarbonyl or cycloheptylcarbonyl.

(vi) Examples of the heterocyclic group include, for example, heteroaromatic group and heteroalicyclic group. Examples of the heteroaromatic group include, for example, monocyclic aromatic heterocyclic group or fused heteroaromatic group in which two or more rings are fused. The type and number of the heteroatom contained in heteroaromatic group are not specifically limited and the heteroaromatic group may contain, for example, one or more heteroatoms selected from the group consisting of nitrogen atom, sulfur atom and oxygen atom. More specific examples include heteroaromatic group having 5 to 14 carbon atoms as ring-constituting members, such as furyl, thienyl, pyrrolyl, imidazolyl, pyrazolyl, triazolyl, tetrazolyl, oxazolyl, oxadiazolyl, thiazolyl, pyridyl, pyrazinyl, pyrimidinyl, pyridazinyl, triazinyl, indolyl, indazolyl, benzimidazolyl, benzoxazolyl, benzothiazolyl, quinolyl, isoquinolyl, phthalazinyl, naphthyridinyl, quinoxalinyl, quinazolinyl, cinnolinyl, purinyl or coumarinyl. Examples of the heteroalicyclic group include, for example, monocyclic heteroalicyclic group or fused heteroalicyclic group in which two or more rings are fused. The type and number of the heteroatom contained in heteroalicyclic groups are not specifically limited and the heteroalicyclic group may contain, for example, one or more heteroatoms selected from the group consisting of nitrogen atom, sulfur atom and oxygen atom. More specific examples include, for example, pyrrolidinyl, thiazolidinyl, oxazolidinyl, piperidyl, 1,2-dihydropyridyl, piperazinyl, homopiperazinyl, morpholinyl, thiomorpholinyl, pyrazolinyl, oxazolinyl, dioxolanyl, tetrahydropyranyl, tetrahydrothiopyranyl, tetrahydrofuryl, tetrahydroquinolyl, tetrahydroisoquinolyl, tetrahydroquinoxalinyll octahydroquinolyl, indolinyl and isoindolinyl.

(vii) Examples of the heterocyclic group formed together with the adjacent nitrogen atom include 5- or 6-membered monocyclic heteroalicyclic group containing at least one nitrogen atom (the monocyclic heteroalicyclic group may further contain any other of a nitrogen atom, an oxygen atom and a sulfur atom) and bicyclic or tricyclic fused heterocyclic group containing at least one nitrogen atom in which 3- to 8-membered rings are fused (the fused heterocyclic group may further contain any other of a nitrogen atom, an oxygen atom and a sulfur atom). More specific examples include, for example, pyrrolidinyl, pyrrolidonyl, piperidino, piperazinyl, morpholino, thiomorpholino, homopiperidino, homopiperazinyl, tetrahydropyridyl, tetrahydroquinolyl, tetrahydroisoquinolyl, indolyl and isoindolyl.

(viii) The heteroaryl moiety in the heteroaroyl has the same meaning as the heteroaromatic group in the heterocyclic group (vi) defined above.

(ix) Examples of the substituents in the substituted lower alkyl, the substituted lower alkoxy, the substituted lower alkylsulfonyl and the substituted lower alkanoyl, which may be the same or different and in number of 1 to 3, include (ix-a) hydroxy, (ix-b) oxo, (ix-c) carboxy, (ix-d) lower alkoxy, (ix-e) lower alkoxycarbonyl, (ix-f) arylsulfonyl, (ix-g) heteroaroyl, (ix-h) substituted or unsubstituted aryl (the substituent(s) in the substituted aryl, which is 1 to 3 in number, is for example, carboxy, lower alkoxycarbonyl, methylenedioxy and ethylenedioxy), (ix-i) a substituted or unsubstituted heterocyclic group [the substituent(s) (ix-ia) in the substituted heterocyclic group, which is 1 to 3 in number, is for example, lower alkyl, lower alkoxy and lower alkanoyl, and when the substituted heterocyclic group is a substituted heteroalicyclic group, the substituent may be oxo], (ix-j) $NR^{6a}R^{6b}$ [wherein $R^{6a}$ and $R^{6b}$ may be the same or different and each represents a hydrogen atom, substituted or unsubstituted lower alkyl (the substituent(s) in the substituted lower alkyl, which is 1 to 3 in number, is for example, halogen, hydroxy or lower alkoxy) or substituted or unsubstituted lower alkanoyl (the substituent(s) in the substituted lower alkanoyl, which is 1 to 3 in number, is for example, halogen, hydroxy, lower alkoxy or aryl) or $R^{6a}$ and $R^{6b}$ are combined together with the adjacent nitrogen atom thereto to form a heterocyclic group], (ix-k) $CONR^{7a}R^{7b}$ (wherein $R^{7a}$ and $R^{7b}$ have the same meanings as $R^{6a}$ and $R^{6b}$ defined above, respectively) and (ix-l) lower alkoxy-lower alkoxy.

In the definition of the substituents (ix) in the substituted lower alkyl, the substituted lower alkoxy, the substituted lower alkylsulfonyl and the substituted lower alkanoyl, the halogen has the same meaning as (i) defined above; the lower alkyl and the lower alkyl moiety of the lower alkoxy, the lower alkoxycarbonyl and the lower alkoxy-lower alkoxy have the same meanings as (ii) defined above, respectively; the alkylene moiety of the lower alkoxy-lower alkoxy has the same meaning as the group formed by removing one hydrogen atom from the linear or branched lower alkyl (ii-a) in the definition of the lower alkyl defined above; the aryl and the aryl moiety of the arylsulfonyl have the same meanings as (iv) defined above, respectively; the lower alkanoyl has the same meaning as (v) defined above; the heterocyclic group has the same meaning as (vi) defined above; the heterocyclic group formed together with the adjacent nitrogen atom has the same meaning as (vii) defined above; and the heteroaroyl has the same meaning (viii) defined above.

(x) Examples of the substituents in the substituted aryl, the substituted ardyl, the substituted aralkyl, the substituted arylsulfonyl, the substituted heteroaroyl, the substituted heterocyclic group and the substituted heterocyclic group formed together with the adjacent nitrogen atom, which may be the same or different and is 1 to 3 in number, include (x-a) halogen,
(x-b) hydroxy,
(x-c) nitro,
(x-d) cyano,
(x-e) formyl,
(x-f) carboxy,
(x-g) lower alkoxycarbonyl,
(x-h) substituted or unsubstituted lower alkyl [the substituent(s) in the substituted lower alkyl has the same meaning as (ix) defined above],
(x-i) substituted or unsubstituted lower alkoxy [the substituent(s) in the substituted lower alkoxy has the same meaning as (ix) defined above],
(x-j) substituted or unsubstituted lower alkanoyl [the substituent(s) in the substituted lower alkanoyl has the same meaning as (ix) defined above],
(x-k) substituted or unsubstituted lower alkylsulfonyl [the substituent(s) in the substituted lower alkylsulfonyl has the same meaning as (ix) defined above],
(x-l) substituted or unsubstituted aroyl [the substituent(s) (x-la) in the substituted aroyl, which is 1 to 3 in number, is for example, halogen, hydroxy, nitro, cyano, carboxy, lower alkanoyl, lower alkoxycarbonyl, aralkyl, aroyl, substituted or unsubstituted lower alkyl (the substituent(s) in the substituted lower alkyl, which is 1 to 3 in number, is for example hydroxy) and substituted or unsubstituted lower alkoxy (the substituent(s) in the substituted lower alkoxy, which is 1 to 3 in number, is for example hydroxy),
(x-m) substituted or unsubstituted heteroaroyl [the substituent(s) in the substituted heteroaroyl has the same meaning as (x-la) defined above],
(x-n) substituted or unsubstituted aryl [the substituent(s) in the substituted aryl has the same meaning as (x-la) defined above], (x-o) a substituted or unsubstituted heterocyclic group [the substituent(s) in the substituted heterocyclic group has the same meaning as (ix-ia) defined above], (x-p) $NR^{8a}R^{8b}$ (wherein $R^{8a}$ and $R^{8b}$ may be the same or different and each represents a hydrogen atom, mono- or di-(lower alkyl)aminocarbonyl, substituted or unsubstituted lower alkyl [the substituent(s) in the substituted lower alkyl has the same meaning as (ix) defined above], substituted or unsubstituted lower alkanoyl [the substituent(s) in the substituted lower alkanoyl has the same meaning as (ix) defined above], substituted or unsubstituted lower alkoxycarbonyl [the substituent(s) in the substituted lower alkoxycarbonyl has the same meaning as (ix) defined above], substituted or unsubstituted aryl [the substituent(s) in the substituted aryl has the same meaning as (x-la) defined above], substituted or unsubstituted aroyl [the substituent(s) in the substituted aroyl has the same meaning as (x-la) defined above] or substituted or unsubstituted heteroalicyclic carbonyl [the substituent(s) in the substituted heteroalicyclic carbonyl, which is 1 to 3 in number, is for example, halogen, hydroxy, oxo, amino, nitro, cyano, carboxy, lower alkanoyl, lower alkoxycarbonyl, aralkyl, aroyl, substituted or unsubstituted lower alkyl (wherein the substituent(s) in the substituted lower alkyl, which is 1 to 3 in number, is for example hydroxy), substituted or unsubstituted lower alkoxy (the substituent(s) in the substituted lower alkoxy, which is 1 to 3 in number, is for example hydroxy)] or $R^{8a}$ and $R^{8b}$ are combined together with the adjacent nitrogen atom thereto to form a substituted or unsubstituted heterocyclic group [the substituent(s) in the substituted heterocyclic group formed with the adjacent nitrogen atom, which is 1 to 3 in number, is for example, halogen, hydroxy, oxo, amino, nitro, cyano, carboxy, lower alkanoyl, lower alkoxycarbonyl, aralkyl, aroyl, substituted or unsubstituted lower alkyl (the substituent(s) in the substituted lower alkyl, which is 1 to 3 in number, is for example hydroxy) or substituted or unsubstituted lower alkoxy (the substituent(s) in the substituted lower alkoxy, which is 1 to 3 in number, is for example hydroxy)]}, (x-q) $CONR^{9a}R^{9b}$ (wherein $R^{9a}$ and $R^{9b}$ have the same meanings as $R^{8a}$ and $R^{8b}$ defined above, respectively), (x-r) substituted or unsubstituted arylsulfonyl [the substituent(s) in the substituted arylsulfonyl has the same meaning as (x-la) defined above], (x-s) substituted or unsubstituted lower cycloalkenyl {the substituent(s) in the substituted lower cycloalkenyl, which is 1 to 3 in number, is for example, amino, oxo, mono- or di-(lower alkyl)amino, or a substituted or unsubstituted heterocyclic group [the substituent(s) in the substituted heterocyclic group has the same meaning as (x-la) defined above]} and (x-t) substituted or unsubstituted heteroalicyclic carbonyl [the substituent(s) in the substituted heteroalicyclic carbonyl, which is 1 to 3 in number, is for example, halogen, hydroxy, oxo, amino, nitro, cyano, carboxy, lower alkanoyl, lower alkoxycarbonyl, aralkyl, aroyl, substituted or unsubstituted lower alkyl (the substituent(s) in the substituted lower alkyl, which is 1 to 3 in number, is for example hydroxy) or a substituted or unsubstituted lower alkoxy (the substituent(s) in the substituted lower alkoxy, which is 1 to 3 in number, is for example hydroxy)].

The substituent(s) in the substituted heteroalicyclic group, and the substituent(s) in the substituted heterocyclic group formed with the adjacent nitrogen atom may be, in addition to (x-a) to (x-t), the following (x-u) or (x-v):

(x-u) oxo
(x-v) $-O(CR^{10a}R^{10b})_nO-$ (wherein $R^{10a}$ and $R^{10b}$ may be the same or different and each represents a hydrogen atom, lower alkyl or the like, n represents 2 or 3, and the two terminal oxygen atoms are combined on the same carbon atom in the substituted heterocyclic group formed with the adjacent nitrogen atom)

In the definition of the substituents (x) in the substituted aryl, the substituted aroyl, the substituted aralkyl, the substituted arylsulfonyl, the substituted heteroaroyl, the substituted heterocyclic group and the substituted heterocyclic group formed with the adjacent nitrogen atom, the halogen has the same meaning as (i) defined above; the lower alkyl and the lower alkyl moiety in the lower alkoxy, the lower alkoxycarbonyl, the lower alkylsulfonyl, the mono- or di-(lower alkyl)amino and the mono- or di-(lower alkyl)aminocarbonyl have the same meanings as (ii) defined above, respectively, and the two lower alkyl moieties in the di-(lower alkyl)amino and the di-(lower alkyl)aminocarbonyl may be the same or different; the alkylene moiety in the aralkyl has the same meaning as (iii) defined above; the aryl and the aryl moiety in the aralkyl, the aroyl and the arylsulfonyl have the same meanings as (iv) defined above, respectively; the lower alkanoyl has the same meaning as (v) defined above; the heterocyclic group has the same meaning as (vi) defined above; the heterocyclic group formed with the adjacent nitrogen atom has the same meaning as (vii) defined above; the heteroaryl moiety in the heteroaroyl has the same meaning as (viii) defined above; and the heteroalicyclic moiety in the heteroalicyclic carbonyl has the same meaning as the heteroalicyclic group in the heterocyclic group (vi) defined above. Examples of the lower cycloalkenyl include, for example, cycloalkenyl having 4 to 8 carbon atoms, such as cyclobutenyl, cyclopentenyl, cyclohexenyl, cycloheptenyl, and cyclooctenyl.

Examples of the pharmaceutically acceptable salts of Compound (I) include, for example, pharmaceutically acceptable acid addition salts, metal salts, ammonium salts, organic amine addition salts, and amino acid addition salts. The acid addition salts include, for example, inorganic acid salts such as hydrochlorides, sulfates and phosphates; and organic acid salts such as acetate, maleate, fumarate, tartrates, citrates, lactates, aspartates, and glutamates. The metal salts include, for example, alkali metal salts such as sodium salts and potassium salts; alkaline earth metal salts such as magnesium salts and calcium salts; as well as aluminum salts and zinc salts. The ammonium salts include, for example, salts of ammonium and tetramethylammonium. The organic amine addition salts include, for example, morpholine salts and piperidine salts. The amino acid addition salts include, for example, lysine salts, glycine salts and phenylalanine salts.

The hematopoietic tumor refers to tumors typically in hemocytes. Examples of pathosis based on the hematopoietic tumor are leukemia such as chronic myeloid leukemia and acute myeloid leukemia; myeloma such as multiple myeloma; and lymphoma.

Production methods of Compound (I) will be described below.

Me, Et, Pr, $^i$Pr, $^i$Bu, $^t$Bu, and Ph in the following reaction processes, structural formulae and tables represent methyl, ethyl, propyl, isopropyl, isobutyl, tert-butyl, and phenyl, respectively. The definitions of each groups in the following reaction processes have the same meanings as each groups defined above, unless otherwise noted.

When a defined group changes under the reaction conditions or is not suitable for carrying out the method in the following production methods, it is possible to obtain the targeted compound using a method for introduction and elimination of protective group commonly used in synthetic organic chemistry [for example, Protective Groups in Organic Synthesis, third edition, T. W. Greene, John Wiley & Sons Inc. (1999)]. If necessary, the order of reaction processes such as introduction of substituents can be changed.

Compound (I) can be produced according to the following reaction processes.

Production Method 1

Compound (I) can be produced using Compound (A) obtained in a similar manner to the known method [e.g., J. Org. Chem., vol. 52, page 19 (1987); Can. J. Chem., vol. 51, page 792 (1973)] according to the following process:

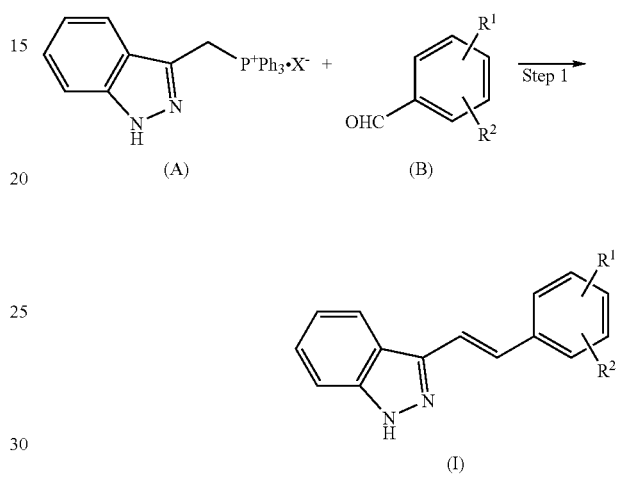

(wherein X represents each atoms of chlorine, bromine or iodine and $R^1$ and $R^2$ have the same meanings as defined above, respectively)

Step 1

Compound (I) can be obtained by reacting Compound (A) with Compound (B) in the presence of a base, in a solvent such as methanol, ethanol, tetrahydrofuran (THF), N,N-dimethylformamide (DMF), and mixtures of these solvents.

Potassium carbonate, potassium tert-butoxide, and sodium hydride may be used as the base. To Compound (A), 1 to 10 equivalent(s) of Compound (B) and the base are used, respectively. The reaction is usually performed at temperatures between 0 and 100° C. for 1 to 72 hours.

Production Method 2

Among Compound (I), Compound (Ia) which have a specific functional group in $R^1$ or $R^2$ may also be produced using Compound (C) which have other functional group in $R^1$ or $R^2$ obtained according to Production Method 1 or other known method (for example, Japanese Published Unexamined Patent Application (kokai) No. 32059/1990) according to the following process.

Although all the compounds mentioned as Compound (Ia) and the like in the following steps, are not always included in the scope of Compound (I), they are indicated as, for example, Compound (Ia) for the sake of convenience. Further, even among compounds called here Compound (C) in the following Steps 2-1 to 2-5, there are compounds included in Compound (I).

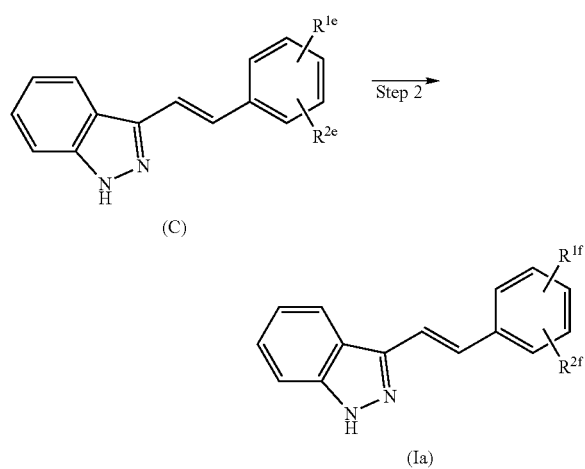

(wherein $R^{1e}$, $R^{1f}$, $R^{2e}$ and $R^{2f}$ represent the groups defined in following Steps 2-1 to 2-5, respectively. $R^{1e}$ and $R^{1f}$ have the same meanings as $R^1$ defined above, respectively and $R^{2e}$ and $R^{2f}$ have the same meaning as $R^2$ defined above, respectively, unless otherwise defined in following Steps 2-1 to 2-5)

Step 2-1

(In Step 2-1, at least one of $R^{1e}$ and $R^{2e}$ is lower alkoxycarbonyl and at least one of $R^{1f}$ and $R^{2f}$ is carboxy)

Compound (Ia) can be obtained by subjecting Compound (C) to hydrolysis in water or in a mixed solvent of water and another solvent such as methanol, ethanol or THF, in the presence of a base such as sodium hydroxide or an acid such as hydrochloric acid.

To Compound (C), 0.1 to 10 equivalent(s) of the acid or the base is preferably used. The reaction is usually performed at temperatures between 20 and 100° C. for 1 to 72 hour(s).

Step 2-2

(In Step 2-2, at least one of $R^{1e}$ and $R^{2e}$ is nitro and at least one of $R^{1f}$ and $R^{2f}$ is amino)

Compound (Ia) can be obtained by treating Compound (C) with a reducing agent such as tin or iron in the presence of an acid such as concentrated hydrochloric acid or acetic acid in a solvent such as water, ethanol or a mixed solvent thereof, or in the absence of the solvent, or by subjecting Compound (C) to reduction in the presence of a catalyst such as palladium/carbon, platinum dioxide or Raney nickel in an atmosphere of hydrogen gas or in the presence of a hydrogen donor such as hydrazine hydrate or ammonium formate in a solvent such as water, methanol, ethanol, THF, DMF, or a mixed solvent thereof.

To Compound (C), 1 to 100 equivalent(s) of the acid such as concentrated hydrochloric acid or acetic acid and 1 to 20 equivalent(s) of the reducing agent such as tin or iron are preferably used. To Compound (C), 0.5 to 100 weight % of the catalyst and 1 to 100 equivalent(s) of the hydrogen donor are preferably used. The reaction is usually performed at temperatures between 0 to 100° C. for 1 to 72 hours.

Step 2-3

[In the Step 2-3, at least one of $R^{1e}$ and $R^{2e}$ is carboxy and at least one of $R^{1f}$ and $R^{2f}$ is $CONR^{10}OR^{11}$ (wherein $R^{10}$ and $R^{11}$ have the same meanings as $R^{1a}$ and $R^{1b}$ defined above, respectively)]

Compound (Ia) can be obtained by reacting Compound (C) with Compound (V) represented by $HNR^{10}R^{11}$ (wherein $R^{10}$ and $R^{11}$ have the same meanings as defined above, respectively) in the presence of a condensing agent and an activating agent, in a solvent such as dichloromethane, THF, 1,4-dioxane, DMF or N-methylpiperidone or a mixed solvent thereof. Examples of the condensing agent include dicyclohexylcarbodiimide, 1-ethyl-3-(3-dimethylaminopropyl)carbodiimide hydrochloride, polymer-bound 1-ethyl-3-(3-dimethylaminopropyl)carbodiimide, and triphenylphosphine oxide.trifluoromethanesulfonic anhydride. Examples of the activating agent include 1-hydroxybenzotriazole and N-hydroxysuccinimide.

To Compound (C), 1 to 20 equivalent(s) of the reducing agent, the activating agent and Compound (V) are preferably used, respectively. The reaction is usually performed at temperatures between −20 and 80° C. for 30 minutes to 72 hours. Some of Compound (V) can be subjected to the reaction in the form of a salt formed by mixing with an activating agent.

Step 2-4

[In the Step 2-4, at least one of $R^{1e}$ and $R^{2e}$ is amino and at least one of $R^{1f}$ and $R^{2f}$ is $NHSO_2R^{12}$ (wherein $R^{12}$ represents substituted or unsubstituted lower alkyl or substituted or unsubstituted aryl)]

In the definition of $R^{12}$, the lower alkyl and the aryl have the same meanings as (ii) and (iv) defined above, respectively. The substituents in the substituted lower alkyl and the substituted aryl have the same meanings as (ix) and (x) defined above, respectively.

Compound (Ia) can be obtained by reacting Compound (C) with Compound (VI) represented by $R^{12}SO_2Cl$ (wherein $R^{12}$ has the same meaning as defined above) or Compound (VII) represented by $(R^{12}SO_2)_2O$ (wherein $R^{12}$ has the same meaning as defined above) in the presence of a base such as triethylamine, pyridine, p-dimethylaminopyridine, polyvinylpyridine, 4-morpholinomethylpolystyrene or 4-piperidinopolystyrene, in a solvent such as dichloromethane, THF, 1,4-dioxane, DMF, or N-methylpiperidone or a mixed solvent thereof.

To Compound (C), 1 to 20 equivalent(s) of the base and the Compound (VI) or Compound (VII) are preferably used, respectively. The reaction is usually performed at temperatures between −20 and 80° C. for 30 minutes to 24 hours.

Step 2-5

[In the Step 2-5, at least one of $R^{1e}$ and $R^{2e}$ is substituent including halogen and at least one of $R^{1f}$ and $R^{2f}$ is substituent including carboxy. The halogen has the same meaning as (i) defined above]

Compound (Ia) can be obtained by treating Compound (C) with a strong base such as sodium hydride or n-butyllithium in a solvent such as THF, and reacting the obtained compound with gaseous or solid carbon dioxide.

To Compound (C), 1 to 10 equivalent(s) of the strong base and 1 to 200 equivalent(s) of carbon dioxide are preferably used, respectively. The reaction is usually performed at temperatures between −80 and 30° C. for 1 to 24 hours.

Transformation of functional groups contained in $R^1$ or $R^2$ in Compound (I) and the starting material can also be carried out by other known methods [for example, Comprehensive Organic Transformations, R. C. Larock, (1989)] in addition to the above processes.

Compound (I) having a desired functional group at a desired position can be obtained by carrying out the above processes in any suitable combination thereof.

Isolation and purification of the Products in the above-mentioned production methods can be carried out by an appropriate combination of usual methods used in organic syntheses, such as filtration, extraction, washing, drying, concentration, crystallization and various chromatography. Intermediates can also be use in the subsequent reaction step without further purification.

There can be isomers such as positional isomers, geometrical isomers or optical isomers in Compound (I). All possible isomers including these isomers, and mixtures of the isomers in any ratio can be used in the present invention or included in the present invention.

When it is desired to obtain a salt of Compound (I), in the case where it is obtained in a form of a salt, this may be purified as it is, where it is obtained in a free form, it is dissolved or suspended in an appropriate solvent followed by adding an acid or a base thereto to form a salt.

Compound (I) or pharmaceutically acceptable salt thereof may exist in the form of adducts with water or solvents. These adducts are also included in the present invention.

Specific examples of Compound (I) are shown in Table 1 which by no means limit the scope of the present invention.

TABLE 1

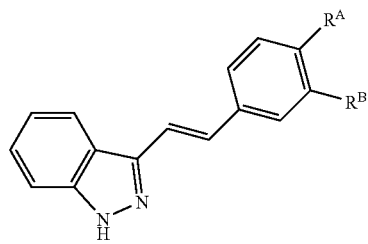

| Compound Number | $R^A$ | $R^B$ | salt |
|---|---|---|---|
| 1 | CONMe$_2$ | H | |
| 2 | CONHCH$_2$CH$_2$CHMe$_2$ | H | |
| 3 | CONHCH$_2$Ph | H | |
| 4 | CONHCH$_2$CH$_2$OMe | H | |
| 5 | CONMeCH$_2$CH$_2$OMe | H | |
| 6 | CONHCH$_2$CH$_2$NMe$_2$ | H | |
| 7 | OCH$_2$CH$_2$N(morpholine) | NHSO$_2$Me | |
| 8 | OCH$_2$CH$_2$N(morpholine) | CONH$_2$ | |
| 9 | CON(morpholine) | H | |
| 10 | CONHCH$_2$CH$_2$N(morpholine) | H | |
| 11 | CONH(CH$_2$)$_2$NHCOMe | H | |
| 12 | OCH$_2$CH$_2$N(morpholine) | CONHMe | |
| 13 | CON(piperazine-NCOMe) | H | |
| 14 | CONHMe | H | |
| 15 | CONEt$_2$ | H | HCl |
| 16 | CON(1,4-dioxa-8-azaspiro[4.5]decane) | H | HCl |

TABLE 1-continued
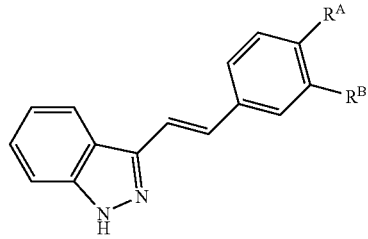
| Compound Number | R^A | R^B | salt |
|---|---|---|---|
| 17 | 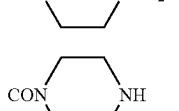 | H | |
| 18 | 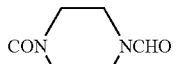 | H | |
| 19 | 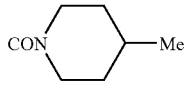 | H | |
| 20 | 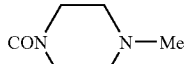 | H | |
| 21 | 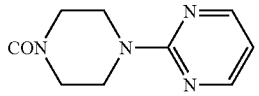 | H | |
| 22 | 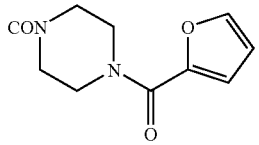 | H | |
| 23 | 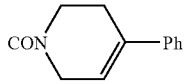 | H | |
| 24 | 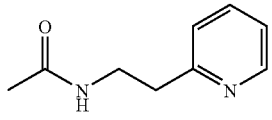 | H | |
| 25 | 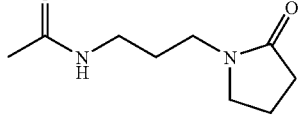 | H | |
| 26 | 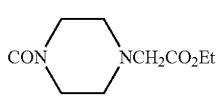 | H | HCl |
| 27 | H | NHSO$_2$Me | |
| 28 | H | NHSO$_2$Ph | HCl |
| 29 |  | H | |

TABLE 1-continued

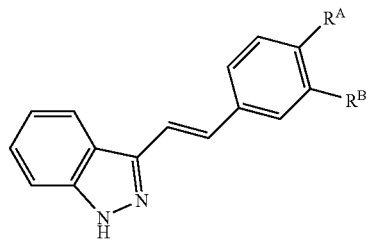

| Compound Number | R^A | R^B | salt |
|---|---|---|---|
| 30 | CON(piperazine)N-COCH2-morpholine | H | |
| 31 | CON(piperazine)N-CH2-(3,4-methylenedioxyphenyl) | H | |
| 32 | CON(piperazine)NCO$_2$Et | H | |
| 33 | CON(piperidine)-OMe | H | HCl |
| 34 | CON(piperidine)-SO$_2$Me | H | HCl |
| 35 | CON(piperazine)N-(2-pyridyl) | H | HCl |
| 36 | H | CON(piperazine)NCOMe | HCl |
| 37 | H | CON(morpholine) | HCl |
| 38 | H | CONH(CH$_2$)$_2$NHCOMe | HCl |
| 39 | CONH-(piperidine)-NCOMe | H | |
| 40 | CON(piperazine)NCO$^t$Bu | H | |
| 41 | CON(piperazine)N-CO-N(morpholine) | H | |

TABLE 1-continued

[Structure: 1H-indazole with vinyl linker to phenyl bearing R^A (para) and R^B (meta) substituents]

| Compound Number | R^A | R^B | salt |
|---|---|---|---|
| 42 | CON⟩—NHCO₂^tBu (piperidine) | H | |
| 43 | CON⟩—NHCOMe (piperidine) | H | |
| 44 | CON⟩N—C(O)—(4-pyridyl) (piperazine) | H | |
| 45 | CON⟩N—C(O)—(3-pyridyl) (piperazine) | H | |
| 46 | CON⟩N—C(O)—phenyl (piperazine) | H | |
| 47 | CON⟩NSO₂Me (piperazine) | H | |
| 48 | CON⟩N—C(O)—(1-imidazolyl) (piperazine) | H | |
| 49 | CON⟩—CO₂Et (piperidine) | H | |
| 50 | CON⟩—CO₂H (piperidine) | H | |
| 51 | CON⟩—C(O)—morpholine (piperidine) | H | |

TABLE 1-continued
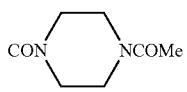
| Compound Number | R^A | R^B | salt |
|---|---|---|---|
| 52 | CONHCH$_2$CO$_2$Me | H | |
| 53 | CONHCH$_2$CO$_2$H | H | |
| 54 | 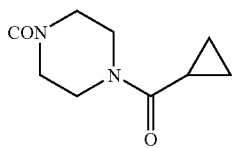 | OMe | |
| 55 | 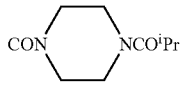 | H | |
| 56 | 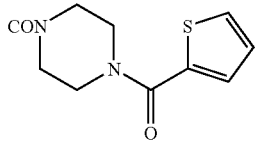 | H | |
| 57 | 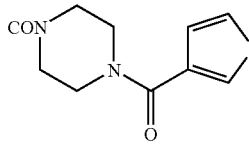 | H | |
| 58 | 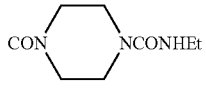 | H | |
| 59 | 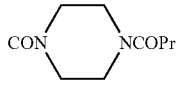 | H | |
| 60 | 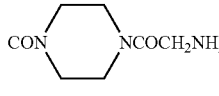 | H | |
| 61 |  | H | 2HCl |
| 62 | CONHCH$_2$CON​<morpholine> | H | |
| 63 | CONH(CH$_2$)$_2$NEt$_2$ | H | |
| 64 | 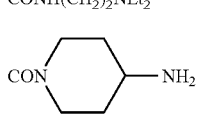 | H | |

TABLE 1-continued

| Compound Number | R^A | R^B | salt |
|---|---|---|---|
| 65 | CON(piperazine)NCOCH$_2$OMe | H | |
| 66 | CON(piperazine)NCO$^i$Bu | H | |
| 67 | CON(piperazine)N-SO$_2$-C$_6$H$_4$-Me | H | |
| 68 | CON(piperazine)NCOC(Me)$_2$OH | H | |
| 69 | CON(piperazine)NCOMe | Cl | |
| 70 | CONHCH$_2$CONHMe | H | |
| 71 | CON(piperazine)NCOCH$_2$NHCOMe | H | |
| 72 | CON(piperazine)NCOC(Me)$_2$CH$_2$OH | H | |
| 73 | CON(piperazine)NCOMe | Me | |
| 74 | CON(piperazine)NCOCH$_2$OH | H | HCl |
| 75 | CON(piperazine)NCO$_2$Me | H | HCl |
| 76 | CON(thiomorpholine) | H | HCl |

TABLE 1-continued

| Compound Number | R^A | R^B | salt |
|---|---|---|---|
| 77 | CON(piperazine)N-C(=O)-C(Me)(cyclopropyl) | H | |
| 78 | CON(piperazine)NCOCH₂ᵗBu | H | |
| 79 | CONH(CH₂)₂CO₂Et | H | |
| 80 | CON(piperidine)-CONHMe | H | |
| 81 | CON(piperidine)-CONEt₂ | H | |
| 82 | CON(homopiperazine)NCO₂ᵗBu | H | |
| 83 | CON(homopiperazine)NCO₂ᵗBu | Cl | |
| 84 | CON(piperazine)NCHO | Me | |
| 85 | CON(homopiperazine)NH | H | 2HCl |
| 86 | CON(piperidine)-CONH₂ | H | |
| 87 | CON(piperidine)-OH | H | |
| 88 | CON(Me)CH₂C(=O)N(morpholine) | H | |

TABLE 1-continued
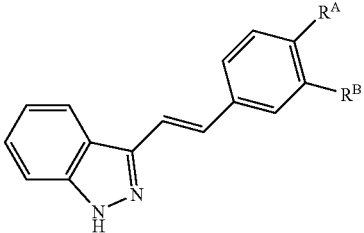
| Compound Number | R^A | R^B | salt |
|---|---|---|---|
| 89 | 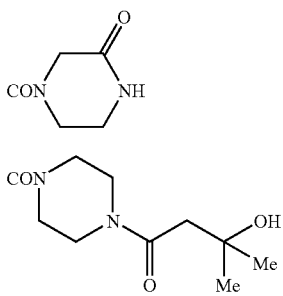 | H | |
| 90 | 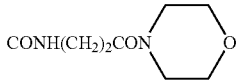 | H | |
| 91 | CONH(CH$_2$)$_2$CON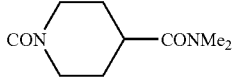 | H | |
| 92 | —CONMe$_2$ | H | |
| 93 | CONH(CH$_2$)$_2$CONEt$_2$ | H | |
| 94 | CONHCH$_2$CONEt$_2$ | H | |
| 95 | 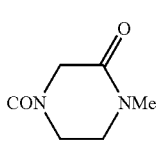 | Me | 2HCl |
| 96 | 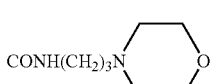 | H | |
| 97 | CONH(CH$_2$)$_3$N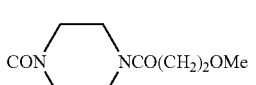 | H | 2HCl |
| 98 | 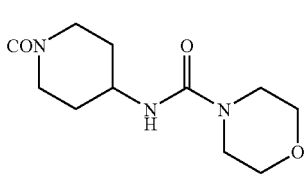NCO(CH$_2$)$_2$OMe | H | |
| 99 | 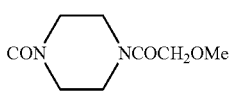 | H | |
| 100 | CONNCOCH$_2$OMe | Me | |

TABLE 1-continued

| Compound Number | R^A | R^B | salt |
|---|---|---|---|
| 101 | (S)-3-methylpiperazin-1-yl-carbonyl | H | 2HCl |
| 102 | (R)-3-methylpiperazin-1-yl-carbonyl | H | 2HCl |
| 103 | (2S,6S)-2,6-dimethylpiperazin-1-yl-carbonyl | H | 2HCl |
| 104 | 4-ethylpiperazin-1-yl-carbonyl | H | 2HCl |
| 105 | 4-(2-hydroxyethyl)piperazin-1-yl-carbonyl | H | |
| 106 | 4-morpholinopiperidin-1-yl-carbonyl | H | |
| 107 | 4-isopropylpiperazin-1-yl-carbonyl | H | HCl |
| 108 | 4-(2-dimethylaminoethyl)piperazin-1-yl-carbonyl | H | 2HCl |
| 109 | 4-(2-methoxyethyl)piperazin-1-yl-carbonyl | H | HCl |
| 110 | CONH(CH$_2$)$_2$NHEt | H | |
| 111 | CONH(CH$_2$)$_2$NH$_2$ | H | 2HCl |
| 112 | CONH(CH$_2$)$_2$NHMe | H | HCl |
| 113 | 4-(methoxyacetyl)-1,4-diazepan-1-yl-carbonyl | H | |

TABLE 1-continued
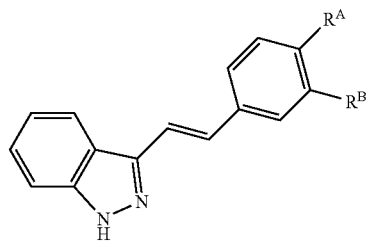
| Compound Number | R<sup>A</sup> | R<sup>B</sup> | salt |
|---|---|---|---|
| 114 | ![piperazine-CO-C(Me)(OH)Me with 7-membered ring] | H | |
| 115 | ![piperazinone N-CH2CH2Me] | H | HCl |
| 116 | ![piperazinone N-CH(Me)2... CHMe2] | H | HCl |
| 117 | ![tetrahydropyridine CON] | H | |
| 118 | ![2-Me piperazine N-CO-CH2-OMe] | H | HCl |
| 119 | ![2-Me piperazine N-CO-CH2-C(Me)(OH)Me] | H | HCl |
| 120 | CONH—[piperidine]—NH | H | 2HCl |
| 121 | ![piperazine-CH2-CO-pyrrolidine] | H | |
| 122 | ![pyrrolidine with NH2] | H | 2HCl |

TABLE 1-continued
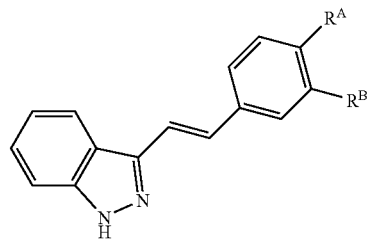
| Compound Number | R^A | R^B | salt |
|---|---|---|---|
| 123 | piperazine-CO-CH(NH₂)-CH₂OH (S) | H | 2HCl |
| 124 | piperazine-CO-(pyrrolidin-3-yl) | H | 2HCl |
| 125 | piperazine-CO-CH₂-N(Me)₂ | H | |
| 126 | piperazine-CO-CH₂-NH-CO-CH₂-CH(Me)₂ | H | |
| 127 | piperazine-CO-CH₂-O-CH₂-CH₂-OMe | H | |
| 128 | piperazine-CO-CH₂-O-CH₂-Me | H | |
| 129 | piperazine-CO-CH₂-CH₂-NH₂ | H | 2HCl |
| 130 | piperazine-CO-CH₂-NH-CO-CH₂-Ph | H | |
| 131 | piperazine-CO-C(Me)₂-NH₂ | H | 2HCl |

TABLE 1-continued

| Compound Number | R^A | R^B | salt |
|---|---|---|---|
| 132 | piperazine-N-C(O)-NH-C(O)-N(Me)Me | H | |
| 134 | piperazine-N with 2-oxo, N'-CH2CH2OMe | H | HCl |
| 135 | piperazine-N-CH2-C(O)-NH-CH(Me)Me | H | 2HCl |
| 136 | piperazine-N-C(O)-C(Me)(CH2OH)2 | H | HCl |
| 137 | piperazine-N-C(O)-CH2CH2CH2-NH-C(O)Me | H | |
| 138 | piperazine-N-C(O)-CH2-N(Me)-C(O)Me | H | |
| 139 | piperazine-N with 2,6-dioxo, N'-cyclopropyl | H | |
| 140 | piperazine-N-C(O)-(S)-pyrrolidin-2-yl | H | |

TABLE 1-continued

| Compound Number | R^A | R^B | salt |
|---|---|---|---|
| 141 | piperazine-N-CO, other N substituted with CH₂CH₂OMe, 2,6-dioxo (diketopiperazine) | H | |
| 142 | piperazine-N-CO-(piperidin-4-yl)-NH | H | 2HCl |
| 143 | piperazine-N-CO-(1-methylpiperidin-4-yl) | H | |
| 144 | piperazine-N-CO-CH₂-N(CH₂CH₂OH)₂ | H | 2HCl |
| 145 | piperazine-N-CO-(1-methylpyrrolidin-2-yl) | H | |
| 146 | piperazine-N-CO-(4-methylmorpholin-2-yl) | H | |
| 147 | piperazine-N-OH | H | |
| 148 | piperazine-N-NH-C(O)-O-C(Me)₃ | H | |

TABLE 1-continued

| Compound Number | R^A | R^B | salt |
|---|---|---|---|
| 149 | CON(piperazine)N—NH₂ | H | |
| 150 | CON(piperazine)N—NH—C(O)—N(morpholine) | H | |
| 151 | CON(piperazine)–(3,4-dioxocyclobut-1-enyl)–NH₂ | H | |
| 152 | CON(piperazine)–(3,4-dioxocyclobut-1-enyl)–NHMe | H | |
| 153 | CON(piperazine)–(3,4-dioxocyclobut-1-enyl)–NMe₂ | H | |
| 154 | CON(piperazine)–(3,4-dioxocyclobut-1-enyl)–N(pyrrolidine) | H | |

TABLE 1-continued

| Compound Number | $R^A$ | $R^B$ | salt |
|---|---|---|---|
| 155 | (piperazine-CO-N)-cyclobutenedione-N(piperidine) | H | |
| 156 | (piperazine-CO-N)-cyclobutenedione-N(morpholine) | H | |
| 157 | (piperazine-CO-N)-cyclobutenedione-N(N-Me-piperazine) | H | |
| 158 | (3-amino-pyrrolidine-CO-) | H | |
| 159 | (3-amino-pyrrolidine-CO-) | H | |

Next, pharmacological activities of Compound (I) will be illustrated below with reference to the test example. Test Example: Cytostatic activity on leukemia cell line and solid carcinoma cell line The cytostatic rates of a test compound on human acute myeloid leukemia cell lines MV-4-11 and ML-1, and human chronic myeloid leukemia cell line K562 were determined in the following manner.

Each cell was cultured using Roswell Park Memorial Institute's Medium (RPMI) 1640 (Gibco, Catalog No. 11875-093) containing 10% fetal bovine serum (Gibco, Catalog No. 10437-028) and 1% penicillin/streptomycin (1:1) (Gibco, Catalog No. 15140-122). Each 80 μL of the MV-4-11 cell having a concentration of $7.5 \times 10^4$ cells/mL (or the ML-1 cell or K562 cell having a concentration of $2.5 \times 10^4$ cells/mL) was inoculated to wells of a TC MICROWELL 96U plate (Nalge Nunc International, Catalog No. 163320) and was cultured in a 5% carbon dioxide gas incubator at 37° C. for 4 hours. As a blank, only RPMI medium (80 μL) was added to a well. Each 20 μL of a solution of the test compound in dimethyl sulfoxide (DMSO) which was prepared to make the final concentration to 10 μmol/L, was added to the MV-4-11 cell, ML-1 cell and K562 cell, respectively. Each 20 μL of DMSO was added to the control well and the blank well to a final concentration of 0.1%. After adding the test compound, the cells were incubated in a 5% carbon dioxide gas incubator at 37° C. for 72 hours. After adding 20 μL of WST-1 reagent {4-[3-(4-iodophenyl)-2-(4-nitrophenyl)-2H-5-tetrazolio]-1,3-benzene disulfonate sodium salt} (Roche Diagnostics K.K., Catalog No. 1644807) diluted to 50% with RPMI medium, the cells were further incubated at 37° C. for 2 hours. Then, the absorbances at 450 nm (reference wavelength: 690 nm) were determined with a microplate spectrophotometer SPECTRA max 340PC (Molecular Devices Corporation). The relative growth (%) of a well to which the test compound had been added was determined while setting the absorbance of a well to which not the test compound but DMSO alone had been added (control) at 100% and that of a well containing RPMI medium alone at 0%. The cytostatic rate (%) of the test compound was determined by subtracting the calculated relative growth from 100. The higher the cytostatic rate, the stronger the test compound exhibits cytostatic activity on the cell.

The cytostatic rate of a test compound on the human colon cancer cell line Colo205 was determined in the following manner.

The cell was cultured using Roswell Park Memorial Institute's Medium (RPMI) 1640 (Gibco, Catalog No. 11875-093) containing 10% fetal bovine serum (Gibco, Catalog No. 10437-028) and 1% penicillin/streptomycin (1:1) (Gibco, Catalog No. 15140-122). Each 80 μL of the Colo205 having a concentration of 1.25×10⁴ cells/mL was inoculated to wells of a TC MICROWELL 96F plate (Nalge Nunc International, Catalog No. 167008) and was cultured in a 5% carbon dioxide gas incubator at 37° C. for 24 hours. As a blank, only RPMI (80 μl) was added to a well. Each-20 μL of a solution of the test compound in DMSO which was prepared to make the final concentration to 10 μmol/L, was added to the Colo205 cell. Each 20 μL of DMSO was added to the control well and the blank well to a final concentration of 0.1%. After adding the test compound, the cell was incubated in a 5% carbon dioxide gas incubator at 37° C. for 72 hours. The cytostatic rate (%) was then determined in the same way as the leukemia cell lines.

The determined cytostatic rates (%) are shown in Table 2.

TABLE 2

| Compound Number | MV-4-11(%) (10 μmol/L) | ML-1(%) (10 μmol/L) | K562(%) (10 μmol/L) | Colo205(%) (10 μmol/L) |
|---|---|---|---|---|
| 1 | 98 | 93 | 95 | — |
| 7 | 97 | 97 | 98 | 89 |
| 8 | 95 | 84 | 95 | — |
| 9 | 91 | 90 | 98 | — |
| 10 | 91 | 83 | 99 | 41 |
| 13 | 94 | 90 | 99 | — |
| 14 | 76 | 84 | 98 | — |
| 15 | 91 | 94 | 100 | 92 |
| 16 | 89 | 97 | 94 | — |
| 18 | 98 | 76 | 91 | 85 |
| 19 | 97 | 89 | 78 | 89 |
| 27 | 94 | 77 | 55 | 80 |
| 32 | 94 | 80 | 86 | 85 |
| 40 | 98 | 67 | 96 | 88 |
| 41 | 97 | 83 | 95 | 90 |
| 44 | 98 | 85 | 92 | 91 |
| 46 | 98 | 82 | 93 | 87 |

TABLE 2-continued

| Compound Number | MV-4-11(%) (10 μmol/L) | ML-1(%) (10 μmol/L) | K562(%) (10 μmol/L) | Colo205(%) (10 μmol/L) |
|---|---|---|---|---|
| 47 | 97 | 88 | 88 | 91 |
| 51 | 98 | 89 | 95 | 90 |
| 55 | 97 | 83 | 81 | 89 |
| 56 | 98 | 78 | 87 | 88 |
| 58 | 96 | 74 | 89 | 85 |
| 61 | 98 | 79 | 85 | 87 |
| 63 | 98 | 87 | 76 | 88 |
| 64 | 98 | 89 | 91 | 94 |
| 65 | 97 | 86 | 85 | 88 |
| 66 | 99 | 74 | 89 | 83 |
| 68 | 97 | 79 | 91 | 90 |
| 72 | 100 | 80 | 95 | 93 |
| 73 | 97 | 87 | 68 | 89 |
| 75 | 99 | 88 | 85 | 88 |
| 77 | 98 | 80 | 95 | 86 |
| 78 | 98 | 64 | 90 | 82 |
| 81 | 98 | 77 | 95 | 85 |
| 85 | 99 | 78 | 90 | 89 |
| 86 | 98 | 87 | 88 | 89 |
| 87 | 99 | 88 | 76 | 86 |
| 89 | 98 | 86 | 61 | 92 |
| 90 | 98 | 79 | 85 | 88 |
| 92 | 98 | 88 | 89 | 89 |
| 95 | 96 | 70 | 93 | 86 |
| 98 | 98 | 79 | 89 | 88 |
| 99 | 97 | 86 | 94 | 95 |
| 101 | 99 | 77 | 92 | 87 |
| 103 | 100 | 83 | 88 | 89 |
| 105 | 96 | 85 | 90 | 88 |
| 106 | 98 | 58 | 35 | 37 |
| 107 | 98 | 77 | 91 | 84 |
| 112 | 98 | 83 | 81 | 88 |
| 116 | 98 | 79 | 88 | 91 |
| 122 | 98 | 79 | 93 | 89 |
| 124 | 98 | 83 | 94 | 87 |
| 125 | 98 | 79 | 91 | 86 |
| 126 | 97 | 87 | 89 | 95 |
| 128 | 98 | 79 | 87 | 88 |
| 131 | 99 | 85 | 98 | 91 |
| 132 | 100 | 88 | 95 | 91 |
| 134 | 100 | 88 | 91 | 91 |
| 135 | 99 | 79 | 93 | 87 |
| 136 | 99 | 82 | 94 | 91 |
| 138 | 99 | 88 | 94 | 91 |
| 140 | 99 | 82 | 95 | 85 |
| 143 | 100 | 84 | 95 | 92 |
| 145 | 99 | 85 | 94 | 92 |
| 147 | 99 | 89 | 77 | 83 |
| 148 | 98 | 81 | 91 | 83 |
| 150 | 97 | 67 | 90 | 88 |
| 155 | 97 | 79 | 96 | 88 |
| 156 | 99 | 85 | 94 | 92 |
| 158 | 98 | 80 | 90 | 91 |
| 159 | 99 | 86 | 93 | 92 |

Table 2 shows that Compound (I) exhibit cytostatic activities on the human acute myeloid leukemia cell lines MV-4-11 and ML-1, the human chronic myeloid leukemia cell line K562 and the human colon cancer cell line Colo205.

Compound (I) or pharmaceutically acceptable salt thereof may be used as it is or in various pharmaceutical forms depending upon the pharmacological effect, purpose of administration, etc. A pharmaceutical composition of the present invention can be manufactured by uniform mixing of Compound (I) or a pharmaceutically acceptable salt thereof in an amount which is effective as an active ingredient with pharmaceutically acceptable carriers. These carriers can have forms in a wide range according to desired dosage form for administration. It is preferred that the pharmaceutical composition is in a unit dosage form for oral administration or parental administration such as injection.

In the manufacture of tablets, excipient such as lactose and mannitol, disintegrator such as starch, lubricant such as magnesium stearate, binder such as polyvinyl alcohol and hydroxypropyl cellulose, and surfactant such as sucrose fatty acid esters and sorbitol fatty acid esters, etc. may be used in accordance with a conventional procedure. Tablets containing 1 to 200 mg of an active ingredient per tablet are preferred.

In the manufacture of injections, water, physiological saline, vegetable oil such as olive oil and peanut oil, solvent such as ethyl oleate and propylene glycol, dissolving agent such as sodium benzoate, sodium salicylate and urethane, isotonizing agent such as sodium chloride and glucose, preservative such as phenol, cresol, p-hydroxybenzoate and chlorobutanol, and antioxidant such as ascorbic acid and sodium pyrosulfite, etc. may be used by a conventional procedure.

Compound (I) or a pharmaceutically acceptable salt thereof can be administered either orally or parentally by means of injection solution, etc. The effective dose and frequency of administration vary depending on the dosage form, age, body weight and symptom of a patient, etc. In general, Compound (I) or a pharmaceutically acceptable salt thereof may preferably be administered in an amount of 0.01 to 100 mg/kg per day.

BEST MODE FOR CARRYING OUT THE INVENTION

The present invention will be illustrated in further detail with examples below which by no means limit the scope of the present invention.

In proton nuclear magnetic resonance spectra ($^1$H-NMR) used in the examples, exchangeable hydrogen may not be clearly observed in some compounds under some measuring conditions. With regard to indication of multiplicity of signals, the commonly used notation is here used, although br means a broad signal as judged by visual inspection.

EXAMPLE 1

(E)-N,N-Dimethyl-4-[2-(1H-indazol-3-yl)vinyl]benzamide (Compound 1)

Step 1

1H-indazole-3-carboxylic acid (45.2 g, 279 mmol) was suspended in THF (500 mL), and to the suspension were added 1-hydroxybenzotriazole dimethylammonium salt (55.7 g, 308 mmol) obtained in a similar manner to the known method [for example, Synthesis, page 285 (1992)] and 1-ethyl-3-(3-dimethylaminopropyl)carbodiimide hydrochloride (58.9 g, 307 mmol), followed by stirring at room temperature overnight. The reaction mixture was added with water, was extracted with ethyl acetate, and the organic layer was sequentially washed with a saturated aqueous sodium hydrogencarbonate solution and saturated brine, was dried over anhydrous sodium sulfate, and the solvent was evaporated under reduced pressure. The residue was recrystallized from mixed solvent of acetone/water to obtain N,N-dimethyl-1H-indazole-3-carboxamide (37.7 g, 71%).

$^1$H-NMR (270 MHz, CDCl$_3$) δ 3.22 (s, 3H), 3.40 (s, 3H), 7.24 (ddd, J=1.3, 6.9, 8.1 Hz, 1H), 7.40 (ddd, J=1.0, 6.9, 8.2 Hz, 1H), 7.48 (dd, J=1.3, 8.2 Hz, 1H), 8.15 (dd, J=1.0, 8.1 Hz, 1H), 10.7 (brs, 1H). TOF-MS (m/z); 190 [M+1]$^+$ Step 2

Lithium aluminum hydride (13.7 g, 36.1 mmol) was suspended in THF (500 mL), and the suspension was added with a solution of N,N-dimethyl-1H-indazole-3-carboxamide obtained in Step 1 (34.2 g, 181 mmol) in THF (250 mL), followed by stirring at room temperature under the flow of nitrogen gas for 30 minutes. The reaction mixture was mixed with sodium sulfate decahydrate, was stirred for further 1 hour and was filtered through Celite. The solvent was evaporated under reduced pressure to obtain 3-dimethylaminomethyl-1H-indazole (24.2 g, 76%).

$^1$H-NMR (270 MHz, CDCl$_3$) δ 2.33 (s, 6H), 3.85 (s, 2H), 7.16 (ddd, J=1.3, 6.6, 7.9 Hz, 1H), 7.38 (ddd, J=1.0, 6.6, 8.3 Hz, 1H), 7.45 (d, J=8.3 Hz, 1H), 7.87 (dd, J=1.0, 7.9 Hz, 1H), 10.0 (brs, 1H).

Step 3

3-Dimethylaminomethyl-1H-indazole (25.6 g, 146 mmol) obtained in Step 2 was dissolved in ethyl acetate (350 mL), and the solution was added with methyl iodide (33.3 mL, 535 mmol), followed by stirring at room temperature overnight. The resulting precipitates were collected by filtration to obtain (1H-indazol-3-ylmethyl)trimethylammonium iodide (45.0 g, 97%).

$^1$H-NMR (270 MHz, DMSO-d$_6$) δ 3.12 (s, 9H), 4.91 (s, 2H), 7.27 (dd, J=7.3, 8.1 Hz, 1H), 7.45 (dd, J=7.3, 8.1 Hz, 1H), 7.64 (d, J=8.1 Hz, 1H), 8.02 (d, J=8.1 Hz, 1H), 13.7 (brs, 1H). TOF-MS (m/z); 190 [M−127]$^+$ Step 4

(1H-indazol-3-ylmethyl)trimethylammonium iodide (45.0 g, 142 mmol) obtained in Step 3 was dissolved in DMF (220 mL), and the solution was mixed with triphenylphosphine (44.7 g, 170 mmol), followed by heating under reflux for 2.5 hours. After cooling to room temperature, the reaction mixture was added with diethyl ether and was stirred overnight. The resulting precipitates were collected by filtration to obtain (1H-indazol-3-ylmethyl)triphenylphosphonium iodide (68.3 g, 92%).

$^1$H-NMR (270 MHz, DMSO-d$_6$) δ 5.58 (d, J=15.2 Hz, 2H), 6.98 (ddd, J=1.0, 7.3, 8.3 Hz, 1H), 7.29 (ddd, J=1.0, 7.3, 8.3 Hz, 1H), 7.43 (d, J=8.3 Hz, 1H), 7.57 (d, J=8.3 Hz, 1H), 7.64-7.85 (m, 15H), 13.1 (brs, 1H). TOF-MS (m/z); 393 [M−127]$^+$ Step 5

(1H-indazol-3-ylmethyl)triphenylphosphonium iodide (3.20 g, 6.15 mmol) obtained in Step 4 was dissolved in methanol (60 mL), and the solution was added with methyl p-formylbenzoate (1.00 g, 6.09 mmol) and potassium carbonate (2.55 g, 18.5 mmol), followed by stirring at room temperature overnight. The reaction mixture was added with water, and was extracted with ethyl acetate, then the organic layer was washed with saturated brine, and was dried over anhydrous sodium sulfate, and the solvent was evaporated under reduced pressure. The residue was purified by thin-layer chromatography (chloroform/methanol=15/1), was further triturated in mixed solvent of ethyl acetate/diisopropyl ether to obtain methyl (E)-4-[2-(1H-indazol-3-yl)vinyl]benzoate (0.87 g, 51%).

$^1$H-NMR (270 MHz, DMSO-d$_6$) δ 3.84 (s, 3H), 7.21 (dd, J=7.1, 8.3 Hz, 1H), 7.40 (dd, J=7.1, 8.3 Hz, 1H), 7.55 (d, J=8.3 Hz, 1H), 7.55 (d, J=16.5 Hz, 1H), 7.70 (d, J=16.5 Hz, 1H), 7.84 (d, J=8.1 Hz, 2H), 7.95 (d, J=8.1 Hz, 2H), 8.19 (d, J=8.3 Hz, 1H). TOF-MS (m/z); 279 [M+1]$^+$

Step 6

Methyl (E)-4-[2-(1H-indazol-3-yl)vinyl]benzoate (0.71 g, 2.54 mmol) obtained in Step 5 was dissolved in methanol (2.6 mL), and the solution was added with an aqueous sodium hydroxide solution (1 mol/L, 5.00 mL), followed by heating under reflux for 1.5 hours. Methanol was evaporated under reduced pressure, the pH of the residue was adjusted to 3 or below with 6 mol/L hydrochloric acid under ice-cooling. The resulting precipitates were collected by filtration to obtain (E)-4-[2-(1H-indazol-3-yl)vinyl]benzoic acid (0.70 g, quantitative yield).

$^1$H-NMR (270 MHz, DMSO-$d_6$) δ 7.21 (dd, J=7.1, 7.9 Hz, 1H), 7.40 (dd, J=7.1, 8.6 Hz, 1H), 7.55 (d, J=8.6 Hz, 1H), 7.57 (d, J=16.5 Hz, 1H), 7.70 (d, J=16.5 Hz, 1H), 7.83 (d, J=8.3 Hz, 2H), 7.94 (d, J=8.3 Hz, 2H), 8.21 (d, J=7.9 Hz, 1H), 13.2 (brs, 1H). TOF-MS (m/z); 265 [M+1]$^+$ Step 7

A mixture of a solution of (E)-4-[2-(1H-indazol-3-yl)vinyl]benzoic acid obtained in Step 6 in THF (0.125 mol/L, 0.40 mL, 0.05 mmol), a solution of dimethylamine in THF (1 mol/L, 0.08 mL, 0.08 mmol), a solution of 1-hydroxybenzotriazole in THF (0.33 mol/L, 0.20 mL, 0.07 mmol) and polymer-bound 1-ethyl-3-(3-dimethylaminopropyl)carbodiimide (1 mol/g, 0.07 g, 0.07 mmol) was shaken at room temperature overnight. The reaction mixture was filtered, the solvent was evaporated by blowing air to the filtrate, and the residue was added with THF (0.6 mL), polyvinylpyridine (0.03 g, 0.29 mmol) and 4-chloroformyl polystyrene (3.5 mol/g, 0.03 g, 0.11 mmol), followed by shaking at room temperature overnight. The reaction mixture was filtered, and the solvent was evaporated by blowing air to the filtrate. The residue was added with ethanol (0.5 mL) and ion-exchange resin [Bio-Rad AG (registered trademark) 1 X-8 OH form, 0.15 g], followed by shaking for 10 minutes. The mixture was filtered, the resin was washed with ethanol, and the adsorbate was eluted with a 4 mol/L solution of hydrogen chloride in ethyl acetate. The solvent was evaporated by blowing air to the eluate, the residue was purified by thin-layer chromatography (chloroform/methanol=9/1) to obtain Compound 1 (0.4 mg, 3%).

TOF-MS (m/z); 292 [M+1]$^+$

EXAMPLE 2

(E)-N-(3-Methylbutyl)-4-[2-(1H-indazol-3-yl)vinyl]benzamide (Compound 2)

In a similar manner to Step 7 of Example 1, Compound 2 (1.2 mg, 7%) was obtained using a solution of (E)-4-[2-(1H-indazol-3-yl)vinyl]benzoic acid obtained in Step 6 of Example 1 in THF (0.125 mol/L, 0.40 mL, 0.05 mmol) and a solution of isoamylamine in THF (1 mol/L, 0.08 mL, 0.08 mmol).

TOF-MS (m/z); 334 [M+1]$^+$

EXAMPLE 3

(E)-N-Benzyl-4-[2-(1H-indazol-3-yl)vinyl]benzamide (Compound 3)

In a similar manner to Step 7 of Example 1, Compound 3 (1.3 mg, 7%) was obtained using a solution of (E)-4-[2-(1H-indazol-3-yl)vinyl]benzoic acid obtained in Step 6 of Example 1 in THF (0.125 mol/L, 0.40 mL, 0.05 mmol) and a solution of benzylamine in THF (1 mol/L, 0.08 mL, 0.08 mmol).

TOF-MS (m/z); 354 [M+1]$^+$

EXAMPLE 4

(E)-N-(2-Methoxyethyl)-4-[2-(1H-indazol-3-yl)vinyl]benzamide (Compound 4)

In a similar manner to Step 7 of Example 1, Compound 4 (0.5 mg, 3%) was obtained using a solution of (E)-4-[2-(1H-indazol-3-yl)vinyl]benzoic acid obtained in Step 6 of Example 1 in THF (0.125 mol/L, 0.40 mL, 0.05 mmol) and a solution of 2-methoxyethylamine in THF (1 mol/L, 0.08 mL, 0.08 mmol).

TOF-MS (m/z); 322 [M+1]$^+$

EXAMPLE 5

(E)-N-(2-Methoxyethyl)-N-methyl-4-[2-(1H-indazol-3-yl)vinyl]benzamide (Compound 5)

(E)-4-[2-(1H-indazol-3-yl)vinyl]benzoic acid (0.18 g, 0.67 mmol) obtained in Step 6 of Example 1 was dissolved in THF (4 mL), and the solution was added with N-(2-methoxyethyl)methylamine (0.11 mL, 1.00 mmol), 1-hydroxybenzotriazole monohydrate (0.12 g, 0.85 mmol) and 1-ethyl-3-(3-dimethylaminopropyl)carbodiimide hydrochloride (0.18 g, 0.92 mmol), followed by stirring at room temperature for 2 hours. The reaction mixture was added with a saturated aqueous sodium hydrogencarbonate solution, was extracted with ethyl acetate, the organic layer was sequentially washed with water and saturated brine, was dried over anhydrous magnesium sulfate, and the solvent was evaporated under reduced pressure. The residue was purified by silica gel column chromatography (chloroform/methanol=25/1) to obtain Compound 5 (0.22 g, 99%).

$^1$H-NMR (270 MHz, DMSO-$d_6$) δ 2.97 (s, 3H), 3.20 (brm, 2H), 3.31 (s, 3H), 3.50 (brm, 2H), 7.20 (dd, J=7.3, 7.9 Hz, 1H), 7.39 (m, 1H), 7.40 (d, J=8.2 Hz, 2H), 7.54 (d, J=16.7 Hz, 1H), 7.55 (d, J=8.3 Hz, 1H), 7.60 (d, J=16.7 Hz, 1H), 7.75 (d, J=8.2 Hz, 2H), 8.19 (d, J=7.9 Hz, 1H), 13.2 (brs, 1H). TOF-MS (m/z); 336 [M+1]$^+$

EXAMPLE 6

(E)-N-(2-Dimethylaminoethyl)-4-[2-(1H-indazol-3-yl)vinyl]benzamide (Compound 6)

In a similar manner to Example 5, Compound 6 (0.06 g, 42%) was obtained using (E)-4-[2-(1H-indazol-3-yl)vinyl]benzoic acid (0.12 g, 0.40 mmol) obtained in Step 6 of Example 1, N,N-dimethylethylenediamine (0.07 mL, 0.60 mmol), 1-hydroxybenzotriazole monohydrate (0.07 g, 0.52 mmol) and 1-ethyl-3-(3-dimethylaminopropyl)carbodiimide hydrochloride (0.11 g, 0.57 mmol).

$^1$H-NMR (270 MHz, DMSO-$d_6$) δ 2.18 (s, 6H), 2.40 (t, J=6.6 Hz, 2H), 3.31 (m, 2H), 7.21 (dd, J=7.3, 7.9 Hz, 1H), 7.39 (dd, J=7.3, 7.9 Hz, 1H), 7.55 (d, J=7.9 Hz, 1H), 7.56 (d, J=16.8 Hz, 1H), 7.65 (d, J=16.8 Hz, 1H), 7.79 (d, J=8.3 Hz, 2H), 7.85 (d, J=8.3 Hz, 2H), 8.20 (d, J=7.9 Hz, 1H), 8.38 (brm, 1H), 13.2 (brs, 1H). TOF-MS (m/z); 335 [M+1]$^+$

EXAMPLE 7

(E)-N-{5-[2-(1H-Indazol-3-yl)vinyl]-2-(2-morpholinoethoxy)phenyl}methanesulfonamide (Compound 7)

Step 1

A solution of 4-hydroxy-3-nitrobenzaldehyde (6.37 g, 38.1 mmol) in DMF (10.0 mL) was added with potassium carbonate (15.8 g, 114 mmol) and 2-(N-morpholino)ethyl chloride hydrochloride (7.09 g, 38.1 mmol), followed by stirring at 80° C. for 7 hours. After cooling to room temperature, the reaction mixture was added with water (40 mL), was extracted with ethyl acetate (100 mL×4), the organic layer was dried over anhydrous sodium sulfate, was treated with a 4 mol/L solution of hydrogen chloride in ethyl acetate to obtain 4-(2-morpholinoethoxy)-3-nitrobenzaldehyde hydrochloride (6.07 g, 50%).

¹H-NMR (270 MHz, DMSO-d₆) δ 3.24-4.00 (m, 10H), 4.78 (t, J=4.7 Hz, 2H), 7.62 (d, J=8.8 Hz, 1H), 8.22 (dd, J=2.0, 8.8 Hz, 1H), 8.48 (d, J=2.0 Hz, 1H), 9.97 (s, 1H), 11.6 (brs, 1H). APCI-MS (m/z); 281 [M+H]⁺

Step 2

A solution of 4-(2-morpholinoethoxy)-3-nitrobenzaldehyde hydrochloride obtained in Step 1 (2.97 g, 9.38 mmol) in dichloromethane (10.0 mL) was added with trimethyl orthoformate (15.0 mL, 13.7 mmol) and a 10% solution of hydrogen chloride in methanol (5.00 mL), followed by stirring at room temperature for 4 hours. The reaction mixture was added with potassium carbonate (10.0 g, 72.4 mmol), then stirred at room temperature for 5 hours, and the solvent was evaporated under reduced pressure. The residue was added with water (50 mL) and was extracted with ethyl acetate (50 mL×3). After drying over anhydrous sodium sulfate, the solvent was evaporated under reduced pressure to obtain 4-dimethoxymethyl-1-(2-morpholinoethoxy)-2-nitrobenzene (2.98 g, 97%).

¹H-NMR (300 MHz, CDCl₃) δ 2.60 (brt, J=4.7 Hz, 4H), 2.85 (t, J=5.6 Hz, 2H), 3.32 (s, 6H), 3.71 (brt, J=4.7 Hz, 4H), 4.25 (t, J=5.6 Hz, 2H), 5.39 (s, 1H), 7.07 (d, J=8.6 Hz, 1H), 7.59 (dd, J=2.2, 8.6 Hz, 1H), 7.93 (d, J=2.2 Hz, 1H). ESI-MS (m/z); 327 [M+H]⁺

Step 3

A solution of 4-dimethoxymethyl-1-(2-morpholinoethoxy)-2-nitrobenzene obtained in Step 2 (2.97 g, 9.10 mmol) in ethanol (30.0 mL) was added with platinum oxide (0.02 g, 0.10 mmol), followed by stirring at room temperature under hydrogen atmosphere for 2 hours. The reaction mixture was filtered, the solvent of filtrate was evaporated under reduced pressure, the resulting crude product was crystallized from mixed solvent of ethyl acetate/hexane (1/1) to obtain 5-dimethoxymethyl-2-(2-morpholinoethoxy)aniline (0.70 g, 26%).

¹H-NMR (300 MHz, CDCl₃) δ 2.57 (brt, J=4.7 Hz, 4H), 2.78 (t, J=5.7 Hz, 2H), 3.30 (s, 6H), 3.72 (brt, J=4.7 Hz, 4H), 3.91 (brs, 2H), 4.12 (t, J=5.7 Hz, 2H), 5.25 (s, 1H), 6.76-6.81 (m, 3H). ESI-MS (m/z); 297 [M+H]⁺

Step 4

A solution of 5-dimethoxymethyl-2-(2-morpholinoethoxy)aniline obtained in Step 3 (0.27 g, 0.91 mmol) in dichloromethane (2.00 mL) was added with methanesulfonyl chloride (0.11 mL, 1.42 mmol) and pyridine (0.50 mL, 6.18 mmol), followed by stirring at room temperature for 10 hours. The reaction mixture was added with hydrochloric acid (3 mol/L, 3.00 mL), was stirred at room temperature for 20 minutes, was neutralized with a saturated aqueous sodium hydrogencarbonate solution (50 ml) and was extracted with ethyl acetate (50 mL×3). The organic layer was dried over anhydrous sodium sulfate, the solvent was evaporated under reduced pressure. the crude product was purified by silica gel column chromatography (chloroform, then methanol/chloroform=1/6) to obtain 3-methanesulfonylamino-4-(2-morpholinoethoxy)benzaldehyde (0.28 g, 95%).

¹H-NMR (300 MHz, CDCl₃) δ 2.56 (brt, J=4.6 Hz, 4H), 2.70 (t, J=5.5 Hz, 2H), 2.99 (s, 3H), 3.80 (brt, J=4.6 Hz, 4H), 4.28 (t, J=5.5 Hz, 2H), 7.14 (d, J=8.4 Hz, 1H), 7.71 (dd, J=2.0, 8.4 Hz, 1H), 8.03 (d, J=2.0 Hz, 1H), 9.91 (s, 1H). ESI-MS (m/z); 327 [M−H]⁻

Step 5

A solution of 3-methanesulfonylamino-4-(2-morpholinoethoxy)benzaldehyde obtained in Step 4 (0.27 g, 0.83 mmol) in DMF (5.0 mL) was added with (1H-indazol-3-ylmethyl)triphenylphosphonium iodide obtained in Step 4 of Example 1 (0.40 g, 0.77 mmol) and potassium carbonate (0.23 g, 1.66 mmol), followed by stirring at room temperature for 2 hours, and further stirring at 60° C. for 11 hours. After cooling to room temperature, the solvent was evaporated under reduced pressure, the crude product was purified by silica gel chromatography [amino-modified chemically bound silica gel Chromatorex (registered trademark) NH, Fuji Silysia Chemical Ltd.; ethyl acetate, then methanol/ethyl acetate=1/19], was crystallized from ethyl acetate to obtain Compound 7 (0.05 g, 14%).

¹H-NMR (300 MHz, CDCl₃) δ 2.58-2.61 (m, 6H), 2.94 (s, 3H), 3.87 (brt, J=4.7 Hz, 4H), 4.23 (t, J=5.6 Hz, 2H), 7.07 (d, J=8.4 Hz, 1H), 7.23-7.29 (m, 1H), 7.39 (d, J=16.5 Hz, 1H), 7.48 (d, J=16.5 Hz, 1H), 7.40-7.51 (m, 3H), 7.77 (d, J=2.2 Hz, 1H), 8.04 (d, J=8.2 Hz, 1H). ESI-MS (m/z); 443 [M+H]⁺

EXAMPLE 8

(E)-5-[2-(1H-Indazol-3-yl)vinyl]-2-(2-morpholinoethoxy)benzamide (Compound 8)

Step 1

A solution of 4-hydroxybenzaldehyde (10.0 g, 81.9 mmol) in chloroform (100 mL) was added with bromine (4.30 mL, 83.5 mmol), followed by stirring at room temperature for 2 hours. The reaction mixture was added with water (100 mL), and the solvent of the organic layer was evaporated under reduced pressure to obtain 3-bromo-4-hydroxybenzaldehyde as a pale yellow solid (quantitative yield).

¹H-NMR (270 MHz, CDCl₃) δ 6.27 (s, 1H), 7.15 (d, J=8.4 Hz, 1H), 7.78 (dd, J=1.9, 8.4 Hz, 1H), 8.04 (d, J=1.9 Hz, 1H), 9.83 (s, 1H). ESI-MS (m/z); 199, 201 [M−H]⁻

Step 2

In a similar manner to Step 1 of Example 7, 3-bromo-4-(2-morpholinoethoxy)benzaldehyde hydrochloride (10.9 g, 49%) was obtained using 3-bromo-4-hydroxybenzaldehyde obtained in Step 1 (14.3 g, 71.0 mmol), potassium carbonate (20.0 g, 145 mmol) and 2-(N-morpholino)ethyl chloride hydrochloride (13.5 g, 72.6 mmol).

¹H-NMR (270 MHz, CDCl₃) δ 2.65 (brt, J=4.7 Hz, 4H), 2.91 (t, J=5.6 Hz, 2H), 3.73 (brt, J=4.7 Hz, 4H), 4.26 (t, J=5.6 Hz, 2H), 7.00 (d, J=8.4 Hz, 1H), 7.80 (dd, J=2.0, 8.4 Hz, 1H), 8.08 (d, J=2.0 Hz, 1H), 9.84 (s, 1H). ESI-MS (m/z); 314, 316 [M+H]⁺

Step 3

In a similar manner to Step 2 of Example 7, 1-bromo-5-dimethoxymethyl-2-(2-morpholinoethoxy)benzene (4.57 g, 98%) was obtained using 3-bromo-4-(2-morpholinoethoxy)benzaldehyde hydrochloride obtained in Step 2 (4.08 g, 13.0 mmol), trimethyl orthoformate (20.0 mL, 18.3 mmol) and a 10% solution of hydrogen chloride in methanol (10 mL).

¹H-NMR (300 MHz, CDCl₃) δ 2.60 (brt, J=4.7 Hz, 4H), 2.85 (t, J=5.6 Hz, 2H), 3.32 (s, 6H), 3.71 (brt, J=4.7 Hz, 4H), 4.25 (t, J=5.6 Hz, 2H), 5.39 (s, 1H), 7.07 (d, J=8.6 Hz, 1H), 7.59 (dd, J=2.2, 8.6 Hz, 1H), 7.93 (d, J=2.2 Hz, 1H). ESI-MS (m/z); 327 [M+H]⁺

Step 4

A solution of 1-bromo-5-dimethoxymethyl-2-(2-morpholinoethoxy)benzene (3.11 g, 8.63 mmol) obtained in Step 3 in THF (40.0 mL) was cooled to −78° C., to which n-butyllithium (1.60 mol/L, 20.0 mL, 32.0 mmol) was added dropwise for 3 minutes, followed by stirring at −78° C. for 5 minutes. The reaction mixture was added with dry ice and was stirred for 3 hours while warming to room temperature. The solvent of the reaction mixture was evaporated under reduced pressure. The residue was added with a 1 mol/L aqueous ammonium acetate solution (30 mL), was purified by HP-20 column chromatography (water, then acetonitrile/water=2/1), then crystallized from mixed solvent of ethyl acetate/hexane (1/1) to obtain 5-dimethoxymethyl-2-(2-morpholinoethoxy)benzoic acid (0.58 g, 21%).

$^1$H-NMR (300 MHz, CD$_3$OD) δ 2.64 (brt, J=4.8 Hz, 4H), 2.83 (t, J=5.6 Hz, 2H), 3.28 (s, 6H), 3.70 (brt, J=4.8 Hz, 4H), 4.19 (t, J=5.6 Hz, 2H), 5.31 (s, 1H), 6.95 (d, J=8.4 Hz, 1H), 7.29 (dd, J=2.2, 8.4 Hz, 1H), 7.43 (d, J=2.2 Hz, 1H). ESI-MS (m/z); 362 [M+H]$^+$ Step 5

A solution of 5-dimethoxymethyl-2-(2-morpholinoethoxy)benzoic acid (0.40 g, 1.23 mmol) obtained in Step 4 in DMF (5.00 mL) was added with 1-hydroxybenzotriazole ammonium salt (0.30 g, 1.97 mmol) and 1-ethyl-3-(3-dimethylaminopropyl)carbodiimide hydrochloride (0.35 g, 1.84 mmol), followed by stirring at room temperature for 35 hours. The solvent of the reaction mixture was evaporated under reduced pressure, and the residue was added with hydrochloric acid (3 mol/L, 3.00 mL), followed by stirring at room temperature for 1 hour. The reaction mixture was neutralized with a saturated aqueous sodium hydrogencarbonate solution (50 mL) and was extracted with ethyl acetate (50 mL×3). After drying over anhydrous sodium sulfate, the solvent was evaporated under reduced pressure to obtain 5-formyl-2-(2-morpholinoethoxy)benzamide (0.25 g, 73%).

$^1$H-NMR (300-MHz, CDCl$_3$) δ 2.55 (brt, J=4.7 Hz, 4H), 2.87 (t, J=5.4 Hz, 2H), 3.71 (brt, J=4.7 Hz, 4H), 4.32 (t, J=5.4 Hz, 2H), 5.80 (brs, 1H), 7.10 (d, J=8.6 Hz, 1H), 8.04 (dd, J=2.2, 8.6 Hz, 1H), 8.50 (brs, 1H), 8.71 (d, J=2.2 Hz, 1H), 9.98 (s, 1H). ESI-MS (m/z); 279 [M+H]$^+$ Step 6

In a similar manner to Step 5 of Example 7, Compound 8 (0.13 g, 46%) was obtained using 5-formyl-2-(2-morpholinoethoxy)benzamide (0.20 g, 0.72 mmol) obtained in Step 5, (1H-indazol-3-ylmethyl)triphenylphosphonium iodide (0.38 g, 0.72 mmol) obtained in Step 4 of Example 1 and potassium carbonate (0.20 g, 1.45 mmol).

$^1$H-NMR (300 MHz, CDCl$_3$) δ 2.55 (brt, J=4.6 Hz, 4H), 2.84 (t, J=5.4 Hz, 2H), 3.71 (brt, J=4.6 Hz, 4H), 4.27 (t, J=5.4 Hz, 2H), 5.71 (brs, 1H), 7.00 (d, J=8.6 Hz, 1H), 7.23-7.28 (m, 1H), 7.40-7.51 (m, 2H), 7.44 (d, J=16.5 Hz, 1H), 7.53 (d, J=16.5 Hz, 1H), 7.69 (dd, J=2.4, 8.6 Hz, 1H), 8.04 (d, J=8.1 Hz, 1H), 8.45 (d, J=2.4 Hz, 1H), 8.62 (brs, 1H), 10.1 (brs, 1H). ESI-MS (m/z); 393 [M+H]$^+$

EXAMPLE 9

(E)-1-{4-[2-(1H-indazol-3-yl)vinyl]benzoyl}morpholine (Compound 9)

In a similar manner to Example 5, Compound 9 (2.65 g, 84%) was obtained using (E)-4-[2-(1H-indazol-3-yl)vinyl]benzoic acid (2.50 g, 9.47 mmol) obtained in Step 6 of Example 1, morpholine (1.24 mL, 14.2 mmol), 1-hydroxybenzotriazole monohydrate (1.70 g, 11.2 mmol) and 1-ethyl-3-(3-dimethylaminopropyl)carbodiimide hydrochloride (2.54 g, 13.3 mmol).

$^1$H-NMR (270 MHz, CDCl$_3$) δ 3.50-3.80 (brm, 8H), 6.91 (d, J=3.3 Hz, 1H), 7.45-7.54 (m, 6H), 7.66 (d, J=8.4 Hz, 1H), 8.07 (d, J=8.3 Hz, 1H), 10.2 (br, 1H). ESI-MS (m/z); 334 [M+H]$^+$

EXAMPLE 10

(E)-N-(2-morpholinoethyl)-4-[2-(1H-indazol-3-yl)vinyl]benzamide (Compound 10)

In a similar manner to Example 5, Compound 10 (0.24 g, 55%) was obtained using (E)-4-[2-(1H-indazol-3-yl)vinyl]benzoic acid (0.30 g, 1.14 mmol) obtained in Step 6 of Example 1, 2-morpholinoethylamine (0.22 mL, 1.71 mmol), 1-hydroxybenzotriazole monohydrate (0.20 g, 1.31 mmol) and 1-ethyl-3-(3-dimethylaminopropyl)carbodiimide hydrochloride (0.31 g, 1.62 mmol).

$^1$H-NMR (270 MHz, CDCl$_3$) δ 2.54 (brt, J=4.6 Hz, 4H), 2.64 (t, J=6.0 Hz, 2H), 3.59 (q, J=5.5 Hz, 2H), 3.76 (brt, J=4.8 Hz, 4H), 6.92 (brm, 1H), 7.26 (t, J=6.6 Hz, 1H), 7.43 (t, J=7.3 Hz, 2H), 7.51 (d, J=8.4 Hz, 2H), 7.63 (d, J=8.4 Hz, 2H), 7.79 (d, J=8.4 Hz, 2H), 8.04 (d, J=8.1 Hz, 1H). ESI-MS (m/z); 377 [M+H]$^+$

EXAMPLE 11

(E)-N-[2-(acetylamino)ethyl]-4-[2-(1H-indazol-3-yl)vinyl]benzamide (Compound 11)

In a similar manner to Example 5, Compound 11 (0.30 g, 64%) was obtained using (E)-4-[2-(1H-indazol-3-yl)vinyl]benzoic acid (0.35 g, 1.33 mmol) obtained in Step 6 of Example 1, N-acetylethylenediamine (0.41 mL, 4.01 mmol), 1-hydroxybenzotriazole monohydrate (0.23 g, 1.51 mmol) and 1-ethyl-3-(3-dimethylaminopropyl)carbodiimide hydrochloride (0.36 g, 1.62 mmol).

$^1$H-NMR (270 MHz, DMSO-d$_6$) δ 1.81 (s, 3H), 3.19-3.31 (m, 4H), 7.21 (t, J=7.5 Hz, 1H), 7.39 (t, J=7.3 Hz, 1H), 7.52-7.88 (m, 4H), 7.98 (brm, 1H), 8.20 (d, J=8.1 Hz, 1H), 8.51 (brt, J=8.1 Hz, 1H), 13.3 (brs, 1H). ESI-MS (m/z); 349 [M+H]$^+$

EXAMPLE 12

(E)-N-methyl-5-[2-(1H-indazol-3-yl)vinyl]-2-(2-morpholinoethoxy)benzamide (Compound 12)

Step 1

In a similar manner to Example 5, N-methyl-5-dimethoxymethyl-2-(2-morpholinoethyl)benzamide (0.16 g, 94%) was obtained using 5-dimethoxymethyl-2-(2-morpholinoethoxy)benzoic acid (0.19 g, 0.59 mmol) obtained in Step 4 of Example 8, methylamine hydrochloride (0.08 g, 1.18 mmol), 1-hydroxybenzotriazole monohydrate (0.13 g, 0.85 mmol) and 1-ethyl-3-(3-dimethylaminopropyl)carbodiimide hydrochloride (0.18 g, 1.17 mmol).

$^1$H-NMR (300 MHz, CDCl$_3$) δ 2.56 (brt, J=4.6 Hz, 4H), 2.88 (t, J=5.4 Hz, 2H), 3.05 (d, J=4.8 Hz, 3H), 3.75 (brt, J=4.6 Hz, 4H), 4.32 (t, J=5.4 Hz, 2H), 7.07 (d, J=8.6 Hz, 1H), 7.99 (dd, J=2.2, 8.6 Hz, 1H), 8.43 (brs, 1H), 8.71 (d, J=2.2 Hz, 1H), 9.97 (s, 1H). APCI-MS (m/z); 293 [M+H]$^+$ Step 2

In a similar manner to Step 5 of Example 7, Compound 12 (0.06 g, 25%) was obtained using N-methyl-5-dimethoxymethyl-2-(2-morpholinoethyl)benzamide (0.16 g, 0.54 mmol) obtained in Step 1, (1H-indazol-3-ylmethyl)triphenylphosphonium iodide (0.13 g, 0.85 mmol) obtained in Step 4 of Example 1 and potassium carbonate (0.08 g, 1.18 mmol).

$^1$H-NMR (270 MHz, CDCl$_3$) δ 2.56 (brt, J=4.6 Hz, 4H), 2.85 (t, J=5.4 Hz, 2H), 3.07 (d, J=4.8 Hz, 3H), 3.76 (brt, J=4.6 Hz, 4H), 4.26 (t, J=5.4 Hz, 2H), 6.98 (d, J=8.6 Hz, 1H), 7.23-7.29 (m, 1H), 7.42 (d, J=16.5 Hz, 1H), 7.43-7.50 (m, 2H), 7.53 (d, J=16.5 Hz, 1H), 7.65 (dd, J=2.3, 8.6 Hz, 1H), 8.04 (d, J=8.2 Hz, 1H), 8.46 (d, J=2.3 Hz, 1H), 8.53 (brs, 1H), 9.99 (brs, 1H). APCI-MS (m/z); 407 [M+H]$^+$

EXAMPLE 13

(E)-4-Acetyl-1-{4-[2-(1H-indazol-3-yl)vinyl]benzoyl}piperazine (Compound 13)

In a similar manner to Example 5, Compound 13 (0.69 g, 98%) was obtained using (E)-4-[2-(1H-indazol-3-yl)vinyl]benzoic acid (0.50 g, 1.89 mmol) obtained in Step 6 of Example 1, 4-acetylpiperazine (0.73 g, 5.67 mmol), 1-hydroxybenzotriazole monohydrate (0.33 g, 2.17 mmol) and 1-ethyl-3-(3-dimethylaminopropyl)carbodiimide hydrochloride (0.51 g, 2.66 mmol).

$^1$H-NMR (270 MHz, DMSO-d$_6$) δ 1.81 (s, 3H), 3.42-3.63 (brm, 8H), 7.22 (t, J=7.2 Hz, 1H), 7.41 (t, J=7.2 Hz, 1H), 7.45 (d, J=8.3 Hz, 2H), 7.52-7.68 (m, 3H), 7.80 (d, J=8.2 Hz, 2H), 8.21 (d, J=8.2 Hz, 1H), 13.2 (brs, 1H). ESI-MS (m/z); 375 [M+H]$^+$

EXAMPLE 14

(E)-N-Methyl-4-[2-(1H-indazol-3-yl)vinyl]benzamide (Compound 14)

In a similar manner to Example 5, Compound 14 (0.12 g, 55%) was obtained using (E)-4-[2-(1H-indazol-3-yl)vinyl]benzoic acid (0.20 g, 0.76 mmol) obtained in Step 6 of Example 1, methylamine hydrochloride (0.08 g, 1.19 mmol) and 1-ethyl-3-(3-dimethylaminopropyl)carbodiimide hydrochloride (0.20 g, 1.06 mmol).

$^1$H-NMR (270 MHz, DMSO-d$_6$) δ 2.79 (d, J=4.4 Hz, 3H), 7.21 (t, J=7.2 Hz, 1H), 7.40 (t, J=7.2 Hz, 1H), 7.50-7.88 (m, 7H), 8.20 (d, J=8.1 Hz, 1H), 8.42 (brm, 1H), 13.2 (br, 1H). ESI-MS (m/z); 278 [M+H]$^+$

EXAMPLE 15

(E)-N,N-Diethyl-4-[2-(1H-indazol-3-yl)vinyl]benzamide hydrochloride (Compound 15)

In a similar manner to Example 5, a free base of Compound 15 was obtained using (E)-4-[2-(1H-indazol-3-yl)vinyl]benzoic acid (0.50 g, 1.89 mmol) obtained in Step 6 of Example 1, diethylamine (0.29 mL, 2.80 mmol) and 1-ethyl-3-(3-dimethylaminopropyl)carbodiimide hydrochloride (0.51 g, 2.67 mmol). Then, the free base of Compound 15 was dissolved in acetic acid (5 mL) and was added with a 4 mol/L solution of hydrogen chloride in ethyl acetate (1.00 mL), followed by stirring at room temperature for 30 minutes. The resulting precipitates were collected by filtration to obtain Compound 15 (0.11 g, 18%).

$^1$H-NMR (270 MHz, DMSO-d$_6$) δ 1.10 (brm, 6H), 3.27-3.37 (brm, 4H), 7.21 (t, J=7.9 Hz, 1H), 7.35 (d, J=8.1 Hz, 2H), 7.38 (t, J=6.9 Hz, 1H), 7.49-7.64 (m, .3H), 7.75 (d, J=8.2 Hz, 2H), 8.19 (d, J=8.2 Hz, 1H), 10.9 (br, 1H). ESI-MS (m/z); 320 [M+H]$^+$

EXAMPLE 16

(E)-4-ethylenedioxy-1-{4-[2-(1H-indazol-3-yl)vinyl]benzoyl}piperidine hydrochloride (Compound 16)

In a similar manner to Example 5, a free base of Compound 16 was obtained using (E)-4-[2-(1H-indazol-3-yl)vinyl]benzoic acid (0.50 g, 1.89 mmol) obtained in Step 6 of Example 1, 1,4-dioxa-8-azaspiro[4.5]decane (0.36 mL, 2.81 mmol) and 1-ethyl-3-(3-dimethylaminopropyl)carbodiimide hydrochloride (0.51 g, 2.67 mmol), and then the free base of Compound 16 was treated with 4 mol/L hydrogen chloride-ethyl acetate solution to obtain Compound 16 (0.56 g, 76%) in a similar manner to Example 15.

$^1$H-NMR (270 MHz, DMSO-d$_6$) δ 1.61-1.71 (brm, 4H), 4.17-4.39 (brm, 8H), 7.20 (t, J=8.1 Hz, 1H), 7.39 (t, J=8.2 Hz, 1H), 7.41 (d, J=8.1 Hz, 2H), 7.47-7.64 (m, 3H), 7.76 (d, J=8.2 Hz, 2H), 8.19 (d, J=8.2 Hz, 1H), 11.0 (br, 1H). ESI-MS (m/z); 390 [M+H]$^+$

EXAMPLE 17

(E)-4-{4-[2-(1H-indazol-3-yl)vinyl]benzoyl}piperazine-1-carboxylic acid 1,1-dimethylethylester (Compound 17)

In a similar manner to Example 5, Compound 17 (0.27 g, 33%) was obtained using (E)-4-[2-(1H-indazol-3-yl)vinyl]benzoic acid (0.50 g, 1.89 mmol) obtained in Step 6 of Example 1, 4-(tert-butoxycarbonyl)piperazine (0.53 g, 2.84 mmol), 1-hydroxybenzotriazole monohydrate (0.33 g, 2.17 mmol) and 1-ethyl-3-(3-dimethylaminopropyl)carbodiimide hydrochloride (0.51 g, 2.66 mmol).

$^1$H-NMR (270 MHz, DMSO-d$_6$) δ 1.41 (s, 9H), 3.23-3.57 (brm, 8H), 7.20 (t, J=7.2 Hz, 1H), 7.39 (t, J=7.2 Hz, 1H), 7.42 (d, J=8.3 Hz, 2H), 7.53 (d, J=16.7 Hz, 1H), 7.55 (d, J=8.2 Hz, 1H), 7.63 (d, J=16.7 Hz, 1H), 7.78 (d, J=8.2 Hz, 2H), 8.19 (d, J=8.2 Hz, 1H), 13.2 (brs, 1H). ESI-MS (m/z); 431 [M–H]$^−$

EXAMPLE 18

(E)-1-{4-[2-(1H-indazol-3-yl)vinyl]benzoyl}piperazine (Compound 18)

Step 1

To the solution of Compound 17 (0.27 g, 0.62 mmol) in methanol (2 mL), 10% hydrogen chloride-methanol solution (2 mL) was added, followed by stirring at 60° C. for 30 minutes. After cooling to room temperature, methanol was evaporated to obtain dihydrochloride of Compound 18 (0.21 g, 74%).

Step 2

Dihydrochloride of Compound 18 (0.10 g) obtained in Step 1 was added with chloroform (20 mL) and saturated aqueous sodium hydrogencarbonate solution (20 mL), followed by stirring at room temperature for 1 hour, then the reaction mixture was extracted with chloroform. The organic layer was washed with saturated brine and dried over anhydrous sodium sulfate, and the solvent was evaporated under reduced pressure. After the residue was recrystallized from ethyl acetate, the obtained crystal was washed with mixed solvent of ethyl acetate/hexane (1:1) to obtain Compound 18 (0.022 g, 27%).

¹H-NMR (270 MHz, CDCl₃) δ 2.78-3.02 (m, 4H), 3.32-3.89 (m, 4H), 7.20-7.52 (m, 7H), 7.60 (d, J=8.4 Hz, 2H), 8.03 (d, J=8.1 Hz, 1H), 10.8 (brs, 1H).
APCI-MS (m/z); 333 [M+H]⁺

EXAMPLE 19

(E)-4-{4-[2-(1H-indazol-3-yl)vinyl]benzoyl}piperazine-1-carbaldehyde (Compound 19)

In a similar manner to Example 5, Compound 19 (0.34 g, 99%) was obtained using Compound 18 (0.40 g, 0.95 mmol), formic acid (0.03 mL), 1-hydroxybenzotriazole monohydrate (0.27 g, 1.96 mmol) and 1-ethyl-3-(3-dimethylaminopropyl)carbodiimide hydrochloride (0.17 g, 0.90 mmol).

¹H-NMR (270 MHz, DMSO-d₆) δ 3.45-3.57 (brm, 8H), 7.21 (t, J=7.2 Hz, 1H), 7.40 (t, J=7.2 Hz, 1H), 7.45 (d, J=8.3 Hz, 2H), 7.53 (d, J=16.6 Hz, 1H), 7.54 (d, J=8.2 Hz, 1H), 7.64 (d, J=16.6 Hz, 1H), 7.79 (d, J=8.2 Hz, 2H), 8.06 (s, 1H), 8.20 (d, J=8.2 Hz, 1H), 13.2 (brs, 1H). ESI-MS (m/z); 361 [M+H]⁺

EXAMPLE 20

(E)-1-{4-[2-(1H-indazol-3-yl)vinyl]benzoyl}-4-methylpiperidine (Compound 20)

In a similar manner to Example 5, Compound 20 (160 mg, 25%) was obtained using (E)-4-[2-(1H-indazol-3-yl)vinyl]benzoic acid (0.50 g, 1.89 mmol) obtained in Step 6 of Example 1, 4-methylpiperidine (0.34 mL, 2.84 mmol), 1-ethyl-3-(3-dimethylaminopropyl)carbodiimide hydrochloride (510 mg, 2.67 mmol) and N-methylmorpholine (0.41 mL, 3.73 mmol).

¹H-NMR (270 MHz, CDCl₃) δ 0.92 (d, J=6.3 Hz, 3H), 1.02-1.16 (m, 2H), 1.58-1.64 (m, 3H), 2.82-2.94 (brm, 4H), 7.20 (dt, J=7.9, 0.8 Hz, 1H), 7.36-7.42 (m, 3H), 7.49-7.54 (m, 2H), 7.61 (d, J=17.0 Hz, 1H), 7.76 (brd, J=8.3 Hz, 2H), 8.19 (d, J=8.6 Hz, 1H), 13.2 (br, 1H). ESI-MS (m/z); 346 [M+H]⁺

EXAMPLE 21

(E)-1-{4-[2-(1H-indazol-3-yl)vinyl]benzoyl}-4-methylpiperazine (Compound 21)

In a similar manner to Example 5, Compound 21 (230 mg, 35%) was obtained using (E)-4-[2-(1H-indazol-3-yl)vinyl]benzoic acid (0.50 g, 1.89 mmol) obtained in Step 6 of Example 1, N-methylpiperazine (0.315 mL, 2.84 mmol), 1-ethyl-3-(3-dimethylaminopropyl)carbodiimide hydrochloride (510 mg, 2.67 mmol) and N-methylmorpholine (0.41 mL, 3.73 mmol).

¹H-NMR (270 MHz, DMSO-d₆) δ 2.20 (s, 3H), 2.32-2.40 (m, 4H), 3.47-3.53 (m, 4H), 7.21 (dt, J=7.3, 0.8 Hz, 1H), 7.38-7.45 (m, 3H), 7.50-7.66 (m, 2H), 7.68 (d, J=16.8 Hz, 1H), 7.77 (brd, J=8.1 Hz, 2H), 8.19 (d, J=8.4 Hz, 1H), 13.2 (br, 1H). ESI-MS (m/z); 347 [M+H]⁺

EXAMPLE 22

(E)-1-{4-[2-(1H-indazol-3-yl)vinyl]benzoyl}-4-(2-pyrimidinyl)piperazine (Compound 22)

In a similar manner to Example 5, Compound 22 (56.0 mg, 7%) was obtained using (E)-4-[2-(1H-indazol-3-yl)vinyl]benzoic acid (0.50 g, 1.89 mmol) obtained in Step 6 of Example 1, N-(2-pyrimidinyl)piperazine (674 mg, 2.84 mmol), 1-ethyl-3-(3-dimethylaminopropyl)carbodiimide hydrochloride (510 mg, 2.67 mmol) and N-methylmorpholine (0.41 mL, 3.73 mmol).

¹H-NMR (270 MHz, DMSO-d₆) δ 3.45-3.56 (brm, 4H), 3.75-3.84 (brm, 4H), 6.66 (t, J=7.8 Hz, 1H), 7.21 (dt, J=7.9, 0.8 Hz, 1H), 7.40 (dt, J=7.3, 0.8 Hz, 1H), 7.45-7.57 (m, 4H), 7.66 (d, J=16.7 Hz, 1H), 7.79 (brd, J=8.0 Hz, 2H), 8.20 (d, J=8.2 Hz, 1H), 8.38 (d, J=8.4 Hz, 2H), 13.2 (brs, 1H). ESI-MS (m/z); 411 [M+H]⁺

EXAMPLE 23

(E)-4-(2-furoyl)-1-{4-[2-(1H-indazol-3-yl)vinyl]benzoyl}piperazine (Compound 23)

In a similar manner to Example 5, Compound 23 (436 mg, 53%) was obtained using (E)-4-[2-(1H-indazol-3-yl)vinyl]benzoic acid (500 mg, 1.89 mmol) obtained in Step 6 of Example 1, N-(2-furoyl)piperazine (512 mg, 2.84 mmol), 1-ethyl-3-(3-dimethylaminopropyl)carbodiimide hydrochloride (510 mg, 2.67 mmol) and N-methylmorpholine (0.42 mL, 3.82 mmol).

¹H-NMR (270 MHz, DMSO-d₆) δ 3.48-3.81 (brm, 8H), 6.63 (m, 1H), 7.02 (d, J=3.5 Hz, 1H), 7.21 (t, J=7.4 Hz, 1H), 7.39 (t, J=7.1 Hz, 1H), 7.49-7.68 (m, 4H), 7.78-7.84 (m, 3H), 8.20 (d, J=8.1 Hz, 2H), 13.2 (brs, 1H). ESI-MS (m/z); 427 [M+H]⁺

EXAMPLE 24

(E)-1-{4-[2-(1H-indazol-3-yl)vinyl]benzoyl}-4-phenyl-1,2,3,6-tetrahydropyridine (Compound 24)

In a similar manner to Example 5, Compound 24 (98.9 mg, 12%) was obtained using (E)-4-[2-(1H-indazol-3-yl)vinyl]benzoic acid (0.50 g, 1.89 mmol) obtained in Step 6 of Example 1, 4-phenyl-1,2,3,6-tetrahydropyridine hydrochloride (555 mg, 2.84 mmol), 1-ethyl-3-(3-dimethylaminopropyl)carbodiimide hydrochloride (510 mg, 2.66 mmol) and N-methylmorpholine (0.42 mL, 3.82 mmol).

¹H-NMR (270 MHz, DMSO-d₆) δ 2.57 (br, 2H), 3.30 (br, 2H), 4.01-4.03 (m, 2H), 7.23 (t, J=7.6 Hz, 1H), 7.24-7.58 (m, 10H), 7.64 (d, J=16.6 Hz, 1H), 7.80 (d, J=8.1 Hz, 2H), 8.20 (d, J=8.1 Hz, 1H), 13.2 (br, 1H). ESI-MS (m/z); 406 [M+H]⁺

EXAMPLE 25

(E)-N-[2-(2-pyridyl)ethyl]-4-[2-(1H-indazol-3-yl)vinyl]benzamide (Compound 25)

In a similar manner to Example 5, Compound 25 (238 mg, 34%) was obtained using (E)-4-[2-(1H-indazol-3-yl)vinyl]benzoic acid (500 mg, 1.89 mmol) obtained in Step 6 of Example 1, 2-(2-aminoethyl)pyridine (0.34 mL, 2.84 mmol), 1-ethyl-3-(3-dimethylaminopropyl)carbodiimide hydrochloride (510 mg, 2.67 mmol) and N-methylmorpholine (0.42 mL, 3.82 mmol).

¹H-NMR (270 MHz, DMSO-d₆) δ 3.01 (t, J=7.2 Hz, 2H), 3.62 (q, J=6.8 Hz, 2H), 7.18-7.30 (m, 3H), 7.40 (t, J=7.1 Hz, 1H), 7.51-7.86 (m, 8H), 8.19 (d, J=8.2 Hz, 1H), 8.50 (brd, J=4.0 Hz, 1H), 8.57 (brt, J=5.5 Hz, 1H), 13.2 (br, 1H). ESI-MS (m/z); 369 [M+H]⁺

EXAMPLE 26

(E)-4-[2-(1H-indazol-3-yl)vinyl]-N-[3-(2-oxopyrrolidin-1-yl)propyl]benzamide hydrochloride (Compound 26)

In a similar manner to Example 5, a free base of Compound 26 was obtained using (E)-4-[2-(1H-indazol-3-yl)vinyl]benzoic acid (500 mg, 1.89 mmol) obtained in Step 6 of Example 1, 1-(3-aminopropyl)-2-pyrrolidinone (0.27 mL, 1.93 mmol), 1-ethyl-3-(3-dimethylaminopropyl)carbodiimide hydrochloride (510 mg, 2.67 mmol) and N-methylmorpholine (0.42 mL, 3.82 mmol), then the free base of Compound 26 was dissolved in acetic acid (5.00 mL), and was added with 4 mol/L hydrogen chloride-ethyl acetate solution (1.00 mL), followed by stirring at room temperature for 30 minutes. The precipitate in the reaction mixture was filtered to obtain Compound 26 (124 mg, 15%).

$^1$H-NMR (270 MHz, DMSO-$d_6$) δ 1.70 (quin, J=6.9 Hz, 2H), 1.93 (quin, J=7.6 Hz, 2H), 2.22 (t, J=8.1 Hz, 2H), 3.23 (brt, J=7.0 Hz, 4H), 3.35 (t, J=7.0 Hz, 2H), 7.21 (dt, J=7.9, 0.8 Hz, 1H), 7.39 (dt, J=8.2, 1.3 Hz, 1H), 7.51-7.57 (m, 3H), 7.67 (d, J=16.7 Hz, 1H), 7.71-7.88 (m, 4H), 8.19 (d, J=8.1 Hz, 1H), 8.50 (br, 1H). ESI-MS (m/z); 389 [M+H]$^+$

EXAMPLE 27

(E)-N-{3-[2-(1H-indazol-3-yl)vinyl]phenyl}methanesulfonamide (Compound 27)

In a similar manner to Step 5 of Example 1, Compound 27 (50.0 mg, 6%) was obtained using (1H-indazol-3-ylmethyl)triphenylphosphonium iodide (880 mg, 3.01 mmol), N-(3-formylphenyl)methanesulfonamide (880 mg, 3.01 mmol) and potassium carbonate (694 mg, 5.02 mmol).

$^1$H-NMR (270 MHz, CDCl$_3$) δ 7.17 (d, J=2.0 Hz, 1H), 7.25-7.30 (m, 1H), 7.42-7.53 (m, 9H), 8.03 (d, J=8.1 Hz, 1H). APCI-MS (m/z); 314 [M+H]$^+$

EXAMPLE 28

(E)-N-{3-[2-(1H-indazol-3-yl)vinyl]phenyl}benzenesulfonamide hydrochloride (Compound 28)

In a similar manner to Step 5 of Example 1, a free base of Compound 28 was obtained using (1H-indazol-3-ylmethyl)triphenylphosphonium iodide (672 mg, 2.3 mmol), N-(3-formylphenyl)benzenesulfonamide (500 mg, 1.91 mmol) and potassium carbonate (528 mg, 3.82 mmol), and then the free base of Compound 28 was treated with 4 mol/L hydrogen chloride-ethyl acetate solution to obtain Compound 28 (85.3 mg, 12%) in a similar manner to Example 15.

$^1$H-NMR (270 MHz, CDCl$_3$) δ 6.85-7.10 (m, 2H), 7.25 (d, J=2.4 Hz, 1H), 7.36-7.55 (m, 7H), 7.23-7.64 (m, 4H), 7.84-7.90 (m, 2H), 8.03 (d, J=8.1 Hz, 1H). APCI-MS (m/z); 376 [M+H]$^+$

EXAMPLE 29

(E)-1-{4-[2-(1H-indazol-3-yl)vinyl]benzoyl}-4-(ethoxycarbonylmethyl)piperazine (Compound 29)

In a similar manner to Example 5, Compound 29 (86.7 mg, 11%) was obtained using (E)-4-[2-(1H-indazol-3-yl)vinyl]benzoic acid (500 mg, 1.89 mmol) obtained in Step 6 of Example 1, 1-(ethoxycarbonylmethyl)piperazine (490 mg, 2.84 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (0.42 mL, 3.82 mmol).

$^1$H-NMR (270 MHz, DMSO-$d_6$) δ 1.18 (t, J=7.2 Hz, 3H), 2.48-2.55 (m, 4H), 3.30 (s, 2H), 3.51-3.68 (m, 4H), 4.08 (q, J=7.2 Hz, 2H), 6.81 (d, J=12.9 Hz, 1H), 6.92-6.99 (m, 2H), 7.24-7.33 (m, 4H), 7.50 (d, J=7.9 Hz, 1H), 7.66 (brd, J=8.2 Hz, 2H), 13.2 (br, 1H). APCI-MS (m/z); 419 [M+H]$^+$

EXAMPLE 30

(E)-1-{4-[2-(1H-indazol-3-yl)vinyl]benzoyl}-4-(2-morpholino-2-oxoethyl)piperazine (Compound 30)

In a similar manner to Example 5, Compound 30 (363 mg, 42%) was obtained using (E)-4-[2-(1H-indazol-3-yl)vinyl]benzoic acid (500 mg, 1.89 mmol) obtained in Step 6 of Example 1, 1-(ethoxycarbonylmethyl)piperazine (606 mg, 2.84 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (0.42 mL, 3.82 mmol).

$^1$H-NMR (270 MHz, DMSO-$d_6$) δ 2.49-2.54 (m, 4H), 3.21 (s, 2H), 3.35-3.58 (m, 10H), 7.21 (t, J=7.1 Hz, 1H), 7.35-7.43 (m, 3H), 7.50-7.66 (m, 4H), 7.76 (d, J=8.1 Hz, 2H), 8.19 (brd, J=8.1 Hz, 2H), 13.2 (br, 1H). APCI-MS (m/z); 460 [M+H]$^+$

EXAMPLE 31

(E)-1-{4-[2-(1H-indazol-3-yl)vinyl]benzoyl}-4-(benzo[1,3]dioxol-5-yl)methylpiperazine (Compound 31)

In a similar manner to Example 5, Compound 31 (246 mg, 28%) was obtained using (E)-4-[2-(1H-indazol-3-yl)vinyl]benzoic-acid (0.50 g, 1.89 mmol) obtained in Step 6 of Example 1, 4-(benzo[1,3]dioxol-5-yl)methylpiperazine (626 mg, 2.85 mmol), 1-ethyl-3-(3-dimethylaminopropyl)carbodiimide hydrochloride (510 mg, 2.66 mmol) and N-methylmorpholine (0.42 mL, 3.82 mmol).

$^1$H-NMR (270 MHz, DMSO-$d_6$) δ 2.48-2.49 (m, 4H), 3.41 (br, 6H), 5.98 (s, 2H), 6.82-6.86 (m, 2H), 7.22 (d, J=7.4 Hz, 1H), 7.36-7.41 (m, 4H), 7.54 (d, J=6.8 Hz, 1H), 7.56 (d, J=16.8 Hz, 1H), 7.62 (d, J=16.8 Hz, 1H), 7.76 (d, J=8.4 Hz, 2H), 8.19 (d, J=7.4 Hz, 1H), 13.2 (br, 1H). APCI-MS (m/z); 467 [M+H]$^+$

EXAMPLE 32

(E)-1-{4-[2-(1H-indazol-3-yl)vinyl]benzoyl}-4-ethoxycarbonylpiperazine (Compound 32)

In a similar manner to Example 5, Compound 32 (346 mg, 45%) was obtained using (E)-4-[2-(1H-indazol-3-yl)vinyl]benzoic acid (500 mg, 1.89 mmol) obtained in Step 6 of Example 1, 1-piperazine carboxylic acid ethyl ester (0.42 mL, 2.84 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (0.42 mL, 3.82 mmol).

$^1$H-NMR (270 MHz, DMSO-$d_6$) δ 1.18 (t, J=7.1 Hz, 3H), 3.27-3.43 (m, 8H), 4.05 (q, J=7.1 Hz, 2H), 7.21 (t, J=7.1 Hz, 1H), 7.37-7.45 (m, 3H), 7.53-7.67 (m, 3H), 7.78 (d, J=8.2 Hz, 2H), 8.19 (brd, J=8.2 Hz, 1H), 13.2 (br, 1H). ESI-MS (m/z); 405 [M+H]$^+$

EXAMPLE 33

(E)-1-{4-[2-(1H-indazol-3-yl)vinyl]benzoyl}-4-methoxypiperidine hydrochloride (Compound 33)

In a similar manner to Example 5, a free base of Compound 33 was obtained using (E)-4-[2-(1H-indazol-3-yl)vinyl]benzoic acid (0.30 g, 1.14 mmol) obtained in Step 6 of Example 1, 4-methoxypiperidine (200 mg, 1.71 mmol), 1-ethyl-3-(3-dimethylaminopropyl)carbodiimide hydrochloride (305 mg, 1.60 mmol) and N-methylmorpholine (0.3 mL, 32.28 mmol), and then the free base of Compound 33 was dissolved in ethyl acetate (5.00 mL) and was added with 4 moL/L hydrogen chloride-dioxane solution (1.00 mL) followed by stirring at room temperature for 30 minutes. The precipitate in the reaction mixture was filtered to obtain Compound 33 (45.7 mg, 10%).

$^1$H-NMR (270 MHz, DMSO-$d_6$) δ 1.43 (br, 2H), 1.83-1.90 (m, 2H), 3.26 (s, 3H), 3.40-3.47 (m, 1H), 4.64 (br, 4H), 7.20 (d, J=8.1 Hz, 1H), 7.36-7.41 (m, 1H), 7.39 (d, J=8.1 Hz, 2H), 7.52 (d, J=16.6 Hz, 1H), 7.57 (d, J=8.1 Hz, 1H), 7.62 (d, J=16.6 Hz, 1H), 7.76 (d, J=8.1 Hz, 2H), 8.19 (d, J=8.1 Hz, 1H). ESI-MS (m/z); 362 [M+H]$^+$

EXAMPLE 34

(E)-1-{4-[2-(1H-indazol-3-yl)vinyl]benzoyl}-4-methanesulfonylpiperidine hydrochloride (Compound 34)

In a similar manner to Example 5, a free base of Compound 34 was obtained using (E)-4-[2-(1H-indazol-3-yl)vinyl]benzoic acid (0.40 g, 1.52 mmol) obtained in Step 6 of Example 1, 4-methanesulfonylpiperidine (469 mg, 2.35 mmol), 1-ethyl-3-(3-dimethylaminopropyl)carbodiimide hydrochloride (410 mg, 2.13 mmol) and N-methylmorpholine (0.34 mL, 3.03 mmol), and then the free base of Compound 34 was dissolved in ethyl acetate (5.00 mL) and was added with 4 moL/L hydrogen chloride-ethyl acetate solution (1.00 mL), followed by stirring at room temperature for 30 minutes. The precipitate in the reaction mixture was filtered to obtain Compound 34 (8.2 mg, 1.2%).

$^1$H-NMR (270 MHz, DMSO-$d_6$) δ 1.16 (br, 2H), 3.37 (br, 6H), 3.82 (s, 3H), 3.91 (br, 1H), 7.22 (d, J=8.2 Hz, 1H), 7.31-7.43 (m, 1H), 7.33 (d, J=8.2 Hz, 2H), 7.57 (d, J=16.6 Hz, 1H), 7.71 (d, J=16.6 Hz, 1H), 7.83 (d, J=8.2 Hz, 1H), 7.96 (d, J=8.2 Hz, 2H), 8.21 (d, J=8.2 Hz, 1H). ESI-MS (m/z); 410 [M+H]$^+$

EXAMPLE 35

(E)-1-{4-[2-(1H-indazol-3-yl)vinyl]benzoyl}-4-(2-pyridyl)piperazine hydrochloride (Compound 35)

In a similar manner to Example 5, a free base of Compound 35 was obtained using (E)-4-[2-(1H-indazol-3-yl)vinyl]benzoic acid (0.50 g, 1.89 mmol) obtained in Step 6 of Example 1, 2-pyridylpiperazine (671 mg, 2.84 mmol), 1-ethyl-3-(3-dimethylaminopropyl)carbodiimide hydrochloride (510 mg, 2.67 mmol) and N-methylmorpholine (0.84 mL, 7.64 mmol), and then the free base of Compound 35 was dissolved in acetic acid (5.00 mL) and was added with 4 moL/L hydrogen chloride-ethyl acetate solution (1.00 mL), followed by stirring at room temperature for 30 minutes. The precipitate in the reaction mixture was filtered to obtain Compound 35 (190 mg, 23%).

$^1$H-NMR (270 MHz, DMSO-$d_6$) δ 3.60-3.81 (m, 8H), 6.96 (brt, J=7.1, 0.9 Hz, 1H), 7.21 (t, J=7.2 Hz, 1H), 7.29-7.40 (m, 2H), 7.47-7.62 (m, 4H), 7.65 (d, J=16.4 Hz, 1H), 7.81 (d, J=8.1 Hz, 2H), 7.95-8.06 (m, 2H), 8.19 (brd, J=8.1 Hz, 1H). APCI-MS (m/z); 410 [M+H]$^+$

EXAMPLE 36

(E)-4-acetyl-1-{3-[2-(1H-indazol-3-yl)vinyl]benzoyl}piperazine hydrochloride (Compound 36)

In a similar manner to Example 5, a free base of Compound 36 was obtained using (E)-3-[2-(1H-indazol-3-yl)vinyl]benzoic acid (500 mg, 1.89 mmol) obtained in a similar manner to Step 6 of Example 1, N-acetylpiperazine (490 mg, 3.82 mmol), 1-hydroxybenzotriazole monohydrate (332 mg, 2.46 mmol), 1-ethyl-3-(3-dimethylaminopropyl)carbodiimide hydrochloride (510 mg, 2.66 mmol) and N-methylmorpholine (0.42 mL, 3.82 mmol), and then the free base of Compound 36 was dissolved in ethyl acetate (5.00 mL) and was added with 4 moL/L hydrogen chloride-ethyl acetate solution (1.00 mL), followed by stirring at room temperature for 30 minutes. The precipitate in the reaction mixture was filtered to obtain Compound 36 (491 mg, 69%).

$^1$H-NMR (270 MHz, DMSO-$d_6$) δ 2.02 (s, 3H), 3.51-3.61 (brm, 8H), 7.19 (t, 1H, J=7.9 Hz), 7.30 (brd, J=7.7 Hz, 1H), 7.39 (brd, J=5.8 Hz, 1H), 7.44-7.66 (m, 4H), 7.75 (brm, 1H), 7.80 (brd, J=7.6 Hz, 1H), 8.21 (d, J=8.2 Hz, 1H). APCI-MS (m/z); 375 [M+H]$^+$

EXAMPLE 37

(E)-4-{3-[2-(1H-indazol-3-yl)vinyl]benzoyl}morpholine hydrochloride (Compound 37)

In a similar manner to Example 5, a free base of Compound 37 was obtained using (E)-3-[2-(1H-indazol-3-yl)vinyl]benzoic acid (500 mg, 1.89 mmol) obtained in a similar manner to Step 6 of Example 1, morpholine (0.33 mL, 3.82 mmol), 1-hydroxybenzotriazole monohydrate (332 mg, 2.46 mmol), 1-ethyl-3-(3-dimethylaminopropyl)carbodiimide hydrochloride (510 mg, 2.66 mmol) and N-methylmorpholine (0.42 mL, 3.82 mmol), and then the free base of Compound 37 was dissolved in ethyl acetate (5.00 mL) and was added with 4 moL/L hydrogen chloride-ethyl acetate solution (1.00 mL), followed by stirring at room temperature for 30 minutes. The precipitate in the reaction mixture was filtered to obtain Compound 37 (240 mg, 34%).

$^1$H-NMR (270 MHz, DMSO-$d_6$) δ 3.50-3.90 (brm, 8H), 7.20 (brt, J=7.8 Hz, 1H), 7.27 (brd, J=7.6 Hz, 1H), 7.39 (brd, J=7.8 Hz, 1H), 7.43-7.66 (m, 4H), 7.73 (m, 1H), 7.80 (brd, J=7.9 Hz, 1H), 8.21 (d, J=8.2 Hz, 1H). APCI-MS (m/z); 334 [M+H]$^+$

EXAMPLE 38

(E)-N-[2-(acetylamino)ethyl]-3-[2-(1H-indazol-3-yl)vinyl]benzamide hydrochloride (Compound 38)

In a similar manner to Example 5, Compound 38 (240 mg, 36%) was obtained using (E)-3-[2-(1H-indazol-3-yl)vinyl]benzoic acid (500 mg, 1.89 mmol) obtained in a similar manner to Step 6 of Example 1, N-acetylethylenediamine (290 mg, 3.82 mmol), 1-hydroxybenzotriazole monohydrate (332 mg, 2.46 mmol), 1-ethyl-3-(3-dimethylaminopropyl)carbodiimide hydrochloride (510 mg, 2.66 mmol) and N-methylmorpholine (420 μL, 3.82 mmol).

$^1$H-NMR (270 MHz, DMSO-$d_6$) δ 1.82 (s, 3H), 3.22-3.35 (m, 4H), 7.21 (dt, J=7.9, 0.7 Hz, 1H), 7.37-7.99 (m, 7H), 8.19 (brs, 1H), 8.20 (brt, J=8.4 Hz, 1H), 13.3 (brs, 1H). ESI-MS (m/z); 349 [M+H]$^+$

EXAMPLE 39

(E)-N-(1-acetylpiperidin-4-yl)-4-[2-(1H-indazol-3-yl)vinyl]benzamide (Compound 39)

In a similar manner to Example 5, Compound 39 (156 mg, 21%) was obtained using (E)-4-[2-(1H-indazol-3-yl)vinyl]benzoic acid (500 mg, 1.89 mmol) obtained in Step 6 of Example 1, 4-amino-1-acetylpiperidine (507 mg, 2.84 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (650 μL, 5.73 mmol).

¹H-NMR (270 MHz, DMSO-d₆) δ 1.53-1.62 (m, 2H), 1.72-1.78 (m, 2H), 1.98-2.07 (m, 2H), 2.82 (brd, J=10.7 Hz, 2H), 3.32 (s, 3H), 3.79 (m, 1H), 7.18-7.42 (m, 3H), 7.50-7.57 (m, 2H), 7.66 (d, J=16.2 Hz, 1H), 7.78 (d, J=8.4 Hz, 2H), 7.82 (d, J=8.4 Hz, 2H), 8.19 (brd, J=8.1 Hz, 1H), 13.2 (br, 1H). ESI-MS (m/z); 389 [M+H]⁺

EXAMPLE 40

(E)-1-{4-[2-(1H-indazol-3-yl)vinyl]benzoyl}-4-(pivaloyl)piperazine (Compound 40)

In a similar manner to Example 5, Compound 40 (74.7 mg, 10%) was obtained using (E)-4-[2-(1H-indazol-3-yl)vinyl]benzoic acid (500 mg, 1.89 mmol) obtained in Step 6 of Example 1, N-pivaloylpiperazine (587 mg, 2.84 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (1.04 mL, 9.55 mmol).

¹H-NMR (270 MHz, DMSO-d₆) δ 1.19 (s, 9H), 3.31-3.59 (m, 8H), 7.21 (t, J=7.9 Hz, 1H), 7.38 (d, J=8.2 Hz, 2H), 7.49 (t, J=8.4 Hz, 1H), 7.50-7.67 (m, 3H), 7.78 (d, J=8.2 Hz, 2H), 8.19 (brd, J=8.3 Hz, 1H), 13.2 (br, 1H).

ESI-MS (m/z); 417 [M+H]⁺

EXAMPLE 41

(E)-1-{4-[2-(1H-indazol-3-yl)vinyl]benzoyl}-4-(morpholinocarbonyl)piperazine (Compound 41)

In a similar manner to Example 5, Compound 41 (491 mg, 58%) was obtained using (E)-4-[2-(1H-indazol-3-yl)vinyl]benzoic acid (500 mg, 1.89 mmol) obtained in Step 6 of Example 1, N-morpholinocarbonylpiperazine hydrochloride (223 mg, 0.947 mmol), 1-hydroxybenzotriazole monohydrate (333 mg, 2.46 mmol), 1-ethyl-3-(3-dimethylaminopropyl)carbodiimide hydrochloride (510 mg, 2.67 mmol) and N-methylmorpholine (1.00 mL, 9.55 mmol).

¹H-NMR (270 MHz, DMSO-d₆) δ 3.15-3.28 (m, 8H), 3.54-3.57 (m, 8H), 7.21 (t, J=7.9 Hz, 1H), 7.38 (d, J=8.4 Hz, 2H), 7.43 (t, J=7.8 Hz, 1H), 7.49-7.69 (m, 3H), 7.71 (d, J=8.4 Hz, 2H), 8.19 (brd, J=8.2 Hz, 1H), 13.2 (br, 1H). ESI-MS (m/z); 446 [M+H]⁺

EXAMPLE 42

(E)-1-{4-[2-(1H-indazol-3-yl)vinyl]benzoyl}-4-(tert-butoxycarbonylamino)piperidine (Compound 42)

In a similar manner to Example 5, Compound 42 (242 mg, 29%) was obtained using (E)-4-[2-(1H-indazol-3-yl)vinyl]benzoic acid (500 mg, 1.89 mmol) obtained in Step 6 of Example 1, 4-(tert-butoxycarbonylamino)piperidine (538 mg, 2.84 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (0.420 mL, 3.82 mmol).

¹H-NMR (270 MHz, DMSO-d₆) δ 1.14-1.16 (m, 2H), 1.37 (s, 9H), 1.61-1.98 (m, 2H), 2.88-3.31 (m, 2H), 3.51 (br, 2H), 4.29 (br, 1H), 6.88 (d, J=7.1 Hz, 1H), 7.21 (t, J=7.1 Hz, 1H), 7.37 (d, J=8.1 Hz, 2H), 7.41 (t, J=7.9 Hz, 1H), 7.66-7.70 (m, 3H), 7.77 (d, J=8.3 Hz, 2H), 8.19 (brd, J=8.1 Hz, 1H), 13.2 (br, 1H). ESI-MS (m/z); 447 [M+H]⁺

EXAMPLE 43

(E)-1-{4-[2-(1H-indazol-3-yl)vinyl]benzoyl}-4-(acetylamino)piperidine (Compound 43)

In a similar manner to Example 5, Compound 43 (283 mg, 39%) was obtained using (E)-4-[2-(1H-indazol-3-yl)vinyl]benzoic acid (500 mg, 1.89 mmol) obtained in Step 6 of Example 1, 4-(acetylamino)piperidine (404 mg, 2.84 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (0.42 mL, 3.82 mmol).

¹H-NMR (270 MHz, DMSO-d₆) δ 1.32 (brm, 2H), 1.78-1.98 (m, 2H), 1.79 (s, 3H), 3.06 (brm, 2H), 3.79-3.82 (m, 2H), 4.15 (m, 1H), 7.18-7.25 (m, 1H), 7.37-7.41 (m, 3H), 7.48-7.66 (m, 3H), 7.76-7.86 (m, 3H), 8.19 (brd, J=8.1 Hz, 1H), 13.2 (br, 1H). ESI-MS (m/z); 389 [M+H]⁺

EXAMPLE 44

(E)-1-{4-[2-(1H-indazol-3-yl)vinyl]benzoyl}-4-(isonicotinoyl)piperazine (Compound 44)

In a similar manner to Example 5, Compound 44 (108 mg, 13%) was obtained using (E)-4-[2-(1H-indazol-3-yl)vinyl]benzoic acid (477 mg, 1.81 mmol) obtained in Step 6 of Example 1, 4-(isonicotinoyl)piperazine dihydrochloride (617 mg, 2.71 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (1.00 mL, 9.55 mmol).

¹H-NMR (270 MHz, DMSO-d₆) δ 3.36-3.70 (m, 8H), 7.22 (t, 1H, J=7.4 Hz), 7.38-7.67 (m, 8H), 7.80 (d, 2H, J=8.1 Hz), 8.20 (d, 1H, J=8.2 Hz), 8.68 (d, 2H, J=5.8 Hz), 13.2 (br, 1H). ESI-MS (m/z); 438 [M+H]⁺

EXAMPLE 45

(E)-1-{4-[2-(1H-indazol-3-yl)vinyl]benzoyl}-4-(nicotinoyl)piperazine (Compound 45)

In a similar manner to Example 5, Compound 45 (58.6 mg, 7%) was obtained using (E)-4-[2-(1H-indazol-3-yl)vinyl]benzoic acid (500 mg, 1.89 mmol) obtained in Step 6 of Example 1, 4-(nicotinoyl)piperazine hydrochloride (617 mg, 2.71 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (1.00 mL, 9.55 mmol).

¹H-NMR (270 MHz, DMSO-d₆) δ 3.33-3.58 (m, 8H), 7.22 (t, J=7.9 Hz, 1H), 7.37-7.68 (m, 7H), 7.83 (dd, J=8.1, 0.9 Hz, 3H), 8.20 (d, J=8.1 Hz, 1H), 8.68 (dd, J=4.9, 1.5 Hz, 2H), 13.2 (br, 1H). ESI-MS (m/z); 438 [M+H]⁺

EXAMPLE 46

(E)-1-{4-[2-(1H-indazol-3-yl)-vinyl]benzoyl}-4-benzoylpiperazine (Compound 46)

In a similar manner to Example 5, Compound 46 (168 mg, 20%) was obtained using (E)-4-[2-(1H-indazol-3-yl)vinyl]benzoic acid (500 mg, 1.89 mmol) obtained in Step 6 of Example 1, 4-benzoylpiperazine hydrochloride (643 mg, 2.71 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (1.00 mL, 9.55 mmol).

$^1$H-NMR (270 MHz, DMSO-$d_6$) δ 3.36-3.70 (m, 8H), 7.22 (t, J=7.1 Hz, 1H), 7.38-7.68 (m, 11H), 7.79 (d, J=8.1 Hz, 2H), 8.20 (d, J=8.2 Hz, 1H), 13.2 (br, 1H). ESI-MS (m/z); 437 [M+H]$^+$

EXAMPLE 47

(E)-1-{4-[2-(1H-indazol-3-yl)vinyl]benzoyl}-4-(methanesulfonyl)piperazine (Compound 47)

In a similar manner to Example 5, Compound 47 (100 mg, 13%) was obtained using (E)-4-[2-(1H-indazol-3-yl)vinyl]benzoic acid (500 mg, 1.89 mmol) obtained in Step 6 of Example 1, 4-(methanesulfonyl)piperazine hydrochloride (570 mg, 2.71 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (0.65 mL, 5.91 mmol).

$^1$H-NMR (270 MHz, DMSO-$d_6$) δ 2.92 (s, 3H), 3.15-3.25 (m, 6H), 3.51-3.65 (m, 2H), 7.22 (t, J=7.9 Hz, 1H), 7.40 (t, J=8.3 Hz, 1H), 7.46 (d, J=7.9 Hz, 2H), 7.52-7.69 (m, 3H), 7.81 (d, J=7.9 Hz, 2H), 8.21 (d, J=7.8 Hz, 1H), 13.2 (br, 1H). ESI-MS (m/z); 411 [M+H]$^+$

EXAMPLE 48

(E)-1-{4-[2-(1H-indazol-3-yl)vinyl]benzoyl}-4-[(1H-imidazol-1-yl)carbonyl]piperazine (Compound 48)

A solution of dihydrochloride of Compound 18 (400 mg, 1.09 mmol) in THF (20 mL) was added with ethylamine (177 mg, 2.18 mmol) and 1,1'-carbonyldiimidazole (352 mg, 2.18 mmol), followed by stirring at room temperature for 1.5 hours. The reaction mixture was added with water and was extracted with ethyl acetate. The organic layer was washed with saturated brine, and was dried over anhydrous magnesium sulfate. The solvent was evaporated and the residue was purified by preparative thin-layer chromatography (chloroform/acetone=1/1) to obtain Compound 48 (350 mg, 44%).

$^1$H-NMR (270 MHz, DMSO-$d_6$) δ 3.59 (br, 8H), 7.04 (d, J=2.1 Hz, 1H), 7.21 (d, J=8.2 Hz, 1H), 7.40 (t, J=8.2 Hz, 1H), 7.46 (d, J=8.2 Hz, 2H), 7.48 (d, J=2.1 Hz, 1H), 7.54 (d, J=16.6 Hz, 1H), 7.55 (d, J=8.2 Hz, 1H), 7.64 (d, J=16.6 Hz, 1H), 7.80 (d, J=8.2 Hz, 2H), 8.05 (d, J=8.2 Hz, 1H), 8.20 (d, J=8.2 Hz, 1H), 13.2 (br, 1H). ESI-MS (m/z); 427 [M+H]$^+$

EXAMPLE 49

(E)-1-{4-[2-(1H-indazol-3-yl)vinyl]benzoyl}-4-(ethoxycarbonyl)piperidine (Compound 49)

In a similar manner to Example 5, Compound 49 (3.04 g, 59%) was obtained using (E)-4-[2-(1H-indazol-3-yl)vinyl]benzoic acid (3.38 g, 12.8 mmol) obtained in Step 6 of Example 1, ethyl isonipecotate (2.4 mL, 15.4 mmol), 1-hydroxybenzotriazole monohydrate (2.94 g, 19.2 mmol), 1-ethyl-3-(3-dimethylaminopropyl)carbodiimide hydrochloride (3.68 g, 19.2 mmol) and N-methylmorpholine (2.8 mL, 25.6 mmol).

$^1$H-NMR (300 MHz, DMSO-$d_6$) δ 1.02 (dd, J=1.83, 6.1 Hz, 2H), 1.18 (t, J=7.2 Hz, 3H), 1.47-1.58 (m, 2H), 1.85 (brs, 2H), 2.59-2.67 (m, 1H), 3.03 (brs, 2H), 4.07 (t, J=7.2 Hz, 2H), 7.18-7.27 (m, 1H), 7.36-7.41 (m, 3H), 7.48-7.59 (m, 2H), 7.63-7.66 (m, 1H), 7.77 (d, J=8.3 Hz, 2H), 8.20 (d, J=8.3 Hz, 1H), 13.2 (s, 1H). ESI-MS (m/z); 404 [M+H]$^+$

EXAMPLE 50

(E)-1-{4-[2-(1H-indazol-3-yl)vinyl]benzoyl}-4-carboxypiperidine (Compound 50)

Compound 49 (1.0 g, 2.80 mmol) was dissolved in ethanol (40 mL), then the solution was added with 2 mol/L aqueous sodium hydroxide solution (15.0 mL) at 0° C., and was warmed to room temperature. After stirring for 6 hours, the reaction mixture was neutralized with 2 mol/L hydrochloric acid and was extracted with ethyl acetate. The organic layer was dried over anhydrous sodium sulfate and was concentrated. The residue was recrystallized from ethyl acetate and methanol to obtain Compound 50 (654 mg, 70%).

$^1$H-NMR (300 MHz, DMSO-$d_6$) δ 1.44-1.53 (m, 2H), 1.85 (brm, 2H), 2.71 (brs, 2H), 3.04-3.34 (brm, 3H), 4.30 (brm, 1H), 7.20 (m, 1H), 7.40 (dd, J=3.3, 1.4 Hz, 2H), 7.50-7.65 (m, 4H), 7.77 (d, J=8.3 Hz, 2H), 8.19 (d, J=8.1 Hz, 1H), 13.2 (s, 1H). ESI-MS (m/z); 376 [M+H]$^+$

EXAMPLE 51

(E)-1-{4-[2-(1H-indazol-3-yl)vinyl]benzoyl}-4-(morpholinocarbonyl)piperidine (Compound 51)

In a similar manner to Example 5, Compound 51 (101 mg, 34%) was obtained using Compound 50 (250 mg, 0.67 mmol) morpholine (0.087 mL, 0.99 mmol), 1-hydroxybenzotriazole monohydrate (133 mg, 0.870 mmol) and 1-ethyl-3-(3-dimethylaminopropyl)carbodiimide hydrochloride (178 mg, 0.93 mmol).

$^1$H-NMR (300 MHz, DMSO-$d_6$) δ 1.45-1.65 (m, 4H), 2.93-3.32 (brm, 3H), 3.43-4.03 (brm, 10H), 7.18-7.23 (m, 1H), 7.37-7.41 (m, 2H), 7.50-7.65 (m, 4H), 7.76 (d, J=8.1 Hz, 2H), 8.20 (d, J=8.1 Hz, 1H), 13.20 (s, 1H), 7.79 (d, J=8.4 Hz, 2H), 8.04 (d, J=8.1 Hz, 1H). ESI-MS (m/z); 445 [M+H]$^+$

EXAMPLE 52 methyl {(E)-4-[2-(1H-indazol-3-yl)vinyl]benzoylamino}acetate (Compound 52)

In a similar manner to Example 5, Compound 52 (1.65 g, 87%) was obtained using (E)-4-[2-(1H-indazol-3-yl)vinyl]benzoic acid (1.50 g, 5.68 mmol) obtained in Step 6 of Example 1, glycine methyl ester hydrochloride (856 mg, 6.82 mmol), 1-hydroxybenzotriazole monohydrate (1.30 g, 8.52 mmol), 1-ethyl-3-(3-dimethylaminopropyl)carbodiimide hydrochloride (1.63 g, 8.52 mmol) and N-methylmorpholine (1.87 mL, 17.0 mmol).

$^1$H-NMR (300 MHz, DMSO-$d_6$) δ 3.62 (s, 3H), 3.90 (dd, J=17.8, 5.7 Hz, 2H), 7.21 (m, 1H), 7.40 (m, 1H), 7.54 (m, 1H), 7.67 (m, 1H), 7.81 (d, J=8.3 Hz, 2H), 7.90 (d, J=8.3 Hz, 2H), 8.20 (d, J=7.9 Hz, 1H), 8.35 (m, 1H), 8.79 (m, 1H), 13.2 (s, 1H). ESI-MS (m/z); 336 [M+H]$^+$

EXAMPLE 53

{(E)-4-[2-(1H-indazol-3-yl)vinyl]benzoylamino}acetic acid (Compound 53)

Compound 52 (1.65 g, 4.93 mmol) was dissolved in THF (30 mL), then the solution was added with 2 mol/L aqueous sodium hydroxide solution (15.0 mL) at 0° C., followed by stirring at 70° C. for 1 hour. The reaction mixture was neutralized with 2 mol/L hydrochloric acid, then was extracted with ethyl acetate. The organic layer was dried over anhydrous sodium sulfate, and was concentrated. The residue was recrystallized from ethyl acetate and methanol to obtain Compound 53 (662 mg, 42%).

$^1$H-NMR (300 MHz, DMSO-$d_6$) δ 3.90 (d, J=5.8 Hz, 2H), 7.21 (m, 1H), 7.39 (m, 1H), 7.51-7.71 (m, 3H), 7.83 (dd, J=21.8, 8.4 Hz, 4H), 8.21 (d, J=8.2 Hz, 1H), 8.76 (m, 1H), 13.2 (brs, 1H). ESI-MS (m/z); 322 [M+H]$^+$

EXAMPLE 54

(E)-4-acetyl-1-{4-[2-(1H-indazol-3-yl)vinyl]-2-methoxybenzoyl}piperazine (Compound 54)

In a similar manner to Example 5, Compound 54 (108 mg, 14%) was obtained using (E)-4-[2-(1H-indazol73-yl)vinyl]-2-methoxybenzoic acid (500 mg, 1.70 mmol), N-acetylpiperazine (327 mg, 2.55 mmol), 1-hydroxybenzotriazole monohydrate (300 mg, 2.22 mmol), 1-ethyl-3-(3-dimethylaminopropyl)carbodiimide hydrochloride (456 mg, 2.40 mmol) and N-methylmorpholine (0.40 mL, 3.41 mmol).

$^1$H-NMR (270 MHz, DMSO-$d_6$) δ 1.99 (s, 3H), 3.13-3.66 (brm, 8H), 3.90 (s, 3H), 7.22 (t, J=8.1 Hz, 2H), 7.34-7.43 (m, 2H), 7.48 (d, J=16.5 Hz, 1H), 7.51-7.57 (m, 2H), 7.66 (d, J=16.5 Hz, 1H), 8.21 (d, J=8.2 Hz, 1H), 13.2 (brs, 1H). ESI-MS (m/z); 405 [M+H]$^+$

EXAMPLE 55

(E)-4-cyclopropanecarbonyl-1-{4-[2-(1H-indazol-3-yl)vinyl]benzoyl}piperazine (Compound 55)

In a similar manner to Example 5, Compound 55 (343 mg, 87%) was obtained using dihydrochloride of Compound 18 (400 mg, 1.09 mmol), cyclopropylcarboxylic acid (0.078 mL, 0.987 mmol), 1-hydroxybenzotriazole monohydrate (173 mg, 1.28 mmol), 1-ethyl-3-(3-dimethylaminopropyl)carbodiimide hydrochloride (265 mg, 1.38 mmol) and N-methylmorpholine (0.20 mL, 1.82 mmol).

$^1$H-NMR (270 MHz, DMSO-$d_6$) δ 1.00 (d, J=6.6 Hz, 4H), 2.81 (m, 1H), 3.54-3.98 (m, 8H), 7.21 (dt, J=7.9, 1.1 Hz, 1H), 7.36-7.67 (m, 6H), 7.79 (d, J=8.2 Hz, 2H), 8.20 (d, J=8.2 Hz, 1H), 13.2 (br, 1H). ESI-MS (m/z); 401 [M+H]$^+$

EXAMPLE 56

(E)-4-isobutyryl-1-{4-[2-(1H-indazol-3-yl)vinyl] benzoyl}piperazine (Compound 56)

In a similar manner to Example 5, Compound 56 (201 mg, 51%) was obtained using dihydrochloride of Compound 18 (400 mg, 1.09 mmol), 2-methylpropionic acid (0.092 mL, 0.987 mmol), 1-hydroxybenzotriazole monohydrate (173 mg, 1.28 mmol), 1-ethyl-3-(3-dimethylaminopropyl)carbodiimide hydrochloride (265 mg, 1.38 mmol) and N-methylmorpholine (0.40 mL, 3.64 mmol).

$^1$H-NMR (270 MHz, DMSO-$d_6$) δ 0.68-0.78 (m, 6H), 3.33-3.79 (m, 9H), 7.21 (dt, J=8.1, 1.5 Hz, 1H), 7.39 (dt, J=8.4, 1.5 Hz, 1H), 7.45 (d, J=8.3 Hz, 2H), 7.51-7.67 (m, 3H), 7.79 (d, J=8.2 Hz, 2H), 8.20 (d, J=8.2 Hz, 1H), 13.2 (br, 1H). ESI-MS (m/z); 403 [M+H]$^+$

EXAMPLE 57

(E)-4-(2-thiophencarbonyl)-1-{4-[2-(1H-indazol-3-yl)vinyl]benzoyl}piperazine (Compound 57)

In a similar manner to Example 5, Compound 57 (382 mg, 88%) was obtained using dihydrochloride of Compound 18 (400 mg, 1.09 mmol), 2-thiophenecarboxylic acid (127 mg, 0.987 mmol), 1-hydroxybenzotriazole monohydrate (173 mg, 1.28 mmol), 1-ethyl-3-(3-dimethylaminopropyl)carbodiimide hydrochloride (265 mg, 1.38 mmol) and N-methylmorpholine (0.400 mL, 3.64 mmol).

$^1$H-NMR (270 MHz, DMSO-$d_6$) δ 3.38-3.98 (m, 8H), 7.13 (dt, J=8.6, 2.3 Hz, 1H), 7.21 (t, J=7.4 Hz, 1H), 7.37-7.68 (m, 7H), 7.78 (t, J=8.3 Hz, 3H), 8.20 (d, J=8.3 Hz, 1H), 13.2 (br, 1H). ESI-MS (m/z); 443 [M+H]$^+$

EXAMPLE 58

(E)-4-(3-thiophenecarbonyl)-1-{4-[2-(1H-indazol-3-yl)vinyl-]benzoyl}piperazine (Compound 58)

In a similar manner to Example 5, Compound 58 (356 mg, 82%) was obtained using dihydrochloride of Compound 18 (400 mg, 1.09 mmol), 3-thiophenecarboxylic acid (127 mg, 0.987 mmol), 1-hydroxybenzotriazole monohydrate (173 mg, 1.28 mmol), 1-ethyl-3-(3-dimethylaminopropyl)carbodiimide hydrochloride (265 mg, 1.38 mmol) and N-methylmorpholine (0.40 mL, 3.64 mmol).

$^1$H-NMR (270 MHz, DMSO-$d_6$) δ 3.38-3.98 (m, 8H), 7.13 (dt, J=8.6, 2.3 Hz, 1H), 7.21 (t, J=7.4 Hz, 1H), 7.37-7.68 (m, 7H), 7.67-7.88 (m, 3H), 8.20 (d, J=8.2 Hz, 1H), 13.2 (br, 1H). ESI-MS (m/z); 443 [M+H]$^+$

EXAMPLE 59

(E)-4-ethylaminocarbonyl-1-{4-[2-(1H-indazol-3-yl)vinyl]benzoyl}piperazine (Compound 59)

A solution of dihydrochloride of Compound 18 (400 mg, 1.09 mmol) in THF (20 mL) was added with triethylamine (0.42 mL, 3.01 mmol) and ethylisodyanate (117 mg, 1.65 mmol), followed by stirring at room temperature for 3 hours. The reaction mixture was added with water, and deposited crystal was collected by filtration and was dried to obtain Compound 59 (218 mg, 55%).

$^1$H-NMR (270 MHz, DMSO-$d_6$) δ 1.00 (t, J=7.1 Hz, 3H), 3.00-3.07 (m, 2H), 3.33-3.44 (m, 8H), 6.55 (t, J=5.3 Hz, 1H), 7.21 (t, J=7.8 Hz, 1H), 7.38 (d, J=8.4 Hz, 1H), 7.43 (t, J=8.3 Hz, 2H), 7.50-7.67 (m, 3H), 7.78 (d, J=8.3 Hz, 2H), 8.20 (d, J=8.1 Hz, 1H), 13.2 (br, 1H). ESI-MS (m/z); 404 [M+H]$^+$

EXAMPLE 60

(E)-4-butyryl-1-{4-[2-(1H-indazol-3-yl)vinyl]benzoyl}piperazine (Compound 60)

In a similar manner to Example 5, Compound 60 (221 mg, 61%) was obtained using dihydrochloride of Compound 18 (400 mg, 1.09 mmol), n-butanoic acid (0.082 mL, 0.896 mmol), 1-hydroxybenzotriazole monohydrate (173 mg, 1.28 mmol), 1-ethyl-3-(3-dimethylaminopropyl)carbodiimide hydrochloride (265 mg, 1.38 mmol) and N-methylmorpholine (0.40 mL, 3.64 mmol).

¹H-NMR (270 MHz, DMSO-$d_6$) δ 0.88 (t, J=7.4 Hz, 3H), 1.50 (q, J=7.4 Hz, 2H), 2.28 (t, J=7.3 Hz, 2H), 3.81-3.98 (m, 8H), 7.21 (t, J=7.4 Hz, 1H), 7.38 (d, J=8.2 Hz, 1H), 7.44 (d, J=8.3 Hz, 2H), 7.53-7.67 (m, 3H), 7.78 (d, J=8.2 Hz, 2H), 8.20 (d, J=8.2 Hz, 1H), 13.2 (br, 1H). ESI-MS (m/z); 403 [M+H]$^+$

EXAMPLE 61

(E)-4-aminoacetyl-1-{4-[2-(1H-indazol-3-yl)vinyl]benzoyl}piperazine hydrochloride (Compound 61)

In a similar manner to Example 5, (E)-4-(tert-butoxycarbonylamino)acetyl-1-{4-[2-(1H-indazol-3-yl)vinyl]benzoyl}piperazine was obtained using dihydrochloride of Compound 18 (800 mg, 2.18 mmol), N-(tert-butoxycarbonyl)glycine (314 mg, 1.79 mmol), 1-hydroxybenzotriazole monohydrate (315 mg, 2.56 mmol), 1-ethyl-3-(3-dimethylaminopropyl)carbodiimide hydrochloride (482 mg, 2.51 mmol) and N-methylmorpholine (0.80 mL, 7.28 mmol). In a similar manner to Example 18, (E)-4-(tert-butoxycarbonylamino)acetyl-1-{4-[2-(1H-indazol-3-yl)vinyl]benzoyl}piperazine was treated with 10% hydrogen chloride-methanol solution to obtain Compound 61 (448 mg, 64%).

¹H-NMR (270 MHz, DMSO-$d_6$) δ 3.41-3.68 (m, 8H), 3.88-3.92 (brd, J=2.9 Hz, 2H), 7.21 (t, J=7.9 Hz, 1H), 7.37-7.67 (m, 7H), 7.80 (d, J=8.3 Hz, 2H), 8.14 (brm, 1H), 8.20 (d, J=8.3 Hz, 1H). ESI-MS (m/z); 390 [M+H]$^+$

EXAMPLE 62

(E)-N-(2-oxo-2-morpholinoethyl)-4-[2-(1H-indazol-3-yl)vinyl]benzamide (Compound 62)

In a similar manner to Example 5, Compound 62 (105 mg, 36%) was obtained using Compound 53 (250 mg, 0.776 mmol), morpholine (0.098 mL, 1.12 mmol), 1-hydroxybenzotriazole monohydrate (149 mg, 0.97 mmol) and 1-ethyl-3-(3-dimethylaminopropyl)carbodiimide hydrochloride (200 mg, 1.04 mmol).

¹H-NMR (270 MHz, DMSO-$d_6$) δ 3.15-3.31 (m, 1H), 3.40-3.59 (m, 8H), 4.13 (d, J=5.7 Hz, 2H), 7.21 (t, J=7.7 Hz, 1H), 7.35-7.42 (m, 2H), 7.52-7.65 (m, 2H), 7.72 (d, J=15.2 Hz, 1H), 7.86 (dd, J=24.8, 8.4 Hz, 4H), 8.21 (d, J=8.3 Hz, 1H), 8.59 (t, J=5.9 Hz, 1H). ESI-MS (m/z); 391 [M+H]$^+$

EXAMPLE 63

(E)-N-[2-(diethylamino)ethyl]-4-[2-(1H-indazol-3-yl)vinyl]benzamide (Compound 63)

In a similar manner to Example 5, Compound 63 (3.00 g, 55%) was obtained using (E)-4-[2-(1H-indazol-3-yl)vinyl]benzoic acid (4.00 g, 15.1 mmol), N,N-diethylethylenediamine (2.60 mL, 18.2 mmol), 1-hydroxybenzotriazole monohydrate (3.00 g, 19.70 mmol), 1-ethyl-3-(3-dimethylaminopropyl)carbodiimide hydrochloride (4.10 g, 21.2 mmol) and N-methylmorpholine (3.40 mL, 30.3 mmol).

¹H-NMR (300 MHz, DMSO-$d_6$) δ 0.97 (t, J=7.5 Hz, 6H), 2.54 (m, 8H), 7.20 (m, 1H), 7.40 (m, 1H), 7.51-7.69 (m, 3H), 7.81 (dd, J=18.3, 8.3 Hz, 4H), 8.20 (d, J=8.1 Hz, 1H), 8.40 (m, 1H), 13.2 (s, 1H). ESI-MS (m/z); 363 [M+H]$^+$

EXAMPLE 64

(E)-1-{4-[2-(1H-indazol-3-yl)vinyl]benzoyl}-4-aminopiperidine (Compound 64)

The product obtained using (E)-4-[2-(1H-indazol-3-yl)vinyl]benzoic acid (500 mg, 1.89 mmol) obtained in Step 6 of Example 1, 4-(tert-butoxycarbonylamino)piperidine (538 mg, 2.84 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (0.420 mL, 3.82 mmol) in a similar manner to Example 5, was dissolved in methanol (10.0 mL), and the solution was added with 4 mol/L hydrogen chloride-methanol solution (5.0 mL), followed by heating under reflux at 60° C. for 90 minutes. The reaction mixture was concentrated under reduced pressure, the residue was extracted after adding with a saturated aqueous potassium carbonate solution and ethyl acetate. The crude product was crystallized from ethyl acetate to obtain Compound 64 (435 mg, 66%).

¹H-NMR (270 MHz, DMSO-$d_6$) δ 1.15-1.20 (m, 2H), 1.72-2.00 (m, 2H), 2.79-3.60 (m, 7H), 7.22 (dd, J=7.9, 7.9 Hz, 1H), 7.38 (d, J=8.3 Hz, 2H), 7.37-7.43 (m, 1H), 7.54 (d, J=16.9 Hz, 1H), 7.56 (d, J=7.9 Hz, 1H), 7.63 (d, J=16.9 Hz, 1H), 7.78 (d, J=8.3 Hz, 2H), 8.21 (d, J=8.3 Hz, 1H). ESI-MS (m/z); 347 [M+H]$^+$

EXAMPLE 65

(E)-4-methoxyacetyl-1-{4-[2-(1H-indazol-3-yl)vinyl]benzoyl}piperazine (Compound 65)

In a similar manner to Example 5, Compound 65 (225 mg, 62%) was obtained using dihydrochloride of Compound 18 (400 mg, 1.09 mmol), methoxyacetic acid (0.069 mL, 0.896 mmol), 1-hydroxybenzotriazole monohydrate (173 mg, 1.28 mmol), 1-ethyl-3-(3-dimethylaminopropyl)carbodiimide hydrochloride (265 mg, 1.38 mmol) and N-methylmorpholine (0.40 mL, 3.64 mmol).

¹H-NMR (270 MHz, DMSO-$d_6$) δ 3.28 (s, 3H), 3.33-3.49 (m, 8H), 4.10 (s, 2H), 7.21 (t, J=7.3 Hz, 1H), 7.38 (d, J=8.1 Hz, 1H), 7.44 (d, J=8.3 Hz, 2H), 7.51-7.67 (m, 3H), 7.79 (d, J=8.3 Hz, 2H), 8.20 (d, J=8.1 Hz, 1H), 13.2 (br, 1H). ESI-MS (m/z); 405 [M+H]$^+$

EXAMPLE 66

(E)-4-(3-methylbutyryl)-1-{4-[2-(1H-indazol-3-yl)vinyl]benzoyl}piperazine (Compound 66)

In a similar manner to Example 5, Compound 66 (207 mg, 56%) was obtained using dihydrochloride of Compound 18 (400 mg, 1.09 mmol), isovaleric acid (0.094 mL, 0.896 mmol), 1-hydroxybenzotriazole monohydrate (176 mg, 1.28 mmol), 1-ethyl-3-(3-dimethylaminopropyl)carbodiimide hydrochloride (265 mg, 1.38 mmol) and N-methylmorpholine (0.400 mL, 3.64 mmol).

¹H-NMR (270 MHz, DMSO-$d_6$) δ 0.89 (d, J=6.6 Hz, 6H), 1.93-2.03 (m, 1H), 2.21 (d, J=6.8 Hz, 2H), 3.39-3.52 (m, 8H), 7.21 (t, J=7.3 Hz, 1H), 7.38 (d, J=8.8 Hz, 1H), 7.44 (d, J=8.3 Hz, 2H), 7.51-7.67 (m, 3H), 7.79 (d, J=8.3 Hz, 2H), 8.20 (d, J=8.1 Hz, 1H), 13.2 (br, 1H). ESI-MS (m/z); 417 [M+H]$^+$

EXAMPLE 67

(E)-4-(4-methylphenylsulfonyl)-1-{4-[2-(1H-indazol-3-yl)vinyl]benzoyl}piperazine (Compound 67)

In a similar manner to Example 47, Compound 67 (210 mg, 48%) was obtained using dihydrochloride of Compound 18 (400 mg, 1.09 mmol), triethylamine (0.420 mL, 3.01 mmol) and p-toluenesulfonyl chloride (376 mg, 1.97 mmol).

¹H-NMR (270 MHz, DMSO-$d_6$) δ 2.42 (s, 3H), 2.94-3.26 (m, 4H), 3.39-3.57 (m, 4H), 7.20 (t, J=7.9 Hz, 1H), 7.35-7.64 (m, 10H), 7.74 (d, J=8.3 Hz, 2H), 8.18 (d, J=8.3 Hz, 1H), 13.2 (br, 1H). ESI-MS (m/z); 487 [M+H]$^+$

EXAMPLE 68

(E)-4-(2-methyl-2-hydroxypropionyl)-1-{4-[2-(1H-indazol-3-yl)vinyl]benzoyl}piperazine (Compound 68)

In a similar manner to Example 5, Compound 68 (223 mg, 60%) was obtained using dihydrochloride of Compound 18 (400 mg, 1.09 mmol), α-hydroxyisobutyric acid (93.2 mg, 0.896 mmol), 1-hydroxybenzotriazole monohydrate (176 mg, 1.28 mmol), 1-ethyl-3-(3-dimethylaminopropyl)carbodiimide hydrochloride (265 mg, 1.38 mmol) and N-methylmorpholine (0.40 mL, 3.64 mmol).
$^1$H-NMR (270 MHz, DMSO-$d_6$) δ 1.52 (s, 6H), 3.71-3.99 (m, 8H), 5.65 (br, 1H), 7.41 (t, J=7.3 Hz, 1H), 7.58 (d, J=8.2 Hz, 1H), 7.65 (d, J=8.4 Hz, 2H), 7.71-7.87 (m, 3H), 7.98 (d, J=8.2 Hz, 2H), 8.40 (d, J=8.1 Hz, 1H), 13.4 (br, 1H). ESI-MS (m/z); 419 [M+H]$^+$

EXAMPLE 69

(E)-4-acetyl-1-{2-chloro-4-[2-(1H-indazol-3-yl)vinyl]benzoyl}piperazine (Compound 69)

In a similar manner to Example 5, Compound 69 (42 mg, 30%) was obtained using (E)-4-[2-(1H-indazol-3-yl)vinyl]-2-chlorobenzoic acid (100 mg, 0.34 mmol), N-acetylpiperazine (64 mg, 0.50 mmol), 1-hydroxybenzotriazole monohydrate (67 mg, 0.44 mmol), 1-ethyl-3-(3-dimethylaminopropyl)carbodiimide hydrochloride (90 mg, 0.47 mmol) and N-methylmorpholine (0.40 mL, 3.41 mmol).
$^1$H-NMR (270 MHz, DMSO-$d_6$) δ 2.04 (s, 3H), 3.12-3.91 (br, 8H), 6.71-7.69 (m, 8H), 7.99 (d, J=8.1 Hz, 1H). ESI-MS (m/z); 409 [M+H]$^+$

EXAMPLE 70

(E)-4-[2-(1H-indazol-3-yl)vinyl]-N-(methylcarbamoylmethyl)benzamide (Compound 70)

In a similar manner to Example 5, Compound 70 (63 mg, 24%) was obtained using Compound 53 (300 mg, 0.932 mmol), methylamine hydrochloride (65.0 mg, 0.960 mmol), 1-hydroxybenzotriazole monohydrate (159 mg, 1.04 mmol), 1-ethyl-3-(3-dimethylaminopropyl)carbodiimide hydrochloride (215 mg, 1.12 mmol) and N-methylmorpholine (0.220 mL, 2.00 mmol).
$^1$H-NMR (270 MHz, DMSO-$d_6$) δ 2.59 (d, J=4.6 Hz, 3H), 3.19-3.45 (m, 1H), 3.82 (d, J=5.9 Hz, 2H), 7.20 (m, 1H), 7.39 (m, 1H), 7.51-7.71 (m, 3H), 7.84 (dd, J=27.8, 8.4 Hz, 4H), 8.20 (d, J=8.1 Hz, 1H), 8.73 (m, 1H), 13.2 (s, 1H). ESI-MS (m/z); 335 [M+H]$^+$

EXAMPLE 71

(E)-4-(N-acetylamino)acetyl-1-{4-[2-(1H-indazol-3-yl)vinyl]benzoyl}piperazine (Compound 71)

In a similar manner to Example 5, Compound 71 (320 mg, 83%) was obtained using dihydrochloride of Compound 18 (400 mg, 1.09 mmol), N-acetylglycine (105 mg, 0.896 mmol), 1-hydroxybenzotriazole monohydrate (175 mg, 1.28 mmol), 1-ethyl-3-(3-dimethylaminopropyl)carbodiimide hydrochloride (265 mg, 1.38 mmol) and N-methylmorpholine (0.400 mL, 3.64 mmol).
$^1$H-NMR (270 MHz, DMSO-$d_6$) δ 1.98 (s, 3H), 3.42-3.58 (m, 8H), 3.94-3.98 (m, 2H), 7.21 (t, J=7.0 Hz, 1H), 7.40 (d, J=7.0 Hz, 1H), 7.45 (d, J=8.3 Hz, 2H), 7.51-7.67 (m, 3H), 7.79 (d, J=8.3 Hz, 2H), 7.97 (t, J=5.5 Hz, 1H), 8.20 (d, 7.9 Hz, 1H), 13.2 (br, 1H). ESI-MS (m/z); 432 [M+H]$^+$

EXAMPLE 72

(E)-4-(3-hydroxy-2,2-dimethylpropionyl)-1-{4-[2-(1H-indazol-3-yl)vinyl]benzoyl}piperazine (Compound 72)

In a similar manner to Example 5, Compound 72 (40 mg, 10%) was obtained using dihydrochloride of Compound 18 (400 mg, 1.09 mmol), 3-hydroxy-2,2-dimethylpropionic acid (106 mg, 0.896 mmol), 1-hydroxybenzotriazole monohydrate (176 mg, 1.28 mmol), 1-ethyl-3-(3-dimethylaminopropyl)carbodiimide hydrochloride (265 mg, 1.38 mmol) and N-methylmorpholine (0.40 mL, 3.64 mmol).
$^1$H-NMR (270 MHz, DMSO-$d_6$) δ 1.15 (s, 6H), 3.41-3.42 (m, 2H), 3.45-3.65 (m, 8H), 4.58 (t, J=5.9 Hz, 1H), 7.21 (t, J=7.9 Hz, 1H), 7.38 (d, J=7.5 Hz, 1H), 7.44 (d, J=8.4 Hz, 2H), 7.51-7.67 (m, 3H), 7.79 (d, J=8.3 Hz, 2H), 8.20 (d, J=8.1 Hz, 1H), 13.2 (br, 1H). ESI-MS (m/z); 433 [M+H]$^+$

EXAMPLE 73

(E)-4-acetyl-1-{2-methyl-4-[2-(1H-indazol-3-yl)vinyl]benzoyl}piperazine (Compound 73)

In a similar manner to Example 5, Compound 73 (37 mg, 16%) was obtained using (E)-4-[2-(1H-indazol-3-yl)vinyl]-2-methylbenzoic acid (174 mg, 0.60 mmol), N-acetylpiperazine (114 mg, 0.892 mmol), 1-hydroxybenzotriazole monohydrate (118 mg, 0.873 mmol), 1-ethyl-3-(3-dimethylaminopropyl)carbodiimide hydrochloride (160 mg, 0.835 mmol) and N-methylmorpholine (0.40 mL, 3.41 mmol).
$^1$H-NMR (270 MHz, CDCl$_3$) δ 2.17 (s, 3H), 2.36 (s, 3H), 3.19-3.49 (br, 4H), 3.57-3.85 (br, 4H), 6.86-7.52 (m, 8H), 8.04 (d, J=8.1 Hz, 1H). ESI-MS (m/z); 389 [M+H]$^+$

EXAMPLE 74

(E)-4-hydroxyacetyl-1-{4-[2-(1H-indazol-3-yl)vinyl]benzoyl}piperazine hydrochloride (Compound 74)

In a similar manner to Example 5, a free base of Compound 74 was obtained using dihydrochloride of Compound 18 (400 mg, 1.09 mmol), glycolic acid (68.0 mg, 0.896 mmol), 1-hydroxybenzotriazole monohydrate (178 mg, 1.29 mmol), 1-ethyl-3-(3-dimethylaminopropyl)carbodiimide hydrochloride (265 mg, 1.38 mmol) and N-methylmorpholine (0.40 mL, 3.64 mmol), and then the free base of Compound 74 was dissolved in 1,4-dioxane (2.0 mL), and the solution was added with 4 moL/L hydrogen chloride-1,4-dioxane solution (2.0 mL), followed by stirring at room temperature for 30 minutes. The precipitate in the reaction mixture was filtered to obtain Compound 74 (200 mg, 52%).
$^1$H-NMR (270 MHz, DMSO-$d_6$) δ 3.41-3.52 (m, 4H), 3.55-3.65 (m, 4H), 4.10 (s, 2H), 7.20 (t, J=7.0 Hz, 1H), 7.38 (d, J=8.4 Hz, 1H), 7.43 (d, J=8.4 Hz, 2H), 7.46-7.66 (m, 3H), 7.78 (d, J=8.4 Hz, 2H), 8.20 (d, J=8.4 Hz, 1H). ESI-MS (m/z); 391 [M+H]$^+$

EXAMPLE 75

(E)-4-methoxycarbonyl-1-{4-[2-(1H-indazol-3-yl)vinyl]benzoyl}piperazine hydrochloride (Compound 75)

In a similar manner to Example 5, Compound 75 (1.00 g, 78%) was obtained using (E)-4-[2-(1H-indazol-3-yl)vinyl]benzoic acid (1.00 g, 2.97 mmol) obtained in Step 6 of Example 1, N-methoxycarbonylpiperazine (970 mg, 4.47 mmol), 1-hydroxybenzotriazole monohydrate (520 mg, 3.85 mmol), 1-ethyl-3-(3-dimethylaminopropyl)carbodiimide hydrochloride (800 mg, 4.17 mmol) and N-methylmorpholine (1.30 mL, 11.8 mmol).

$^1$H-NMR (270 MHz, DMSO-$d_6$) δ 3.41-3.52 (m, 4H), 3.61 (s, 3H), 3.78-4.00 (m, 4H), 7.21 (t, J=7.8 Hz, 1H), 7.39 (t, J=7.6 Hz, 1H), 7.44 (d, J=8.4 Hz, 2H), 7.53 (d, J=16.1 Hz, 1H), 7.56 (d, J=8.4 Hz, 1H), 7.63 (d, J=16.1 Hz, 1H), 7.78 (d, J=8.4 Hz, 2H), 8.20 (d, J=8.3 Hz, 1H). ESI-MS (m/z); 391 [M+H]$^+$

EXAMPLE 76

(E)-4-{4-[2-(1H-indazol-3-yl)vinyl]benzoyl}thiomorpholine hydrochloride (Compound 76)

In a similar manner to Example 5, a free base of Compound 76 was obtained using (E)-4-[2-(1H-indazol-3-yl)vinyl]benzoic acid (500 mg, 1.89 mmol) obtained in Step 6 of Example 1, thiomorpholine (0.307 mL, 3.05 mmol), 1-hydroxybenzotriazole monohydrate (333 mg, 2.46 mmol), 1-ethyl-3-(3-dimethylaminopropyl)carbodiimide hydrochloride (510 mg, 2.67 mmol) and N-methylmorpholine (1.00 mL, 9.55 mmol), and then the free base of Compound 76 was dissolved in 1,4-dioxane (2.0 mL), and the solution was added with 4 mol/L hydrogen chloride-1,4-dioxane solution (2.0 mL), followed by stirring at room temperature for 30 minutes. The precipitate in the reaction mixture was filtered to obtain Compound 76 (443 mg, 57%).

$^1$H-NMR (270 MHz, DMSO-$d_6$) δ 2.55-2.74 (m, 4H), 3.48-3.71 (m, 4H), 7.20 (t, J=8.0 Hz, 1H), 7.39 (t, J=7.7 Hz, 1H), 7.44 (d, J=8.5 Hz, 2H), 7.53 (d, J=16.3 Hz, 1H), 7.56 (d, J=8.4 Hz, 1H), 7.63 (d, J=16.3 Hz, 1H), 7.77 (d, J=8.4 Hz, 2H), 8.19 (d, J=8.2 Hz, 1H). ESI-MS (m/z); 350 [M+H]$^+$

EXAMPLE 77

(E)-4-(1-methylcyclopropanecarbonyl)-1-{4-[2-(1H-indazol-3-yl)vinyl]benzoyl}piperazine (Compound 77)

In a similar manner to Example 5, Compound 77 (311 mg, 67%) was obtained using dihydrochloride of Compound 18 (400 mg, 1.09 mmol), 1-methylcyclopropanecarboxylic acid (0.091 mL, 0.896 mmol), 1-hydroxybenzotriazole monohydrate (176 mg, 1.28 mmol), 1-ethyl-3-(3-dimethylaminopropyl)carbodiimide hydrochloride (265 mg, 1.38 mmol) and N-methylmorpholine (0.40 mL, 3.64 mmol).

$^1$H-NMR (270 MHz, DMSO-$d_6$) δ 0.48-0.57 (m, 2H), 0.80-0.84 (m, 2H), 1.24 (s, 3H), 3.48-3.71 (m, 8H), 7.23 (t, J=7.1 Hz, 1H), 7.41 (t, J=8.2 Hz, 1H), 7.47 (d, J=8.4 Hz, 2H), 7.53 (d, J=16.1 Hz, 1H), 7.58 (d, J=8.4 Hz, 1H), 7.67 (d, J=16.3 Hz, 1H), 7.81 (d, J=8.4 Hz, 2H), 8.22 (d, J=8.1 Hz, 1H), 13.2 (br, 1H). ESI-MS (m/z); 415 [M+H]$^+$

EXAMPLE 78

(E)-4-(3,3-dimethylbutyryl)-1-{4-[2-(1H-indazol-3-yl)vinyl]benzoyl}piperazine (Compound 78)

In a similar manner to Example 5, Compound 78 (201 mg, 52%) was obtained using dihydrochloride of Compound 18 (400 mg, 1.09 mmol), tert-butylacetic acid (0.115 mL, 0.896 mmol), 1-hydroxybenzotriazole monohydrate (176 mg, 1.28 mmol), 1-ethyl-3-(3-dimethylaminopropyl)carbodiimide hydrochloride (265 mg, 1.38 mmol) and N-methylmorpholine (0.400 mL, 3.64 mmol).

$^1$H-NMR (270 MHz, DMSO-$d_6$) δ 0.98 (s, 9H), 2.25 (brs, 2H), 3.41-3.54 (m, 8H), 7.21 (t, J=7.7 Hz, 1H), 7.38 (t, J=8.4 Hz, 1H), 7.44 (d, J=8.2 Hz, 2H), 7.51 (d, J=16.2 Hz, 1H), 7.57 (d, J=8.3 Hz, 1H), 7.67 (d, J=16.2 Hz, 1H), 7.79 (d, J=8.2 Hz, 2H), 8.20 (d, J=8.2 Hz, 1H), 13.2 (br, 1H). ESI-MS (m/z); 431 [M+H]$^+$

EXAMPLE 79

(E)-N-[2-(ethoxycarbonyl)ethyl]-4-[2-(1H-indazol-3-yl)vinyl]benzamide (Compound 79)

In a similar manner to Example 5, Compound 79 (123 mg, 6%) was obtained using (E)-4-[2-(1H-indazol-3-yl)vinyl]benzoic acid (1.50 g, 5.68 mmol) obtained in Step 6 of Example 1, β-alanine ethyl ester hydrochloride (1.05 g, 6.81 mmol), 1-hydroxybenzotriazole monohydrate (1.30 g, 8.52 mmol), 1-ethyl-3-(3-dimethylaminopropyl)carbodiimide hydrochloride (1.63 g, 8.52 mmol) and N-methylmorpholine (1.87 mL, 17.0 mmol).

$^1$H-NMR (270 MHz, DMSO-$d_6$) δ 1.17 (t, J=7.1 Hz, 3H), 2.58 (t, J=7.1 Hz, 2H), 3.39-3.53 (m, 2H), 4.0 (q, J=7.1 Hz, 2H), 7.23-7.17 (m, 1H), 7.36-7.42 (m, 1H), 7.49-7.72 (m, 3H), 7.79 (dd, J=16.3, 8.4 Hz, 4H), 8.19 (d, J=8.1 Hz, 1H), 8.55 (m, 1H), 13.2 (s, 1H). ESI-MS (m/z); 364 [M+H]$^+$

EXAMPLE 80

(E)-N-methyl-1-{4-[2-(1H-indazol-3-yl)vinyl]benzoyl}piperidine-4-carboxamide (Compound 80)

In a similar manner to Example 5, Compound 80 (22 mg, 7%) was obtained using Compound 50 (300 mg, 0.80 mmol), methylamine hydrochloride (64.8 mg, 0.96 mmol), 1-hydroxybenzotriazole monohydrate (184 mg, 1.2 mmol), 1-ethyl-3-(3-dimethylaminopropyl)carbodiimide hydrochloride (230 mg, 1.2 mmol) and N-methylmorpholine (0.264 mL, 2.4 mmol).

$^1$H-NMR (270 MHz, DMSO-$d_6$) δ 2.78 (d, J=4.4 Hz, 3H), 3.14-3.65 (m, 9H), 7.18-7.24 (m, 1H), 7.36-7.42 (m, 1H), 7.50-7.68 (m, 3H), 7.78 (d, J=5.5 Hz, 2H), 7.84 (d, J=8.4 Hz, 2H), 8.19 (d, J=8.1 Hz, 1H), 8.42 (d, J=4.5 Hz, 1H), 13.2 (s, 1H).

ESI-MS (m/z); 389 [M+H]$^+$

EXAMPLE 81

(E)-N,N-diethyl-1-{4-[2-(1H-indazol-3-yl)vinyl]benzoyl}piperidine-4-carboxamide (Compound 81)

In a similar manner to Example 5, Compound 81 (48 mg, 14%) was obtained using Compound 50 (300 mg, 0.80 mmol), diethylamine (0.099 mL, 0.96 mmol), 1-hydroxybenzotriazole monohydrate (184 mg, 1.20 mmol), 1-ethyl-3-(3-dimethylaminopropyl)carbodiimide hydrochloride (230 mg, 1.20 mmol) and N-methylmorpholine (0.13 mL, 1.20 mmol).

$^1$H-NMR (270 MHz, DMSO-$d_6$) δ 0.99 (t, J=7.1 Hz, 3H), 1.12 (t, J=7.1 Hz, 3H), 1.51-1.59 (m, 4H), 2.49 (m, 1H), 2.82-3.29 (m, 4H), 3.35-3.43 (m, 4H), 7.17-7.23 (m, 1H), 7.37-7.42 (m, 2H), 7.53-7.65 (m, 2H), 7.77 (d, J=8.2 Hz, 2H), 8.19 (d, J=8.1 Hz, 1H), 13.2 (s, 1H). ESI-MS (m/z); 431 [M+H]$^+$

EXAMPLE 82

(E)-1-(tert-butoxycarbonyl)-4-{4-[2-(1H-indazol-3-yl)vinyl]benzoyl}homopiperazine (Compound 82)

In a similar manner to Example 5, Compound 82 (1.52 g, 30%) was obtained using (E)-4-[2-(1H-indazol-3-yl)vinyl] benzoic acid (3.00 g, 11.4 mmol) obtained in Step 6 of Example 1, 1-(tert-butoxycarbonyl)homopiperazine (3.41 g, 17.0 mmol), 1-hydroxybenzotriazole monohydrate (1.99 g, 14.7 mmol), 1-ethyl-3-(3-dimethylaminopropyl)carbodiimide hydrochloride (3.05 g, 15.9 mmol) and N-methylmorpholine (4.13 mL, 37.6 mmol).

$^1$H-NMR (270 MHz, DMSO-$d_6$) δ 1.41 (s, 9H), 1.52 (m, 1H), 1.46 (m, 1H), 3.33-3.69 (m, 8H), 7.21 (t, J=7.9 Hz, 1H), 7.36 (t, J=8.1 Hz, 1H), 7.42 (d, J=8.4 Hz, 2H), 7.53 (d, J=16.5 Hz, 1H), 7.56 (d, J=8.1 Hz, 1H), 7.66 (d, J=16.5 Hz, 1H), 7.77 (d, J=8.1 Hz, 2H), 8.20 (d, J=7.6 Hz, 1H), 13.2 (br, 1H). ESI-MS (m/z); 447 [M+H]$^+$

EXAMPLE 83

(E)-4-{2-chloro-4-[2-(1H-indazol-3-yl)vinyl] benzoyl}piperazine-1-carboxylic acid 1,1-dimethylethylester (Compound 83)

In a similar manner to Example 5, Compound 83 (157 mg, 34%) was obtained using (E)-4-[2-(1H-indazol-3-yl)vinyl]-2-chlorobenzoic acid (300 mg, 1.00 mmol), N-(tert-butoxycarbonyl)piperazine (280 mg, 1.51 mmol), 1-hydroxybenzotriazole monohydrate (199 mg, 1.30 mmol) and 1-ethyl-3-(3-dimethylaminopropyl)carbodiimide hydrochloride (268 mg, 1.40 mmol).

$^1$H-NMR (270 MHz, DMSO-$d_6$) δ 1.47 (s, 9H), 3.23-3.57 (m, 6H), 3.71-3.89 (m, 2H), 7.26-7.32 (m, 3H), 7.42-7.55 (m, 4H), 7.62 (d, J=1.3 Hz, 1H), 8.02 (d, J=8.1 Hz, 1H), 10.1-10.2 (brs, 1H). ESI-MS (m/z); 467 [M+H]$^+$

EXAMPLE 84

(E)-4-{2-methyl-4-[2-(1H-indazol-3-yl)vinyl] benzoyl}piperazine-1-carbaldehyde (Compound 84)

In a similar manner to Example 5, Compound 84 (4.5 mg, 13%) was obtained using (E)-4-[2-(1H-indazol-3-yl)vinyl]-2-methylbenzoic acid (221 mg, 0.761 mmol), N-formylpiperazine (0.120 mL, 1.13 mmol), 1-hydroxybenzotriazole monohydrate (151 mg, 0.982 mmol) and 1-ethyl-3-(3-dimethylaminopropyl)carbodiimide hydrochloride (203 mg, 1.06 mmol).

$^1$H-NMR (300 MHz, CDCl$_3$) δ 2.37 (s, 3H), 3.25-3.32 (br, 4H), 3.51-3.85 (br, 4H), 6.88 (m, 1H), 7.19-7.31 (m, 3H), 7.42-7.53 (m, 4H), 8.04 (d, J=8.3 Hz, 1H), 10.1 (br, 1H). ESI-MS (m/z); 375 [M+H]$^+$

EXAMPLE 85

(E)-1-{4-[2-(1H-indazol-3-yl)vinyl] benzoyl}homopiperazine dihydrochloride (Compound 85)

A solution of Compound 82 (100 mg, 0.224 mmol) in methanol (10.0 mL) was added with 10% hydrogen chloride-methanol solution (10.0 mL), followed by stirring at 60° C. for 2 hours. After cooling to room temperature, deposited crystal was collected by filtration to obtain Compound 85 (48.7 mg, 47%).

$^1$H-NMR (270 MHz, DMSO-$d_6$) δ 2.00-2.18 (m, 2H), 3.21-3.32 (m, 4H), 3.45-3.69 (m, 4H), 7.21 (t, J=7.3 Hz, 1H), 7.38 (t, J=8.3 Hz, 1H), 7.44 (d, J=8.6 Hz, 2H), 7.53 (d, J=16.1 Hz, 1H), 7.57 (d, J=8.3 Hz, 1H), 7.67 (d, J=16.1 Hz, 1H), 7.78 (d, J=8.3 Hz, 2H), 8.19 (d, J=8.3 Hz, 1H), 9.37 (br, 2H), 9.60 (br, 1H). ESI-MS (m/z); 347 [M+H]$^+$

EXAMPLE 86

(E)-1-{4-[2-(1H-indazol-3-yl)vinyl] benzoyl}piperidine-4-carboxamide (Compound 86)

In a similar manner to Example 5, Compound 86 (89 mg, 22%) was obtained using Compound 50 (400 mg, 1.06 mmol), 1-hydroxybenzotriazole monoammonium salt (400 mg, 1.6 mmol), 1-ethyl-3-(3-dimethylaminopropyl)carbodiimide hydrochloride (307 mg, 1.6 mmol) and N-methylmorpholine (0.350 mL, 3.18 mmol).

$^1$H-NMR (270 MHz, DMSO-$d_6$) δ 1.47 (brs, 2H), 1.72 (brs, 2H), 2.49 (m, 1H), 3.34 (brs, 2H), 3.45 (brs, 2H), 6.82 (brs, 1H), 7.21 (m, 1H), 7.31 (brs, 2H), 7.39 (m, 2H), 7.59 (m, 3H), 7.76 (d, J=8.4 Hz, 2H), 8.19 (d, J=8.4 Hz, 1H), 13.2 (brs, 1H). ESI-MS (m/z); 375 [M+H]$^+$

EXAMPLE 87

(E)-1-{4-[2-(1H-indazol-3-yl)vinyl]benzoyl}-4-hydroxypiperidine (Compound 87)

In a similar manner to Example 5 Compound 87 (99.1 mg, 15%) was obtained using (E)-4-[2-(1H-indazol-3-yl)vinyl] benzoic acid (300 mg, 1.89 mmol), 4-hydroxypiperidine (230 mg, 2.27 mmol), 1-hydroxybenzotriazole monohydrate (434 mg, 2.84 mmol), 1-ethyl-3-(3-dimethylaminopropyl)carbodiimide hydrochloride (543.5 mg, 2.84 mmol) and N-methylmorpholine (0.623 mL, 5.67 mmol).

$^1$H-NMR (300 MHz, DMSO-$d_6$) δ 1.36 (brs, 2H), 1.74 (brs, 2H), 3.20 (brs, 2H), 3.48 (brs, 2H), 3.73 (brs, 1H), 4.81 (br, 1H), 7.21 (m, 1H), 7.39 (m, 3H), 7.55 (m, 3H), 7.76 (d, J=8.4 Hz, 2H), 8.19 (d, J=8.4 Hz, 1H). ESI-MS (m/z); 348 [M+H]$^+$

EXAMPLE 88

(E)-N-methyl-N-(2-oxo-2-morpholinoethyl)-4-[2-(1H-indazol-3-yl)vinyl]benzamide (Compound 88)

Step 1

The product obtained using (E)-4-[2-(1H-indazol-3-yl)vinyl]benzoic acid (1.50 g, 5.68 mmol), sarcosine ethyl ester hydrochloride (1.05 g, 6.81 mmol), 1-hydroxybenzotriazole monohydrate (1.31 g, 6.81 mmol), 1-ethyl-3-(3-dimethylaminopropyl)carbodiimide hydrochloride (1.63 g, 8.52 mmol) and N-methylmorpholine (1.87 mL, 17.0 mmol) in a similar manner to Example 5, was neutralized by adding 2 mol/L aqueous sodium hydroxide solution (20 ml), and the mixture was filtered to obtain (E)-N-methyl-N-carboxymethyl-4-[2-(1H-indazol-3-yl)vinyl]benzamide (1.04 g, 55%).

Step 2

In a similar manner to Example 5, Compound 88 (218 mg, 61%) was obtained using (E)-N-methyl-N-carboxymethyl-4-[2-(1H-indazol-3-yl)vinyl]benzamide (300 mg, 0.89 mmol) obtained in Step 1, morpholine (0.093 mL, 1.07 mmol), 1-hydroxybenzotriazole monohydrate (205 mg, 1.34 mmol), 1-ethyl-3-(3-dimethylaminopropyl)carbodiimide hydrochloride (256 mg, 1.34 mmol) and N-methylmorpholine (0.294 mL, 2.67 mmol).

$^1$H-NMR (300 MHz, DMSO-$d_6$) δ 2.94 (s, 3H), 3.20-3.60 (m, 8H), 4.33 (s, 2H), 7.20 (m, 1H), 7.30 (d, J=7.8 Hz, 1H), 7.36-7.45 (m, 2H), 7.53-7.60 (m, 3H), 7.73-7.80 (m, 2H), 8.19 (d, J=8.3 Hz, 1H), 13.2 (s, 1H). ESI-MS (m/z); 405 [M+H]$^+$

EXAMPLE 89

(E)-4-{4-[2-(1H-indazol-3-yl)vinyl]benzoyl}piperadin-2-one (Compound 89)

In a similar manner to Example 5, Compound 89 (309 mg, 60%) was obtained using (E)-4-[2-(1H-indazol-3-yl)vinyl]benzoic acid (500 mg, 1.89 mmol) obtained in Step 6 of Example 1, piperadin-2-one (284 mg, 2.83 mmol), 1-hydroxybenzotriazole monohydrate (332 mg, 2.46 mmol), 1-ethyl-3-(3-dimethylaminopropyl)carbodiimide hydrochloride (510 mg, 2.67 mmol) and N-methylmorpholine (850 mL, 7.73 mmol).

$^1$H-NMR (300 MHz, DMSO-$d_6$) δ 3.20-3.28 (m, 2H), 3.55-3.64 (m, 2H), 4.00-4.04 (brs, 2H), 7.21 (t, J=7.3 Hz, 1H), 7.40 (t, J=7.3 Hz, 1H), 7.47 (d, J=8.4 Hz, 2H), 7.52 (d, J=16.1 Hz, 1H), 7.58 (d, J=8.0 Hz, 1H), 7.68 (d, J=16.1 Hz, 1H), 7.80 (d, J=8.1 Hz, 2H), 8.13 (br, 1H), 8.20 (d, J=8.1 Hz, 1H), 13.2 (br, 1H). ESI-MS (m/z); 347 [M+H]$^+$

EXAMPLE 90

(E)-4-(3-methyl-3-hydroxybutyryl)-1-{4-[2-(1H-indazol-3-yl)vinyl]benzoyl}piperazine (Compound 90)

In a similar manner to Example 5, Compound 90 (204 mg, 66%) was obtained using dihydrochloride of Compound 18 (320 mg, 0.963 mmol), β-hydroxyisovaleric acid (85.0 mg, 0.718 mmol), 1-hydroxybenzotriazole monohydrate (126 mg, 0.932 mmol), 1-ethyl-3-(3-dimethylaminopropyl)carbodiimide hydrochloride (193 mg, 1.01 mmol) and N-methylmorpholine (0.322 mL, 2.93 mmol).

$^1$H-NMR (270 MHz, DMSO-$d_6$) δ 1.18 (s, 6H), 3.30 (s, 2H), 3.36-3.55 (m, 8H), 4.76 (br, 1H), 7.21 (t, J=8.1 Hz, 1H), 7.38 (t, J=7.3 Hz, 1H), 7.44 (d, J=8.4 Hz, 2H), 7.51 (d, J=16.3 Hz, 1H), 7.57 (d, J=8.1 Hz, 1H), 7.67 (d, J=16.3 Hz, 1H), 7.79 (d, J=8.1 Hz, 2H), 8.20 (d, J=8.1 Hz, 1H), 13.2 (br, 1H). ESI-MS (m/z); 433 [M+H]$^+$

EXAMPLE 91

(E)-N-(3-oxo-3-morpholinopropyl)-4-[2-(1H-indazol-3-yl)vinyl]benzamide (Compound 91)

Step 1

Compound 79 (1.0 g, 2.75 mmol) was dissolved in THF (30 mL), and the solution was added with 2 mol/L aqueous sodium hydroxide solution (20 mL), followed by neutralization and filtration to obtain (E)-N-(2-carboxyethyl)-4-[2-(1H-indazol-3-yl)vinyl]benzamide (710 mg, 77%).

Step 2

In a similar manner to Example 5, Compound 91 (466 mg, 66%) was obtained using (E)-N-(2-carboxyethyl)-4-[2-(1H-indazol-3-yl)vinyl]benzamide (300 mg, 0.900 mmol), morpholine (0.094 mL, 1.07 mmol), 1-hydroxybenzotriazole monohydrate (206 mg, 1.34 mmol), 1-ethyl-3-(3-dimethylaminopropyl)carbodiimide hydrochloride (257 mg, 1.34 mmol) and N-methylmorpholine (0.295 mL, 2.69 mmol).

$^1$H-NMR (270 MHz, DMSO-$d_6$) δ 2.57-2.63 (m, 2H), 3.27-3.31 (m, 3H), 3.36-3.39 (m, 4H), 3.44-3.55 (m, 4H), 7.21 (m, 1H), 7.39 (m, 1H), 7.50-7.63 (m, 3H), 7.69-7.87 (m, 4H), 8.20 (d, J=8.1 Hz, 1H), 8.51 (m, 1H). ESI-MS (m/z); 405 [M+H]$^+$

EXAMPLE 92

(E)-N,N-dimethyl-1-{4-[2-(1H-indazol-3-yl)vinyl]benzoyl}piperidine-4-carboxamide (Compound 92)

In a similar manner to Example 5, Compound 92 (27 mg, 5%) was obtained using Compound 50 (500 mg, 1.33 mmol), dimethylamine hydrochloride (230 mg, 1.50 mmol), 1-hydroxybenzotriazole monohydrate (306 mg, 2.00 mmol), 1-ethyl-3-(3-dimethylaminopropyl)carbodiimide hydrochloride (383 mg, 2.00 mmol) and N-methylmorpholine (0.439 mL, 4.00 mmol).

$^1$H-NMR (300 MHz, DMSO-$d_6$) δ 1.43 (brs, 2H), 1.53 (brs, 2H), 2.80 (s, 3H), 2.92 (brs, 2H), 3.02 (s, 3H), 3.20 (brs, 2H), 4.00 (brs, 1H), 4.44 (brs, 1H), 7.20 (t, J=7.3 Hz, 1H), 7.38 (m, 3H), 7.55 (m, 3H), 7.76 (d, J=8.1 Hz, 2H), 8.19 (d, J=8.1 Hz, 1H), 13.2 (brs, 1H). ESI-MS (m/z); 403 [M+H]$^+$

EXAMPLE 93

(E)-N-[2-(diethylcarbamoyl)ethyl]-4-[2-(1H-indazol-3-yl)vinyl]benzamide (Compound 93)

In a similar manner to Example 5, Compound 93 (119 mg, 24%) was obtained using (E)-N-(2-carboxyethyl)-4-[2-(1H-indazol-3-yl)vinyl]benzamide (400 mg, 1.25 mmol) obtained in Step 1 of Example 91, diethylamine (0.155 mL, 1.5 mmol), 1-hydroxybenzotriazole monohydrate (287 mg, 1.88 mmol), 1-ethyl-3-(3-dimethylaminopropyl)carbodiimide hydrochloride (359 mg, 1.88 mmol) and N-methylmorpholine (0.041 mL, 3.7 mmol).

$^1$H-NMR (270 MHz, DMSO-$d_6$) δ 0.91 (t, J=7.1 Hz, 3H), 0.98 (t, J=7.1 Hz, 3H), 2.39 (s, 1H), 3.19 (dd, J=12.6, 6.9 Hz, 4H), 3.28 (m, 2H), 3.39 (dd, J=12.9, 6.9 Hz, 2H), 7.08-7.14 (m, 1H), 7.27-7.33 (m, 1H), 7.43-7.62 (m, 2H), 7.72 (dd, J=19.5, 8.3 Hz, 5H), 8.12 (d, J=8.1 Hz, 1H), 8.42 (t, J=5.5 Hz, 1H), 13.1 (s, 1H). APCI-MS (m/z); 391 [M+H]$^+$

EXAMPLE 94

(E)-N-diethylcarbamoylmethyl-4-[2-(1H-indazol-3-yl)vinyl]benzamide (Compound 94)

In a similar manner to Example 5, Compound 94 (103 mg, 29%) was obtained using Compound 53 (300 mg, 0.932 mmol), diethylamine (123 mg, 1.12 mmol), 1-hydroxybenzotriazole monohydrate (214 mg, 1.40 mmol) and 1-ethyl-3-(3-dimethylaminopropyl)carbodiimide hydrochloride (268 mg, 1.40 mmol).

¹H-NMR (270 MHz, DMSO-d₆) δ 1.02 (t, J=7.0 Hz, 3H), 1.16 (t, J=7.0 Hz, 3H), 3.27-3.36 (m, 4H), 4.10 (d, J=5.5 Hz, 2H), 7.21 (m, 1H), 7.39 (m, 1H), 7.53-7.71 (m, 3H), 7.86 (dd, J=26.4, 8.1 Hz, 4H), 8.20 (d, J=8.1 Hz, 1H), 8.57 (s, 1H), 13.2 (s, 1H). ESI-MS (m/z); 377 [M+H]⁺

EXAMPLE 95

(E)-1-{4-[2-(1H-indazol-3-yl)vinyl]-2-methylbenzoyl}piperazine dihydrochloride (Compound 95)

Step 1

In a similar manner to Example 5, (E)-4-{4-[2-(1H-indazol-3-yl)vinyl]-2-methylbenzoyl}piperazine-1-carboxylic acid 1,1-dimethylethyl ester (980 mg, 66%) was obtained using (E)-4-[2-(1H-indazol-3-yl)vinyl]-2-methylbenzoic acid (970 mg, 3.32 mmol), N-(1,1-dimethylethoxycarbonyl)piperazine (926 mg, 4.98 mmol), 1-hydroxybenzotriazole monohydrate (661 mg, 4.32 mmol) and 1-ethyl-3-(3-dimethylaminopropyl)carbodiimide hydrochloride (891 mg, 4.65 mmol).

¹H-NMR (270 MHz, CDCl₃) δ 1.57 (s, 9H), 2.36 (s, 3H), 3.24-3.28 (br, 2H), 3.36-3.38 (br, 2H), 3.50-3.56 (br, 2H), 3.76-3.82 (br, 2H), 7.18 (d, J=5.1 Hz, 1H), 7.23-7.32 (m, 2H), 7.44-7.49 (m, 5H), 8.04 (d, J=8.2 Hz, 1H), 10.1 (br, 1H). ESI-MS (m/z); 447 [M+H]⁺

Step 2

(E)-4-{4-[2-(1H-indazol-3-yl)vinyl]-2-methylbenzoyl}piperazine-1-carboxylic acid 1,1-dimethylethyl ester (980 mg, 2.20 mmol) obtained in Step 1, was treated with 10% hydrogen chloride-methanol solution to obtain Compound 95 (585 mg, 77%).

¹H-NMR (270 MHz, DMSO-d₆) δ 2.26 (s, 3H), 3.04-3.41 (br, 4H), 3.55-3.60 (br, 4H), 7.14-7.64 (m, 8H), 8.18 (d, J=8.2 Hz, 1H), 9.35-9.45 (br, 2H). ESI-MS (m/z); 347 [M+H]⁺

EXAMPLE 96

(E)-4-{4-[2-(1H-indazol-3-yl)vinyl]benzoyl}-1-methylpiperazin-2-one (Compound 96)

In a similar manner to Example 5, Compound 96 (198 mg, 46%) was obtained using (E)-4-[2-(1H-indazol-3-yl)vinyl]benzoic acid (400 mg, 1.19 mmol) obtained in Step 6 of Example 1, 1-methylpiperazin-2-one (780 mg, 5.18 mmol), 1-hydroxybenzotriazole monohydrate (210 mg, 1.55 mmol), 1-ethyl-3-(3-dimethylaminopropyl)carbodiimide hydrochloride (320 mg, 1.70 mmol) and N-methylmorpholine (0.70 mL, 6.37 mmol).

¹H-NMR (270 MHz, DMSO-d₆) δ 2.87 (s, 3H), 3.37-3.39 (m, 2H), 3.60-3.82 (brm, 2H), 4.03-4.09 (m, 2H), 7.21 (t, J=7.6 Hz, 1H), 7.39 (t, J=7.6 Hz, 1H), 7.47 (d, J=8.2 Hz, 2H), 7.51 (d, J=16.1 Hz, 1H), 7.56 (d, J=8.1 Hz, 1H), 7.68 (d, J=16.1 Hz, 1H), 7.80 (d, J=8.2 Hz, 2H), 8.20 (d, J=8.1 Hz, 1H), 13.2 (br, 1H). ESI-MS (m/z); 360 [M+H]⁺

EXAMPLE 97

(E)-N-(3-morpholinopropyl)-4-[2-(1H-indazol-3-yl)vinyl]benzamide dihydrochloride (Compound 97)

The crude product obtained using (E)-4-[2-(1H-indazol-3-yl)vinyl]benzoic acid (500 mg, 1.89 mmol) obtained in Step 6 of Example 1, N-(3-aminopropyl)morpholine (0.365 mL, 2.50 mmol), 1-hydroxybenzotriazole monohydrate (333 mg, 2.46 mmol), 1-ethyl-3-(3-dimethylaminopropyl)carbodiimide hydrochloride (510 mg, 2.67 mmol) and N-methylmorpholine (0.75 mL, 6.82 mmol) in a similar manner to Example 5, was purified by silica gel column chromatography (hexane/ethyl acetate) to obtain a free base of Compound 97. Then the free base of Compound 97 was dissolved in ethyl acetate (5.00 mL), and the solution was added with 4 moL/L hydrogen chloride-ethyl acetate solution (1.00 mL), followed by stirring at room temperature for 30 minutes. The precipitate in the reaction mixture was filtered to obtain Compound 97 (340 mg, 78%).

¹H-NMR (270 MHz, DMSO-d₆) δ 1.98 (br, 2H), 3.03-3.12 (m, 4H), 3.34-3.44 (m, 4H), 3.73-3.97 (m, 4H), 7.21 (t, J=7.4 Hz, 1H), 7.40 (t, J=7.4 Hz, 1H), 7.55 (d, J=16.7 Hz, 1H), 7.56 (d, J=7.4 Hz, 1H), 7.68 (d, J=16.7 Hz, 1H), 7.81 (d, J=7.4 Hz, 2H), 7.90 (d, J=7.4 Hz, 2H), 8.21 (d, J=7.4 Hz, 1H), 8.71 (br, 1H). ESI-MS (m/z); 391 [M+H]⁺

EXAMPLE 98

(E)-4-(3-methoxypropionyl)-1-{4-[2-(1H-indazol-3-yl)vinyl]benzoyl}piperazine (Compound 98)

In a similar manner to Example 5, Compound 98 (220 mg, 59%) was obtained using dihydrochloride of Compound 18 (400 mg, 0.99 mmol), β-3-methoxypropionic acid (84.4 mg, 0.82 mmol), 1-hydroxybenzotriazole monohydrate (178 mg, 1.32 mmol), 1-ethyl-3-(3-dimethylaminopropyl)carbodiimide hydrochloride (265 mg, 1.38 mmol) and N-methylmorpholine (0.4 mL, 1.64 mmol).

¹H-NMR (270 MHz, DMSO-d₆) δ 2.58 (t, J=6.2 Hz, 2H), 3.22 (s, 3H), 3.26-3.29 (m, 2H), 3.52-3.57 (m, 8H), 7.21 (t, J=7.7 Hz, 1H), 7.38 (d, J=8.2 Hz, 1H), 7.44, (d, J=8.2 Hz, 2H), 7.54 (d, J=16.8 Hz, 1H), 7.55 (d, J=8.2 Hz, 1H), 7.64 (d, J=16.8 Hz, 1H), 7.79 (d, J=8.2 Hz, 2H), 8.20 (d, J=8.2 Hz, 1H), 13.2 (br, 1H). APCI-MS (m/z); 419 [M+H]⁺

EXAMPLE 99

(E)-1-{4-[2-(1H-indazol-3-yl)vinyl]benzoyl}-4-(morpholinocarbonylamino)piperidine (Compound 99)

Compound 64 (500 mg, 1.19 mmol) was dissolved in dichloromethane, and the solution was added with triethylamine (0.498 mL, 3.57 mmol), 4-morpholinecarbonyl chloride (468 mg, 2.62 mmol) and 1-ethyl-3-(3-dimethylaminopropyl)carbodiimide hydrochloride (200.2 mg, 1.04 mmol) at 0° C., followed by stirring for 4 hours to obtain Compound 99 (1.5 mg, 0.3%).

¹H-NMR (270 MHz, DMSO-d₆) δ 1.37 (brs, 4H), 1.77 (brs, 4H), 3.18-3.53 (m, 9H), 6.30 (d, J=7.1 Hz, 1H), 7.20-7.23 (m, 1H), 7.35-7.42 (m, 3H), 7.53-7.65 (m, 4H), 7.76 (d, J=7.9 Hz, 2H), 8.18 (d, J=8.1 Hz, 1H). APCI-MS (m/z); 460 [M+H]⁺

EXAMPLE 100

(E)-4-(2-methoxyacetyl)-1-{4-[2-(1H-indazol-3-yl)vinyl]-2-methylbenzoyl}piperazine (Compound 100)

A solution of methoxyacetic acid (0.019 mL, 0.24 mmol) in THF (5.0 mL) was added with Compound 95 (0.10 g, 0.29 mmol), 1-hydroxybenzotriazole monohydrate (52 mg, 0.337 mmol) and 1-ethyl-3-(3-dimethylaminopropyl)carbodiimide hydrochloride (69 mg, 0.36 mmol), followed by stirring at 60° C. for 1 hour. The reaction mixture was added with ethyl acetate and saturated aqueous sodium hydrogencarbonate solution (4.0 mL) and was extracted. The organic layer was concentrated under reduced pressure. The residue was purified by silica gel column chromatography (ethyl acetate/methanol=10/1), and the product was added with ethyl acetate, then precipitate was collected by filtration to obtain Compound 100 (39 mg, 39%).

$^1$H-NMR (270 MHz, DMSO-$d_6$) δ 2.27 (s, 3H), 3.19 (brs, 2H), 3.29 (brs, 3H), 3.37 (brs, 2H), 3.51 (brs, 2H), 4.10 (brd, 2H), 7.21 (t, J=6.6 Hz, 1H), 7.22 (d, J=7.9 Hz, 1H), 7.40 (t, J=6.6 Hz, 1H), 7.49 (d, J=16.6 Hz, 1H), 7.60 (d, J=16.6 Hz, 1H), 7.67-7.50 (m, 3H), 8.19 (d, J=8.4 Hz, 1H), 13.18 (s, 1H) APCI-MS (m/z); 419 [M+H]$^+$

EXAMPLE 101

(S)-(E)-1-{4-[2-(1H-indazol-3-yl)vinyl]benzoyl}-3-methylpiperazine dihydrochloride (Compound 101)

In a similar manner to Example 5, a free base of Compound 101 was obtained using (E)-4-[2-(1H-indazol-3-yl)vinyl]benzoic acid (250 mg, 0.83 mmol) obtained in Step 6 of Example 1, (S)-(+)-2-methylpiperazine (170 mg, 1.66 mmol), 1-hydroxybenzotriazole monohydrate (217 mg, 1.60 mmol), 1-ethyl-3-(3-dimethylaminopropyl)carbodiimide hydrochloride (303 mg, 1.58 mmol) and N-methylmorpholine (0.23 mL, 2.08 mmol), then the free base of Compound 101 was dissolved in methanol (2.00 mL), and the solution was added with 4 moL/L hydrogen chloride-methanol solution (1.50 mL), followed by stirring at room temperature for 30 minutes. The reaction mixture was concentrated under reduced pressure, and the residue was crystallized from acetone to obtain Compound 101 (158 mg, 45%).

$^1$H-NMR (270 MHz, DMSO-$d_6$) δ 1.26 (br, 3H), 2.75 (br, 1H), 3.05-3.34 (m, 6H), 7.22 (dd, J=7.9, 7.9 Hz, 1H), 7.40 (dd, J=7.9, 7.9 Hz, 1H), 7.49 (d, J=8.3 Hz, 2H), 7.54 (d, J=8.3 Hz, 1H), 7.55 (d, J=16.8 Hz, 1H), 7.66 (d, J=16.1 Hz, 1H), 7.81 (d, J=8.3 Hz, 2H), 8.21 (d, J=8.3 Hz, 1H), 9.47-9.51 (m, 1H), 9.65 (br, 1H). APCI-MS (m/z); 347 [M+H]$^+$

EXAMPLE 102

(R)-(E)-1-{4-[2-(1H-indazol-3-yl)vinyl]benzoyl}-3-methylpiperazine dihydrochloride (Compound 102)

In a similar manner to Example 5, a free base of Compound 102 was obtained using (E)-4-[2-(1H-indazol-3-yl)vinyl]benzoic acid (250 mg, 0.83 mmol) obtained in Step 6 of Example 1, (R)-(+)-2-methylpiperazine (170 mg, 1.66 mmol), 1-hydroxybenzotriazole monohydrate (217 mg, 1.60 mmol), 1-ethyl-3-(3-dimethylaminopropyl)carbodiimide hydrochloride (303 mg, 1.58 mmol) and N-methylmorpholine (0.23 mL, 2.08 mmol), then the free base of Compound 102 was dissolved in methanol (2.00 mL) and the solution was added with 4 moL/L hydrogen chloride-methanol solution (1.50 mL), followed by stirring at room temperature for 30 minutes. The reaction mixture was concentrated under reduced pressure, and the residue was crystallized from acetone to obtain Compound 102 (50 mg, 14%).

$^1$H-NMR (270 MHz, DMSO-$d_6$) δ 1.26 (br, 3H), 2.75 (br, 1H), 3.09-3.45 (m, 6H), 7.22 (dd, J=7.9, 7.9 Hz, 1H), 7.40 (dd, J=7.9, 7.9 Hz, 1H), 7.49 (d, J=8.3 Hz, 2H), 7.54 (d, J=8.3 Hz, 1H), 7.55 (d, J=16.8 Hz, 1H), 7.66 (d, J=16.1 Hz, 1H), 7.81 (d, J=8.3 Hz, 2H), 8.21 (d, J=8.3 Hz, 1H), 9.47-9.51 (m, 1H), 9.65 (br, 1H). APCI-MS (m/z); 347 [M+H]$^+$

EXAMPLE 103

(S*,S*)-(E)-1-{4-[2-(1H-indazol-3-yl)vinyl]benzoyl}-3,5-dimethylpiperazine dihydrochloride (Compound 103)

In a similar manner to Example 5, a free base of Compound 103 was obtained using (E)-4-[2-(1H-indazol-3-yl)vinyl]benzoic acid (250 mg, 0.83 mmol) obtained in Step 6 of Example 1, 2,6-dimethylpiperazine (243 mg, 1.66 mmol), 1-hydroxybenzotriazole monohydrate (217 mg, 1.60 mmol), 1-ethyl-3-(3-dimethylaminopropyl)carbodiimide hydrochloride (303 mg, 1.58 mmol) and N-methylmorpholine (0.23 mL, 2.08 mmol), then the free base of Compound 103 was dissolved in methanol (2.00 mL), and the solution was added with 4 moL/L hydrogen chloride-methanol solution (1.50 mL), followed by stirring at room temperature for 30 minutes. The reaction mixture was concentrated under reduced pressure, and the residue was crystallized from acetone to obtain Compound 103 (140 mg, 51%).

$^1$H-NMR (270 MHz, DMSO-$d_6$) δ 1.28 (br, 6H), 3.03-3.33 (br, 4H), 4.5 (br, 2H), 7.24 (dd, J=8.3, 8.3 Hz, 1H), 7.41 (dd, J=8.3, 8.3 Hz, 1H), 7.50 (d, J=8.3 Hz, 2H), 7.54 (d, J=8.3 Hz, 1H), 7.56 (d, J=16.7 Hz, 1H), 7.66 (d, J=16.7 Hz, 1H), 7.81 (d, J=8.3 Hz, 2H), 8.21 (d, J=8.3 Hz, 1H), 9.48-9.51 (m, 1H), 9.87-9.90 (m, 1H). APCI-MS (m/z); 361 [M+H]$^+$

EXAMPLE 104

(E)-1-{4-[2-(1H-indazol-3-yl)vinyl]benzoyl}-4-ethylpiperazine dihydrochloride (Compound 104)

In a similar manner to Example 5, a free base of Compound 104 was obtained using (E)-4-[2-(1H-indazol-3-yl)vinyl]benzoic acid (300 mg, 1.00 mmol) obtained in Step 6 of Example 1, N-ethylpiperazine (171 mg, 1.50 mmol), 1-hydroxybenzotriazole monohydrate (176 mg, 1.30 mmol), 1-ethyl-3-(3-dimethylaminopropyl)carbodiimide hydrochloride (270 mg, 1.40 mmol)-and N-methylmorpholine (0.22 mL, 2.00 mmol), then the free base of Compound 104 was dissolved in methanol (2.00 mL) and the solution was added with 4 moL/L hydrogen chloride-methanol solution (1.50 mL), followed by stirring at room temperature for 30 minutes. The reaction mixture was concentrated under reduced pressure, and the residue was crystallized from acetone to obtain Compound 104 (280 mg, 65%).

$^1$H-NMR (270 MHz, DMSO-$d_6$) δ 1.27 (t, J=7.4 Hz, 3H), 3.03-3.14 (m, 4H), 3.46 (br, 2H), 4.54 (br, 4H), 7.22 (dd, J=7.4, 7.4 Hz, 1H), 7.41 (dd, J=7.4, 7.4 Hz, 1H), 7.50 (d, J=8.2 Hz, 2H), 7.54 (d, J=7.4 Hz, 1H), 7.56 (d, J=16.7 Hz, 1H), 7.67 (d, J=16.7 Hz, 1H), 7.81 (d, J=8.2 Hz, 2H), 8.21 (d, J=8.2 Hz, 1H), 11.2 (br, 1H). APCI-MS (m/z); 361 [M+H]$^+$

EXAMPLE 105

(E)-1-{4-[2-(1H-indazol-3-yl)vinyl]benzoyl}-4-(2-hydroxyethyl)piperazine (Compound 105)

In a similar manner to Example 5, Compound 105 (230 mg, 61%) was obtained using (E)-4-[2-(1H-indazol-3-yl)vinyl]benzoic acid (300 mg, 1.00 mmol) obtained in Step 6 of Example 1, 2-(piperazin-1-yl)ethanol (195 mg, 1.50 mmol), 1-hydroxybenzotriazole monohydrate (176 mg, 1.30 mmol), 1-ethyl-3-(3-dimethylaminopropyl)carbodiimide hydrochloride (270 mg, 1.40 mmol) and N-methylmorpholine (0.22 mL, 2.00 mmol).

$^1$H-NMR (270 MHz, DMSO-d$_6$) δ 2.41-2.49 (m, 8H), 3.48-3.55 (m, 4H), 4.43 (t, J=5.4 Hz, 1H), 7.23 (dd, J=8.1, 8.1 Hz, 1H), 7.18-7.28 (m, 1H), 7.23 (d, J=8.1 Hz, 2H), 7.54 (d, J=16.1 Hz, 1H), 7.57 (d, J=16.7 Hz, 1H), 7.67 (d, J=8.1 Hz, 1H), 7.78 (d, J=8.1 Hz, 2H), 8.20 (d, J=8.1 Hz, 1H), 13.2 (br, 1H). APCI-MS (m/z); 377 [M+H]$^+$

EXAMPLE 106

(E)-1-{4-[2-(1H-indazol-3-yl)vinyl]benzoyl}-4-morpholinopiperidine (Compound 106)

In a similar manner to Example 5, Compound 106 (319 mg, 77%) was obtained using (E)-4-[2-(1H-indazol-3-yl)vinyl]benzoic acid (300 mg, 1.00 mmol) obtained in Step 6 of Example 1, 4-morpholinopiperidine (255 mg, 1.50 mmol), 1-hydroxybenzotriazole monohydrate (176 mg, 1.30 mmol), 1-ethyl-3-(3-dimethylaminopropyl)carbodiimide hydrochloride (270 mg, 1.40 mmol) and N-methylmorpholine (0.22 mL, 2.00 mmol).

$^1$H-NMR (270 MHz, DMSO-d$_6$) δ 1.31-1.43 (m, 2H), 1.81 (br, 2H), 2.38 (br, 2H), 2.42 (br, 4H), 2.86-3.00 (m, 2H), 3.55-3.58 (m, 4H), 4.44 (br, 1H), 7.22 (dd, J=7.9, 7.9 Hz, 1H), 7.39 (d, J=8.3 Hz, 1H), 7.41 (d, J=8.3 Hz, 2H), 7.57 (d, J=16.8 Hz, 1H), 7.59 (d, J=8.3 Hz, 1H), 7.64 (d, J=16.8 Hz, 1H), 7.78 (d, J=8.3 Hz, 2H), 8.21 (d, J=8.3 Hz, 1H), 13.2 (br, 1H). APCI-MS (m/z); 417 [M+H]$^+$

EXAMPLE 107

(E)-1-{4-[2-(1H-indazol-3-yl)vinyl]benzoyl}-4-isopropylpiperazine hydrochloride (Compound 107)

In a similar manner to Example 5, a free base of Compound 107 was obtained using (E)-4-[2-(1H-indazol-3-yl)vinyl]benzoic acid (300 mg, 1.00 mmol) obtained in Step 6 of Example 1, 1-isopropylpiperazine (192 mg, 1.50 mmol), 1-hydroxybenzotriazole monohydrate (176 mg, 1.30 mmol), 1-ethyl-3-(3-dimethylaminopropyl)carbodiimide hydrochloride (270 mg, 1.40 mmol) and N-methylmorpholine (0.22 mL, 2.00 mmol), then the free base of Compound 107 was dissolved in methanol (2.00 mL), and the solution was added with 4 moL/L hydrogen chloride-methanol solution (1.50 mL), followed by stirring at room temperature for 30 minutes. The reaction mixture was concentrated under reduced pressure, and the residue was crystallized from acetone to obtain Compound 107 (24.5 mg, 5.5%).

$^1$H-NMR (270 MHz, DMSO-d$_6$) δ 1.28 (d, J=6.8 Hz, 6H), 3.15 (br, 1H), 3.33-3.41 (m, 8H), 7.23 (dd, J=7.9, 7.9 Hz, 1H), 7.41 (dd, J=8.3, 8.3 Hz, 1H), 7.52 (d, J=8.3 Hz, 2H), 7.57 (d, J=8.3 Hz, 1H), 7.61 (d, J=16.7 Hz, 1H), 7.67 (d, J=16.7 Hz, 1H), 7.82 (d, J=8.3 Hz, 2H), 8.21 (d, J=8.3 Hz, 1H), 10.0 (br, 1H). ESI-MS (m/z); 375 [M+H]$^+$

EXAMPLE 108

(E)-1-{4-[2-(1H-indazol-3-yl)vinyl]benzoyl}-4-[2-(dimethylamino)ethyl]piperazine, dihydrochloride (Compound 108)

In a similar manner to Example 5, a free base of Compound 108 was obtained using (E)-4-[2-(1H-indazol-3-yl)vinyl]benzoic acid (300 mg, 1.00 mmol) obtained in Step 6 of Example 1, 1-(2-dimethylaminoethyl)piperazine (235 mg, 1.50 mmol), 1-hydroxybenzotriazole monohydrate (176 mg, 1.30 mmol), 1-ethyl-3-(3-dimethylaminopropyl)carbodiimide hydrochloride (270 mg, 1.40 mmol) and N-methylmorpholine (0.22 mL, 2.00 mmol), then the free base of Compound 108 was dissolved in methanol (2.00 mL), and the solution was added with 4 moL/L hydrogen chloride-methanol solution (1.50 mL), followed by stirring at room temperature for 30 minutes. The reaction mixture was concentrated under reduced pressure, and the residue was crystallized from acetone to obtain Compound 108 (144 mg, 30%).

$^1$H-NMR (270 MHz, DMSO-d$_6$) δ 2.86 (s, 6H), 3.17-3.53 (m, 12H), 7.23 (dd, J=7.8, 7.8 Hz, 1H), 7.40 (dd, J=7.8, 7.8 Hz, 1H), 7.51 (d, J=8.3 Hz, 2H), 7.57 (d, J=8.3 Hz, 1H), 7.61 (d, J=16.7 Hz, 1H), 7.68 (d, J=16.7 Hz, 1H), 7.83 (d, J=8.3 Hz, 2H), 8.21 (d, J=8.3 Hz, 1H), 10.0 (br, 1H). ESI-MS (m/z); 404 [M+H]$^+$

EXAMPLE 109

(E)-1-{4-[2-(1H-indazol-3-yl)vinyl]benzoyl}-4-(2-methoxyethyl)piperazine hydrochloride (Compound 109)

(1H-indazol-3-ylmethyl)triphenylphosponioum bromide (473 mg, 1.00 mmol) was dissolved in methanol (10 mL), then a free base of Compound 109 was obtained using 4-[4-(2-methoxyethyl)piperazine-1-carbonyl]benzaldehyde (230 g, 0.83 mmol) and potassium carbonate (345 mg, 2.50 mmol). The free base of Compound 109 was dissolved in methanol (2.00 mL), and the solution was added with 4 moL/L hydrogen chloride-methanol solution (1.50 mL), followed by stirring at room temperature for 30 minutes. The reaction mixture was concentrated under reduced pressure, and the residue was crystallized from acetone to obtain Compound 109 (178 mg, 38%).

$^1$H-NMR (270 MHz, DMSO-d$_6$) δ 3.13-3.17 (m, 2H), 3.32 (s, 3H), 3.46 (br, 8H), 3.70-3.74 (m, 2H), 7.22 (dd, J=7.9, 7.9 Hz, 1H), 7.41 (dd, J=7.9, 7.9 Hz, 1H), 7.49 (d, J=8.2 Hz, 2H), 7.56 (d, J=16.8 Hz, 1H), 7.57 (d, J=8.2 Hz, 1H), 7.67 (d, J=16.8 Hz, 1H), 7.82 (d, J=8.2 Hz, 2H), 8.21 (d, J=8.2 Hz, 1H), 10.0 (br, 1H). APCI-MS (m/z); 391 [M+H]$^+$

EXAMPLE 110

(E)-N-[2-(ethylamino)ethyl]-4-[2-(1H-indazol-3-yl)vinyl]benzamide (Compound 110)

In a similar manner to Example 5, Compound 110 (40 mg, 12%) was obtained using (E)-4-[2-(1H-indazol-3-yl)vinyl]benzoic acid (300 mg, 1.00 mmol) obtained in Step 6 of Example 1, N-ethylethylenediamine (440 mg, 5.00 mmol), 1-hydroxybenzotriazole monohydrate (176 mg, 1.30 mmol), 1-ethyl-3-(3-dimethylaminopropyl)carbodiimide hydrochloride (270 mg, 1.40 mmol) and N-methylmorpholine (0.22 mL, 2.00 mmol).

$^1$H-NMR (270 MHz, DMSO-d$_6$) δ 1.03 (t, J=7.1 Hz, 3H), 2.52-2.60 (m, 2H), 2.68 (t, J=6.6 Hz, 2H), 3.32-3.36 (m, 3H), 7.22 (dd, J=7.1, 7.1 Hz, 1H), 7.41 (dd, J=7.1, 7.1 Hz, 1H), 7.56 (d, J=8.3 Hz, 1H), 7.57 (d, J=16.6 Hz, 1H), 7.68 (d, J=16.6 Hz, 1H), 7.80 (d, J=8.3 Hz, 2H), 7.88 (d, J=8.3 Hz, 2H), 8.22 (d, J=8.3 Hz, 1H), 8.40 (t, J=8.3 Hz, 1H), 13.2 (br, 1H). APCI-MS (m/z); 335 [M+H]$^+$

EXAMPLE 111

(E)-N-(2-aminoethyl)-4-[2-(1H-indazol-3-yl)vinyl]benzamide dihydrochloride (Compound 111)

The product obtained using (E)-4-[2-(1H-indazol-3-yl)vinyl]benzoic acid (300 mg, 1.00 mmol) obtained in Step 6 of Example 1, N-(2-aminoethyl)carbamic acid tert-butyl ester (240 mg, 1.50 mmol), 1-hydroxybenzotriazole monohydrate (176 mg, 1.30 mmol), 1-ethyl-3-(3-dimethylaminopropyl)

carbodiimide hydrochloride (270 mg, 1.40 mmol) and N-methylmorpholine (0.22 mL, 2.00 mmol) in a similar manner to Example 5, was dissolved in methanol (2.00 mL), and the solution was added with 4 moL/L hydrogen chloride-methanol solution (1.50 mL), followed by heating under reflux at 60° C. for 30 minutes. The reaction mixture was concentrated under reduced pressure, and the residue was crystallized from acetone to obtain Compound 111 (206 mg, 54%).

$^1$H-NMR (270 MHz, DMSO-$d_6$) δ 2.98-3.04 (m, 2H), 3.52-3.57 (m, 2H), 7.23 (dd, J=7.9, 7.9 Hz, 1H), 7.41 (dd, J=7.9, 7.9 Hz, 1H), 7.56 (d, J=8.3 Hz, 1H), 7.57 (d, J=16.7 Hz, 1H), 7.70 (d, J=16.7 Hz, 1H), 7.83 (d, J=8.3 Hz, 2H), 7.95 (d, J=8.3 Hz, 2H), 8.04 (br, 2H), 8.22 (d, J=8.3 Hz, 1H), 8.76 (t, J=5.3 Hz, 1H). ESI-MS (m/z); 307 [M+H]$^+$

EXAMPLE 112

(E)-N-[2-(methylamino)ethyl]-4-[2-(1H-indazol-3-yl)vinyl]benzamide hydrochloride (Compound 112)

In a similar manner to Example 5, a free base of Compound 112 was obtained using (E)-4-[2-(1H-indazol-3-yl)vinyl]benzoic acid (300 mg, 1.00 mmol) obtained in Step 6 of Example 1, N-methylethylenediamine (111 mg, 1.50 mmol), 1-hydroxybenzotriazole monohydrate (176 mg, 1.30 mmol), 1-ethyl-3-(3-dimethylaminopropyl)carbodiimide hydrochloride (270 mg, 1.40 mmol) and N-methylmorpholine (0.22 mL, 2.00 mmol), then the free base of Compound 112 was dissolved in methanol (2.00 mL), and the solution was added with 4 moL/L hydrogen chloride-methanol solution (1.50 mL), followed by stirring at room temperature for 30 minutes. The reaction mixture was concentrated under reduced pressure, and the residue was crystallized from acetone to obtain Compound 112 (105 mg, 29%).

$^1$H-NMR (270 MHz, DMSO-$d_6$) δ 2.58-2.61 (m, 3H), 3.11 (br, 2H), 3.56-3.63 (m, 2H), 7.23 (dd, J=7.9, 7.9 Hz, 1H), 7.41 (dd, J=8.3, 8.3 Hz, 1H), 7.56 (d, J=8.3 Hz, 1H), 7.57 (d, J=16.8 Hz, 1H), 7.70 (d, J=16.8 Hz, 1H), 7.83 (d, J=8.3 Hz, 2H), 7.96 (d, J=8.3 Hz, 2H), 8.22 (d, J=8.3 Hz, 1H), 8.80-8.84 (m, 2H). APCI-MS (m/z); 321 [M+H]$^+$

EXAMPLE 113

(E)-1-methoxyacetyl-4-{4-[2-(1H-indazol-3-yl)vinyl]benzoyl}homopiperazine (Compound 113)

In a similar manner to Example 5, Compound 113 (98 mg, 35%) was obtained using Compound 85 (285 mg, 0.68 mmol), methoxyacetic acid (0.05 ml, 0.62 mmol), 1-hydroxybenzotriazole monohydrate (110 mg, 0.81 mmol), 1-ethyl-3-(3-dimethylaminopropyl)carbodiimide hydrochloride (166 mg, 0.87 mmol) and N-methylmorpholine (0.34 mL, 3.10 mmol).

$^1$H-NMR (270 MHz, DMSO-$d_6$) δ 3.22-3.77 (m, 13H), 4.11 (br, 2H), 7.22 (dd, J=7.1, 7.1 Hz, 1H), 7.35-7.43 (m, 3H), 7.54 (d, J=16.8 Hz, 1H), 7.56 (d, J=8.4 Hz, 1H), 7.64 (d, J=16.8 Hz, 1H), 7.78 (d, J=8.1 Hz, 2H), 8.21 (d, J=8.1 Hz, 1H), 13.2 (br, 1H). ESI-MS (m/z); 419 [M+H]$^+$

EXAMPLE 114

(E)-1-(3-methyl-3-hydroxybutyryl)-4-{4-[2-(1H-indazol-3-yl)vinyl]benzoyl}homopiperazine (Compound 114)

In a similar manner to Example 5, Compound 114 (62 mg, 20%) was obtained using Compound 85 (285 mg, 0.68 mmol), β-hydroxyisovaleric acid (73 mg, 0.62 mmol), 1-hydroxybenzotriazole monohydrate (110 mg, 0.81 mmol), 1-ethyl-3-(3-dimethylaminopropyl)carbodiimide hydrochloride (166 mg, 0.87 mmol) and N-methylmorpholine (0.34 mL, 3.10 mmol).

$^1$H-NMR (270 MHz, DMSO-$d_6$) δ 1.12-1.19 (m, 6H), 1.91 (br, 1H), 3.53 (br, 12H), 7.22 (dd, J=7.4, 7.4 Hz, 1H), 7.32-7.44 (m, 3H), 7.54 (d, J=16.8 Hz, 1H), 7.56 (d, J=8.4 Hz, 1H), 7.64 (d, J=16.8 Hz, 1H), 7.78 (d, J=8.4 Hz, 2H), 8.21 (d, J=8.4 Hz, 1H), 13.2 (br, 1H). ESI-MS (m/z); 447 [M+H]$^+$

EXAMPLE 115

(E)-4-{4-[2-(1H-indazol-3-yl)vinyl]benzoyl}-1-(n-propyl)piperazin-2-one hydrochloride (Compound 115)

In a similar manner to Example 5, a free base of Compound 115 was obtained using (E)-4-[2-(1H-indazol-3-yl)vinyl]benzoic acid (260 mg, 0.87 mmol) obtained in Step 6 of Example 1, 1-n-propylpiperazin-2-one (309 mg, 1.74 mmol), 1-hydroxybenzotriazole monohydrate (153 mg, 1.13 mmol), 1-ethyl-3-(3-dimethylaminopropyl)carbodiimide hydrochloride (234 mg, 1.22 mmol) and N-methylmorpholine (0.50 mL, 4.35 mmol), then the free base of Compound 115 was dissolved in methanol (2.00 mL), and the solution was added with 4 moL/L hydrogen chloride-methanol solution (1.50 mL), followed by stirring at room temperature for 30 minutes. The reaction mixture was concentrated under reduced pressure, and the residue was crystallized from acetone to obtain Compound 115 (240 mg, 65%).

$^1$H-NMR (270 MHz, DMSO-$d_6$) δ 0.83 (t, J=7.4 Hz, 3H), 3.26-3.63 (m, 6H), 3.73 (br, 2H), 4.11 (br, 2H), 7.22 (dd, J=7.1, 7.1 Hz, 1H), 7.41 (dd, J=7.8, 7.8 Hz, 1H), 7.48 (d, J=8.4 Hz, 2H), 7.53 (d, J=7.1 Hz, 1H), 7.55 (d, J=16.7 Hz, 1H), 7.66 (d, J=16.7 Hz, 1H), 7.81 (d, J=8.4 Hz, 2H), 8.21 (d, J=8.4 Hz, 1H). APCI-MS (m/z); 389 [M+H]$^+$

EXAMPLE 116

(E)-4-{4-[2-(1H-indazol-3-yl)vinyl]benzoyl}-1-(sec-butyl)piperazin-2-one hydrochloride (Compound 116)

In a similar manner to Example 5, a free base of Compound 116 was obtained using (E)-4-[2-(1H-indazol-3-yl)vinyl]benzoic acid (128 mg, 0.42 mmol) obtained in Step 6 of Example 1, 1-sec-butylpiperazin-2-one (121 mg, 0.63 mmol), 1-hydroxybenzotriazole monohydrate (75 mg, 0.55 mmol), 1-ethyl-3-(3-dimethylaminopropyl)carbodiimide hydrochloride (115 mg, 0.59 mmol) and N-methylmorpholine (0.24 mL, 2.10 mmol), then the free base of Compound 116 was dissolved in methanol (2.00 mL), and the solution was added with 4 moL/L hydrogen chloride-methanol solution (1.50 mL), followed by stirring at room temperature for 30 minutes. The reaction mixture was concentrated under reduced pressure, and the residue was crystallized from acetone to obtain Compound 116 (74 mg, 40%).

$^1$H-NMR (270 MHz, DMSO-$d_6$) δ 0.78 (t, J=7.3 Hz, 3H), 1.05 (d, J=6.9 Hz, 3H), 1.34-1.47 (m, 2H), 3.23-3.32 (m, 1H), 4.39 (br, 6H), 7.21 (dd, J=8.1, 8.1 Hz, 1H), 7.40 (dd, J=8.1, 8.1 Hz, 1H), 7.48 (d, J=8.1 Hz, 2H), 7.53 (d, J=16.7 Hz, 1H), 7.55 (d, J=8.1 Hz, 1H), 7.65 (d, J=16.7 Hz, 1H), 7.80 (d, J=8.1 Hz, 2H), 8.20 (d, J=8.1 Hz, 1H). APCI-MS (m/z); 403 [M+H]$^+$

EXAMPLE 117

(E)-1-{4-[2-(1H-indazol-3-yl)vinyl]benzoyl}-1,2,3,6-tetrahydropyridine (Compound 117)

In a similar manner to Example 5, Compound 117 (196 mg, 72%) was obtained using (E)-4-[2-(1H-indazol-3-yl)vinyl]benzoic acid (250 mg, 0.83 mmol) obtained in Step 6 of Example 1, 1,2,3,6-tetrahydropyridine (0.11 ml, 1.25 mmol), 1-hydroxybenzotriazole monohydrate (146 mg, 1.08 mmol), 1-ethyl-3-(3-dimethylaminopropyl)carbodiimide hydrochloride (224 mg, 1.16 mmol) and N-methylmorpholine (0.18 mL, 1.66 mmol).

$^1$H-NMR (270 MHz, DMSO-d$_6$) δ 2.15 (br, 2H), 3.44-4.03 (m, 4H), 5.74-5.88 (m, 2H), 7.21 (dd, J=7.1, 7.1 Hz, 1H), 7.38 (d, J=8.1 Hz, 2H), 7.40-7.43 (m, 1H), 7.52 (d, J=8.1 Hz, 1H), 7.54 (d, J=16.6 Hz, 1H), 7.63 (d, J=16.6 Hz, 1H), 7.77 (d, J=8.1 Hz, 2H), 8.20 (d, J=8.1 Hz, 1H), 13.2 (br, 1H). APCI-MS (m/z); 330 [M+H]$^+$

EXAMPLE 118

(S)-(E)-4-methoxyacetyl-3-methyl-1-{4-[2-(1H-indazol-3-yl)vinyl]benzoyl}piperazine hydrochloride (Compound 118)

In a similar manner to Example 5, a free base of Compound 118 was obtained using Compound 101 (300 mg, 0.72 mmol), methoxyacetic acid (0.05 ml, 0.62 mmol), 1-hydroxybenzotriazole monohydrate (106 mg, 0.81 mmol), 1-ethyl-3-(3-dimethylaminopropyl)carbodiimide hydrochloride (161 mg, 0.87 mmol) and N-methylmorpholine (0.34 mL, 3.10 mmol), then the free base of Compound 118 was dissolved in methanol (2.00 mL), and the solution was added with 4 mol/L hydrogen chloride-methanol solution (1.50 mL), followed by stirring at room temperature for 30 minutes. The reaction mixture was concentrated under reduced pressure, and the residue was crystallized from acetone to obtain Compound 118 (87 mg, 27%).

$^1$H-NMR (270 MHz, DMSO-d$_6$) δ 1.08-1.15 (m, 3H), 3.29 (s, 3H), 4.04 (br, 9H), 7.22 (dd, J=7.4, 7.4 Hz, 1H), 7.40 (d, J=8.4 Hz, 2H), 7.38-7.45 (m, 1H), 7.53 (d, J=8.4 Hz, 1H), 7.55 (d, J=16.6 Hz, 1H), 7.65 (d, J=16.6 Hz, 1H), 7.80 (d, J=8.4 Hz, 2H), 8.21 (d, J=8.4 Hz, 1H). APCI-MS (m/z); 419 [M+H]$^+$

EXAMPLE 119

(S)-(E)-4-(3-methyl-3-hydroxybutyryl)-3-methyl-1-{4-[2-(1H-indazol-3-yl)vinyl]benzoyl}piperazine hydrochloride (Compound 119)

In a similar manner to Example 5, a free base of Compound 119 was obtained using Compound 101 (500 mg, 1.19 mmol), β-hydroxyisovaleric acid (0.12 mg, 0.99 mmol), 1-hydroxybenzotriazole monohydrate (174 mg, 1.29 mmol), 1-ethyl-3-(3-dimethylaminopropyl)carbodiimide hydrochloride (270 mg, 1.39 mmol) and N-methylmorpholine (0.50 mL, 4.46 mmol), then the free base of Compound 119 was dissolved in methanol (2.00 mL), and the solution was added with 4 mol/L hydrogen chloride-methanol solution (1.50 mL), followed by stirring at room temperature for 30 minutes. The reaction mixture was concentrated under reduced pressure, and the residue was crystallized from acetone to obtain Compound 119 (237 mg, 41%).

$^1$H-NMR (270 MHz, DMSO-d$_6$) δ 1.04-1.18 (m, 9H), 2.30 (br, 1H), 4.02 (br, 9H), 7.22 (dd, J=7.9, 7.9 Hz, 1H), 7.39 (d, J=8.2 Hz, 2H), 7.38-7.46 (m, 1H), 7.53 (d, J=8.2 Hz, 1H), 7.55 (d, J=16.6 Hz, 1H), 7.65 (d, J=16.6 Hz, 1H), 7.80 (d, J=8.2 Hz, 2H), 8.21 (d, J=8.2 Hz, 1H). APCI-MS (m/z); 447 [M+H]$^+$

EXAMPLE 120

(E)-4-[2-(1H-indazol-3-yl)vinyl]-N-(piperidin-4-yl)benzamide dihydrochloride (Compound 120)

The product obtained using (E)-4-[2-(1H-indazol-3-yl)vinyl]benzoic acid (500 mg, 1.66 mmol) obtained in Step 6 of Example 1, 1-tert-butoxycarbonyl-4-aminopiperidine (500 mg, 2.49 mmol), 1-hydroxybenzotriazole monohydrate (291 mg, 2.16 mmol), 1-ethyl-3-(3-dimethylaminopropyl)carbodiimide hydrochloride (450 mg, 2.32 mmol) and N-methylmorpholine (0.37 mL, 3.32 mmol) in a similar manner to Example 5, was dissolved in methanol (2.00 mL), and the solution was added with 4 mol/L hydrogen chloride-methanol solution (1.50 mL), followed by heating under reflux at 60° C. for 30 minutes. The reaction mixture was concentrated under reduced pressure, and the residue was crystallized from acetone to obtain Compound 120 (337 mg, 48%).

$^1$H-NMR (270 MHz, DMSO-d$_6$) δ 1.78-1.85 (m, 2H), 1.96-2.09 (m, 2H), 3.00-3.03 (m, 2H), 3.30-3.34 (m, 2H), 4.07 (br, 1H), 7.22 (dd, J=7.2, 7.2 Hz, 1H), 7.41 (dd, J=8.4, 8.4 Hz, 1H), 7.56 (d, J=16.8 Hz, 1H), 7.73 (d, J=16.8 Hz, 1H), 7.81 (d, J=8.4 Hz, 2H), 7.91 (d, J=8.4 Hz, 2H), 8.22 (d, J=8.4 Hz, 1H), 8.50 (d, J=7.2 Hz, 1H), 8.86 (br, 1H). APCI-MS (m/z); 347 [M+H]$^+$

EXAMPLE 121

(E)-1-{4-[2-(1H-indazol-3-yl)vinyl]benzoyl}-4-[2-oxo-2-(pyrrolidin-1-yl)ethyl]piperazine (Compound 121)

The crude product obtained using (E)-4-[2-(1H-indazol-3-yl)vinyl]benzoic acid (300 mg, 1.14 mmol) obtained in Step 6 of Example 1, N-methylmorpholine (0.25 mL, 2.28 mmol), 1-ethyl-3-(3-dimethylaminopropyl)carbodiimide hydrochloride (305 mg, 1.59 mmol), 1-hydroxybenzotriazole monohydrate (200 mg, 1.48 mmol) and 2-(piperazin-1-yl)-1-(pyrrolidin-1-yl)ethanone (337 mg, 1.71 mmol) in a similar manner to Step 7 of example 1, was triturated in mixed solvent of ethyl acetate/methanol to obtain Compound 121 (298 mg, 60%).

$^1$H-NMR (270 MHz, DMSO-d$_6$) δ 1.72-1.91 (m, 4H), 3.28 (t, J=6.5 Hz, 2H), 3.45 (t, J=6.5 Hz, 2H), 3.40-7.70 (br, 8H), 7.22 (t, J=7.8 Hz, 1H), 7.38 (t, J=7.8 Hz, 1H), 7.41 (d, J=8.1 Hz, 2H), 7.54 (d, J=16.7 Hz, 1H), 7.56 (d, J=8.4 Hz, 1H), 7.64 (d, J=16.7 Hz, 1H), 7.78 (d, J=8.1 Hz, 2H), 8.21 (d, J=8.4 Hz, 1H), 13.22 (s, 1H). APCI-MS (m/z); 444 [M]$^+$

EXAMPLE 122

(E)-1-{4-[2-(1H-indazol-3-yl)vinyl]benzoyl}-3-aminopyrrolidine dihydrochloride (Compound 122)

The product obtained using (E)-4-[2-(1H-indazol-3-yl)vinyl]benzoic acid (800 mg, 2.66 mmol) obtained in Step 6 of Example 1, (pyrrolidin-3-yl)carbamic acid tert-butyl ester (1.00 g, 5.32 mmol), 1-hydroxybenzotriazole monohydrate (470 mg, 3.46 mmol), 1-ethyl-3-(3-dimethylaminopropyl)carbodiimide hydrochloride (720 mg, 3.72 mmol) and N-methylmorpholine (0.58 mL, 5.32 mmol) in a similar manner to Example 5, was dissolved in methanol (5.00 mL), and the solution was added with 4 moL/L hydrogen chloride-methanol solution (2.00 mL), followed by heating under reflux at 60° C. for 1 hour. The reaction mixture was concentrated under reduced pressure, and the residue was crystallized from acetone to obtain Compound 122 (398 mg, 38%).

$^1$H-NMR (270 MHz, DMSO-$d_6$) δ 2.23 (br, 1H), 3.54-3.87 (m, 6H), 7.22 (dd, J=7.7, 7.7 Hz, 1H), 7.41 (dd, J=7.7, 7.7 Hz, 1H), 7.54 (d, J=8.3 Hz, 2H), 7.55 (d, J=8.3 Hz, 1H), 7.57 (d, J=16.8 Hz, 1H), 7.66 (d, J=16.8 Hz, 1H), 7.80 (d, J=8.3 Hz, 2H), 8.21 (d, J=8.3 Hz, 1H), 8.30 (br, 1H), 8.42 (br, 1H). APCI-MS (m/z); 333 [M+H]$^+$

EXAMPLE 123

(S)-(E)-1-{4-[2-(1H-indazol-3-yl)vinyl]benzoyl}-4-(2-amino-3-hydroxypropionyl)piperazine dihydrochloride (Compound 123)

The product obtained using Compound 18 (300 mg, 0.90 mmol), N-(tert-butoxycarbonyl)-L-serine (155 mg, 0.76 mmol), 1-hydroxybenzotriazole monohydrate (133 mg, 0.99 mmol), 1-ethyl-3-(3-dimethylaminopropyl)carbodiimide hydrochloride (204 mg, 1.06 mmol) and N-methylmorpholine (0.17 mL, 1.52 mmol) in a similar manner to Example 5, was dissolved in methanol (2.00 mL), and the solution was added with 4 moL/L hydrogen chloride-methanol solution (1.50 mL), followed by heating under reflux at 60° C. for 30 minutes. The reaction mixture was concentrated under reduced pressure, and the residue was crystallized from acetone to obtain Compound 123 (290 mg, 78%).

$^1$H-NMR (270 MHz, DMSO-$d_6$) δ 3.63-3.73 (m, 8H), 4.43 (br, 1H), 4.95 (br, 3H), 7.22 (dd, J=7.7, 7.7 Hz, 1H), 7.41 (dd, J=8.2, 8.2 Hz, 1H), 7.48 (d, J=8.2 Hz, 2H), 7.53 (d, J=8.2 Hz, 1H), 7.56 (d, J=16.8 Hz, 1H), 7.66 (d, J=16.8 Hz, 1H), 7.81 (d, J=8.2 Hz, 2H), 8.20-8.23 (m, 3H). APCI-MS (m/z); 420 [M+H]$^+$

EXAMPLE 124

(S)-(E)-1-{4-[2-(1H-indazol-3-yl)vinyl]benzoyl}-4-(pyrrolidin-3-ylcarbonyl)piperazine dihydrochloride (Compound 124)

The product obtained using Compound 18 (300 mg, 0.90 mmol), (S)-pyrrolidin-1,3-dicarboxylic acid 1-tert-butyl ester (162 mg, 0.76 mmol), 1-hydroxybenzotriazole monohydrate (133 mg, 0.99 mmol), 1-ethyl-3-(3-dimethylaminopropyl)carbodiimide hydrochloride (204 mg, 1.06 mmol) and N-methylmorpholine (0.17 mL, 1.52 mmol) in a similar manner to Example 5, was dissolved in methanol (2.00 mL), and the solution was added with 4 moL/L hydrogen chloride-methanol solution (1.50 mL), followed by heating under reflux at 60° C. for 30 minutes. The reaction mixture was concentrated under reduced pressure, and the residue was crystallized from acetone to obtain Compound 124 (278 mg, 61%).

$^1$H-NMR (270 MHz, DMSO-$d_6$) δ 1.78-1.94 (m, 2H), 2.40 (br, 1H), 3.15-3.26 (m, 2H), 3.58 (br, 8H), 4.60 (br, 2H), 7.22 (dd, J=7.1, 7.1 Hz, 1H), 7.41 (dd, J=8.2, 8.2 Hz, 1H), 7.47 (d, J=8.2 Hz, 2H), 7.54 (d, J=8.2 Hz, 1H), 7.56 (d, J=16.6 Hz, 1H), 7.66 (d, J=16.6 Hz, 1H), 7.82 (d, J=8.2 Hz, 2H), 8.21 (d, J=8.2 Hz, 1H) 9.96-9.98 (m, 1H). APCI-MS (m/z); 430 [M+H]$^+$

EXAMPLE 125

(E)-4-dimethylaminoacetyl-1-{4-[2-(1H-indazol-3-yl)vinyl]benzoyl}piperazine (Compound 125)

In a similar manner to Example 5, Compound 125 (77 mg, 31%) was obtained using Compound 18 (200 mg, 0.60 mmol), N,N-dimethylglycine (70 mg, 0.50 mmol), 1-hydroxybenzotriazole monohydrate (88 mg, 0.65 mmol), 1-ethyl-3-(3-dimethylaminopropyl)carbodiimide hydrochloride (134 mg, 0.70 mmol) and N-methylmorpholine (0.11 mL, 1.00 mmol).

$^1$H-NMR (270 MHz, DMSO-$d_6$) δ 2.17 (s, 6H), 3.08 (br, 2H), 3.50-3.58 (m, 8H), 7.21 (dd, J=7.1, 7.1 Hz, 1H), 7.37-7.46 (m, 1H), 7.47 (d, J=8.2 Hz, 2H), 7.52 (d, J=8.2 Hz, 1H), 7.54 (d, J=16.6 Hz, 1H), 7.64 (d, J=16.6 Hz, 1H), 7.79 (d, J=8.1 Hz, 2H), 8.20 (d, J=8.2 Hz, 1H), 13.2 (br, 1H). APCI-MS (m/z); 418 [M+H]$^+$

EXAMPLE 126

(E)-4-[(isobutyrylamino)acetyl]-1-{4-[2-(1H-indazol-3-yl)vinyl]benzoyl}piperazine (Compound 126)

The crude product (174 mg) obtained using Compound 18 (200 mg, 0.602 mmol), N-methylmorpholine (0.132 mL, 1.20 mmol), 1-ethyl-3-(3-dimethylaminopropyl)carbodiimide hydrochloride (161 mg, 0.842 mmol), 1-hydroxybenzotriazole monohydrate (106 mg, 0.783 mmol) and (3-methylbutyrylamino)acetic acid (115 mg, 0.722 mmol) in a similar manner to Example 5, was purified by silica gel column chromatography (chloroform/methanol=80/20), followed by triturating in mixed solvent of ethyl acetate/ethanol to obtain Compound 126 (105 mg, 37%).

$^1$H-NMR (300 MHz, DMSO-$d_6$) δ 0.89 (d, J=6.0 Hz, 6H), 1.90-2.08 (m, 3H), 3.25-3.75 (br, 8H), 3.80-4.04 (br.s, 2H), 7.22 (t, J=6.9 Hz, 1H), 7.41 (t, J=6.9 Hz, 1H), 7.46 (d, J=8.1 Hz, 2H), 7.56 (d, J=16.8 Hz, 1H), 7.57 (d, J=7.8 Hz, 1H), 7.66 (d, J=16.8 Hz, 1H), 7.80 (d, J=8.1 Hz, 2H), 7.91 (br, 1H), 8.21 (d, J=7.8 Hz, 1H), 13.22 (s, 1H). APCI-MS (m/z); 474 [M]$^+$

EXAMPLE 127

(E)-4-[(2-methoxyethoxy)acetyl]-1-{4-[2-(1H-indazol-3-yl)vinyl]benzoyl}piperazine (Compound 127)

The crude product obtained using Compound 18 (200 mg, 0.602 mmol), N-methylmorpholine (0.132 mL, 1.20 mmol), 1-ethyl-3-(3-dimethylaminopropyl)carbodiimide hydrochloride (161 mg, 0.842 mmol), 1-hydroxybenzotriazole monohydrate (106 mg, 0.783 mmol) and 2-methoxyethoxyacetic acid (0.0674 mL, 0.722 mmol) in a similar manner to Example 5, was purified by silica gel column chromatography (chloroform/methanol=80/20) to obtain Compound 127 (0.011 g, 4%).

$^1$H-NMR (270 MHz, DMSO-$d_6$) δ 3.25 (s, 3H), 3.40-3.65 (m, 12H), 4.18 (s, 1H), 7.22 (t, J=8.1 Hz, 1H), 7.41 (t, J=8.1 Hz, 1H), 7.45 (d, J=7.9 Hz, 2H), 7.55 (d, J=16.4 Hz, 1H), 7.56 (d, J=8.6 Hz, 1H), 7.65 (d, J=16.4 Hz, 1H), 7.80 (d, J=7.9 Hz, 2H), 8.21 (d, J=8.6 Hz, 1H), 13.21 (s, 1H). APCI-MS (m/z); 449 [M]$^+$

EXAMPLE 128

(E)-4-ethoxyacetyl-1-{4-[2-(1H-indazol-3-yl)vinyl]benzoyl}piperazine (Compound 128)

The crude product obtained using dihydrochloride of Compound 18 (300 mg, 0.741 mmol), N-methylmorpholine (0.163 mL, 1.48 mmol), 1-ethyl-3-(3-dimethylaminopropyl)

carbodiimide hydrochloride (199 mg, 1.04 mmol), 1-hydroxybenzotriazole monohydrate (130 mg, 0.963 mmol) and ethoxyacetic acid (0.0700 mL, 0.741 mmol) in a similar manner to Example 5, was purified by silica gel column chromatography (chloroform/methanol=90/10), followed by recrystallization from mixed solvent of ethyl acetate/methanol to obtain Compound 128 (62.0 mg, 20%).

$^1$H-NMR (300 MHz, DMSO-$d_6$) δ 1.13 (t, J=6.9 Hz, 3H), 3.40-3.65 (br, 8H), 3.47 (q, J=6.9 Hz, 2H), 4.13 (brs, 2H), 7.22 (t, J=7.5 Hz, 1H), 7.41 (t, J=7.5 Hz, 1H), 7.46 (d, J=8.1 Hz, 2H), 7.55 (d, J=16.8 Hz, 1H), 7.56 (d, J=8.4 Hz, 1H), 7.65 (d, J=16.8 Hz, 1H), 7.80 (d, J=8.1 Hz, 2H), 8.21 (d, J=8.4 Hz, 1H), 13.22 (s, 1H). APCI-MS (m/z); 419 [M]$^+$

EXAMPLE 129

(E)-4-(3-aminopropionyl)-1-{4-[2-(1H-indazol-3-yl)vinyl]benzoyl}piperazine dihydrochloride (Compound 129)

In a similar manner to Example 5, the product obtained using Compound 18 (300 mg, 0.90 mmol), 3-(tert-butoxycarbonylamino)propionic acid (143 mg, 0.75 mmol), 1-hydroxybenzotriazole monohydrate (132 mg, 0.98 mmol), 1-ethyl-3-(3-dimethylaminopropyl)carbodiimide hydrochloride (202 mg, 1.05 mmol) and N-methylmorpholine (0.16 mL, 1.50 mmol) was dissolved in methanol (2.00 mL), and the solution was added with 4 moL/L hydrogen chloride-methanol solution (1.50 mL), followed by heating under reflux at 60° C. for 40 minutes. The reaction mixture was concentrated under reduced pressure, and the residue was crystallized from acetone to obtain Compound 129 (0.11 mg, 24%).

$^1$H-NMR (270 MHz, DMSO-$d_6$) δ 2.70-2.75 (m, 2H), 3.01-3.03 (m, 2H), 3.56 (br, 8H), 7.22 (dd, J=7.9, 7.9 Hz, 1H), 7.40 (dd, J=7.9, 7.9 Hz, 1H), 7.47 (d, J=8.1 Hz, 2H), 7.54 (d, J=7.9 Hz, 1H), 7.55 (d, J=16.8 Hz, 1H), 7.65 (d, J=16.8 Hz, 1H), 7.62-7.69 (m, 2H), 7.81 (d, J=8.2 Hz, 2H), 8.20 (d, J=8.2 Hz, 1H). APCI-MS (m/z); 404 [M+H]$^+$

EXAMPLE 130

(E)-4-[(phenylacetylamino)acetyl]-1-{4-[2-(1H-indazol-3-yl)vinyl]benzoyl}piperazine (Compound 130)

In a similar manner to Example 5, Compound 130 (0.21 mg, 46%) was obtained using Compound 18 (366 mg, 0.90 mmol), phenaceturic acid (175 mg, 0.90 mmol), 1-hydroxybenzotriazole monohydrate (132 mg, 0.98 mmol), 1-ethyl-3-(3-dimethylaminopropyl)carbodiimide hydrochloride (202 mg, 1.05 mmol) and N-methylmorpholine (0.16 mL, 1.50 mmol).

$^1$H-NMR (270 MHz, DMSO-$d_6$) 3.56 (br, 10H), 3.99-4.00 (m, 2H), 7.18-7.33 (m, 6H), 7.38-7.41 (m, 1H), 7.45 (d, J=8.4 Hz, 2H), 7.55 (d, J=16.6 Hz, 1H), 7.65 (d, J=16.6 Hz, 1H), 7.80 (d, J=8.4 Hz, 2H), 8.16 (t, J=5.4 Hz, 1H), 8.21 (d, J=8.4 Hz, 1H) 13.2 (br, 1H).

APCI-MS (m/z); 508 [M+H]$^+$

EXAMPLE 131

(E)-4-(2-amino-2-methylpropionyl)-1-{4-[2-(1H-indazol-3-yl)vinyl]benzoyl}piperazine dihydrochrolide (Compound 131)

The product obtained using Compound 18 (300 mg, 0.90 mmol), 2-(tert-butoxycarbonyl)amino-2-methylpropionic acid (153 mg, 0.75 mmol), 1-hydroxybenzotriazole monohydrate (132 mg, 0.98 mmol), 1-ethyl-3-(3-dimethylaminopropyl)carbodiimide hydrochloride (202 mg, 1.05 mmol) and N-methylmorpholine (0.16 mL, 1.50 mmol) in a similar manner to Example 5, was dissolved in methanol (2.00 mL), and the solution was added with 4 moL/L hydrogen chloride-methanol solution (1.50 mL), followed by heating under reflux at 60° C. for 30 minutes. The reaction mixture was concentrated under reduced pressure, and the residue was crystallized from acetone to obtain Compound 131 (0.10 mg, 23%).

$^1$H-NMR (270 MHz, DMSO-$d_6$) δ 1.57 (br, 6H), 3.65 (br, 4H), 4.36 (br, 4H), 7.22 (dd, J=7.9, 7.9 Hz, 1H), 7.41 (dd, J=8.4, 8.4 Hz, 1H), 7.47 (d, J=8.4 Hz, 2H), 7.54 (d, J=7.9 Hz, 1H), 7.55 (d, J=16.6 Hz, 1H), 7.66 (d, J=16.6 Hz, 1H), 7.81 (d, J=8.4 Hz, 2H), 8.21 (d, J=8.4 Hz, 1H), 8.27 (br, 2H). APCI-MS (m/z); 418 [M+H]$^+$

EXAMPLE 132

(E)-4-dimethylcarbamoylamino-1-{4-[2-(1H-indazol-3-yl)vinyl]benzoyl}piperidine (Compound 132)

The crude product obtained using (E)-4-[2-(1H-indazol-3-yl)vinyl]benzoic acid (200 mg, 0.76 mmol) obtained in Step 6 of Example 1, 1,1-dimethyl-3-(piperidin-4-yl)urea (0.20 ml, 1.14 mmol), 1-hydroxybenzotriazole monohydrate (133 mg, 1.00 mmol), 1-ethyl-3-(3-dimethylaminopropyl)carbodiimide hydrochloride (204 mg, 1.06 mmol) and N-methylmorpholine (0.18 mL, 1.66 mmol) in a similar manner to Example 5, was crystallized from ethyl acetate to obtain Compound 132 (195 mg, 62%).

$^1$H-NMR (270 MHz, DMSO-$d_6$) δ 1.38 (br, 2H), 1.75 (br, 2H), 2.77 (s, 6H), 3.02 (br, 2H), 3.69 (br, 2H), 4.30 (br, 1H), 6.01 (d, J=7.4 Hz, 1H), 7.22 (dd, J=7.4, 7.4 Hz, 1H), 7.38-7.41 (m, 1H), 7.45 (d, 2H, J=8.4 Hz), 7.53 (d, J=7.4 Hz, 1H), 7.55 (d, J=16.8 Hz, 1H), 7.65 (d, J=16.8 Hz, 1H), 7.80 (d, J=8.4 Hz, 2H), 8.21 (d, J=8.4 Hz, 1H) 13.2 (br, 1H). ESI-MS (m/z); 418 [M+H]$^+$

EXAMPLE 134

(E)-4-{4-[2-(1H-indazol-3-yl)vinyl]benzoyl}-1-(2-methoxyethyl)piperazin-2-one hydrochloride (Compound 134)

The crude product obtained using (E)-4-[2-(1H-indazol-3-yl)vinyl]benzoic acid (50.0 mg, 0.189 mmol) obtained in Step 6 of Example 1, N-methylmorpholine (0.0415 mL, 0.378 mmol), 1-ethyl-3-(3-dimethylaminopropyl)carbodiimide hydrochloride (50.7 mg, 0.265 mmol), 1-hydroxybenzotriazole monohydrate (33.2 mg, 0.246 mmol) and 1-(2-methoxyethyl)piperazin-2-one (44.8 mg, 0.284 mmol) in a similar manner to Step 7 of Example 1, was treated with hydrogen chloride-ethyl acetate solution (4 mol/L, 0.236 mL) to obtain Compound 134 (10.0 mg, 12%).

$^1$H-NMR (270 MHz, DMSO-$d_6$) δ 3.26 (s, 3H), 3.40-3.55 (m, 4H), 3.60-4.20 (br, 6H), 7.22 (t, J=7.0 Hz, 1H), 7.40 (t, J=7.0 Hz, 1H), 7.48 (d, J=7.4 Hz, 2H), 7.55 (d, J=17.0 Hz, 1H), 7.56 (d, J=7.6 Hz, 1H), 7.66 (d, J=17.0 Hz, 1H), 7.81 (d, J=7.4 Hz, 2H), 8.21 (d, J=7.6 Hz, 1H). APCI-MS (m/z); 405 [M+H]$^+$

EXAMPLE 135

(E)-1-{4-[2-(1H-indazol-3-yl)vinyl]benzoyl}-4-[2-oxo-2-(isopropylamino)ethyl]piperazine dihydrochloride (Compound 135)

The crude product obtained using (E)-4-[2-(1H-indazol-3-yl)vinyl]benzoic acid (200 mg, 0.757 mmol) obtained in Step 6 of Example 1, N-methylmorpholine (0.166 mL, 1.51 mmol), 1-ethyl-3-(3-dimethylaminopropyl)carbodiimide hydrochloride (203 mg, 1.06 mmol), 1-hydroxybenzotriazole monohydrate (133 mg, 0.984 mmol) and N-isopropyl-2-(piperazin-1-yl)acetamide (210 mg, 1.14 mmol) in a similar manner to Step 7 of Example 1, was purified by silica gel column chromatography (chloroform/methanol=80/20), followed by treating with 4 mol/L hydrogen chloride-ethyl acetate solution (0.665 mL) to obtain Compound 135 (99.7 mg, 26%).

$^1$H-NMR (300 MHz, DMSO-$d_6$) δ 1.10 (d, J=6.9 Hz, 1H), 3.20-3.65 (br, 8H), 3.95 (s, 2H), 4.03 (q, J=6.9 Hz, 1H), 7.41 (t, J=7.8 Hz, 1H), 7.50 (d, J=8.4 Hz, 2H), 7.56 (d, J=16.5 Hz, 1H), 7.58 (d, J=8.1 Hz, 1H), 7.67 (d, J=16.5 Hz, 1H), 7.82 (d, J=8.4 Hz, 2H), 8.22 (d, J=8.1 Hz, 1H), 8.67 (d, J=7.5 Hz, 1H), 10.61 (brs, 1H). APCI-MS (m/z); 432 [M+H]$^+$

EXAMPLE 136

(E)-4-(3-hydroxy-2-hydroxymethyl-2-methylpropionyl)-1-{4-[2-(1H-indazol-3-yl)vinyl]benzoyl}piperazine hydrochloride (Compound 136)

The crude product obtained using dihydrochloride of Compound (300 mg, 0.741 mmol), N-methylmorpholine (0.163 mL, 1.48 mmol), 1-ethyl-3-(3-dimethylaminopropyl)carbodiimide hydrochloride (199 mg, 1.04 mmol), 1-hydroxybenzotriazole monohydrate (130 mg, 0.963 mmol) and 3-hydroxy-2-hydroxymethyl-2-methylpropionic acid (99.4 mg, 0.741 mmol) in a similar manner to Example 5, was purified by silica gel column chromatography (chloroform/methanol=80/20), followed by treating with 10% hydrogen chloride-methanol solution (0.932 mL) and tritirating in acetone to obtain Compound 136 (10.0 mg, 3%).

$^1$H-NMR (300 MHz, DMSO-$d_6$) δ 3.17 (brs, 3H), 3.60-3.85 (br, 4H), 4.00-4.45 (br, 8H), 7.22 (t, J=7.2 Hz, 1H), 7.41 (t, J=7.2 Hz, 1H), 7.50 (d, J=8.4 Hz, 2H), 7.56 (d, J=16.5 Hz, 1H), 7.57 (d, J=8.1 Hz, 1H), 7.66 (d, J=16.5 Hz, 1H), 7.81 (d, J=8.4 Hz, 2H), 8.21 (d, J=8.1 Hz, 1H), 9.14 (br.s, 1H).

EXAMPLE 137

(E)-4-[4-(acetylamino)butyryl]-1-{4-[2-(1H-indazol-3-yl)vinyl]benzoyl}piperazine (Compound 137)

In a similar manner to Example 5, Compound 137 (0.12 mg, 52%) was obtained using dihydrochloride of Compound 18 (200 mg, 0.49 mmol), 4-acetylaminobutyric acid (72 mg, 0.49 mmol), 1-hydroxybenzotriazole monohydrate (87 mg, 0.64 mmol), 1-ethyl-3-(3-dimethylaminopropyl)carbodiimide hydrochloride (133 mg, 0.69 mmol) and N-methylmorpholine (0.11 mL, 0.98 mmol).

$^1$H-NMR (270 MHz, DMSO-$d_6$) δ 1.63 (t, J=6.9 Hz, 2H), 1.79 (s, 3H), 2.31-2.34 (m, 2H), 3.04 (q, J=6.9 Hz, 2H), 3.51 (br, 8H), 7.22 (dd, J=7.4, 7.4 Hz, 1H), 7.38-7.41 (m, 1H), 7.45 (d, J=8.4 Hz, 2H), 7.53 (d, J=7.4 Hz, 1H), 7.55 (d, J=16.8 Hz, 1H), 7.65 (d, J=16.8 Hz, 1H), 7.80 (d, J=8.4 Hz, 2H), 8.21 (d, J=8.4 Hz, 1H), 13.2 (br, 1H). ESI-MS (m/z); 460 [M+H]$^+$

EXAMPLE 138

(E)-4-(N-acetyl-N-methylaminoacetyl)-1-{4-[2-(1H-indazol-3-yl)vinyl]benzoyl}piperazine (Compound 138)

The crude product obtained using dihydrochloride of Compound 18 (300 mg, 0.741 mmol), N-methylmorpholine (0.163 mL, 1.48 mmol), 1-ethyl-3-(3-dimethylaminopropyl) carbodiimide hydrochloride (199 mg, 1.04 mmol), 1-hydroxybenzotriazole monohydrate (130 mg, 0.963 mmol) and N-acetylsarcosine (77.7 mg, 0.593 mmol) In a similar manner to Example 5, was purified by silica gel column chromatography (chloroform/methanol=90/10), followed by triturating in mixed solvent of ethyl acetate/methanol to obtain Compound 138 (54.8 mg, 25%).

$^1$H-NMR (270 MHz, DMSO-$d_6$) δ 2.02 (s, 3H), 2.97 (s, 3H), 3.42-3.60 (br, 8H), 4.18 (s, 2H), 7.22 (t, J=7.6 Hz, 1H), 7.41 (d, J=7.6 Hz, 1H), 7.46 (d, J=8.1 Hz, 2H), 7.55 (d, J=16.7 Hz, 1H), 7.56 (d, J=8.1 Hz, 1H), 7.66 (d, J=16.7 Hz, 1H), 7.80 (d, J=8.1 Hz, 2H), 8.21 (d, J=8.1 Hz, 1H), 13.21 (s, 1H). APCI-MS (m/z); 446 [M]$^+$

EXAMPLE 139

(E)-4-{4-[2-(1H-indazol-3-yl)vinyl]benzoyl}-1-(cyclopropyl)piperazine-2,6-dione (Compound 139)

In a similar manner to Example 5, Compound 139 (64 mg, 28%) was obtained using (E)-4-[2-(1H-indazol-3-yl)vinyl]benzoic acid (150 mg, 0.57 mmol) obtained in Step 6 of Example 1, 1-(cyclopropyl)piperazine-2,6-dione (100 mg, 0.86 mmol), 1-hydroxybenzotriazole monohydrate (100 mg, 0.74 mmol), 1-ethyl-3-(3-dimethylaminopropyl)carbodiimide hydrochloride (153 mg, 0.80 mmol) and N-methylmorpholine (0.13 mL, 1.14 mmol).

$^1$H-NMR (270 MHz, DMSO-$d_6$) δ 0.57-0.64 (m, 2H), 0.86-0.94 (m, 2H), 2.43-2.49 (m, 1H), 4.44 (br, 4H), 7.23 (dd, J=7.2, 7.2 Hz, 1H), 7.41 (dd, J=7.2, 7.2 Hz, 1H), 7.49 (d, J=8.2 Hz, 2H), 7.56 (d, J=16.8 Hz, 1H), 7.57 (d, J=8.2 Hz, 1H), 7.68 (d, J=16.8 Hz, 1H), 7.83 (d, J=8.2 Hz, 2H), 8.21 (d, J=8.2 Hz, 1H), 13.2 (br, 1H). APCI-MS (m/z); 401 [M+H]$^+$

EXAMPLE 140

(S)-(E)-4-[(pyrrolidin-2-yl)carbonyl]-1-{4-[2-(1H-indazol-3-yl)vinyl]benzoyl}piperazine (Compound 140)

The product obtained using dihydrochloride of Compound 18 (100 mg, 0.25 mmol), N-(tert-butoxycarbonyl)-L-proline (53 mg, 0.25 mmol), 1-hydroxybenzotriazole monohydrate (43 mg, 0.33 mmol), 1-ethyl-3-(3-dimethylaminopropyl)carbodiimide hydrochloride (66 mg, 0.35 mmol) and N-methylmorpholine (0.06 mL, 0.50 mmol) in a similar manner to Example 5, was dissolved in methanol (2.00 mL), and the solution was added with 4 mol/L hydrogen chloride-methanol solution (1.50 mL) followed by heating under reflux at 60° C. for 30 minutes. The reaction mixture was concentrated under reduced pressure, and the residue was added with saturated sodium hydrogencarbonate solution and ethyl acetate, followed by extraction. The crude product was crystallized from acetone to obtain Compound 140 (21 mg, 20%).

$^1$H-NMR (270 MHz, DMSO-$d_6$) δ 1.85-1.91 (m, 4H), 2.32-2.36 (m, 2H), 3.14-3.21 (m, 4H), 3.57 (br, 4H), 4.52 (br, 1H), 7.22 (dd, J=7.4, 7.4 Hz, 1H), 7.41 (dd, J=8.2, 8.2 Hz, 1H), 7.47 (d, J=8.2 Hz, 2H), 7.53 (d, J=7.4 Hz, 1H), 7.56 (d, J=16.6 Hz, 1H), 7.66 (d, J=16.6 Hz, 1H), 7.81 (d, J=8.2 Hz, 2H), 8.21 (d, J=8.2 Hz, 1H), 13.2 (br, 1H). APCI-MS (m/z); 430 [M+H]$^+$

EXAMPLE 141

(E)-4-{4-[2-(1H-indazol-3-yl)vinyl]benzoyl}-1-(2-methoxyethyl)piperazine-2,6-dione (Compound 141)

In a similar manner to Example 5, Compound 141 (155 mg, 49%) was obtained using (E)-4-[2-(1H-indazol-3-yl)vinyl]benzoic acid (200 mg, 0.76 mmol) obtained in Step 6 of Example 1, 1-(2-methoxyethyl)piperazine-2,6-dione (200 mg, 1.14 mmol), 1-hydroxybenzotriazole monohydrate (134 mg, 0.99 mmol), 1-ethyl-3-(3-dimethylaminopropyl)carbodiimide hydrochloride (204 mg, 1.06 mmol) and N-methylmorpholine (0.17 mL, 1.52 mmol).

$^1$H-NMR (270 MHz, DMSO-$d_6$) δ 3.23 (s, 3H), 3.41 (t, J=6.3 Hz, 2H), 3.84 (t, J=6.3 Hz, 2H), 4.51 (br, 4H), 7.23 (dd, J=7.1, 7.1 Hz, 1H), 7.41 (dd, J=8.1, 8.1 Hz, 1H), 7.49 (d, J=8.1 Hz, 2H), 7.56 (d, J=8.1 Hz, 1H), 7.58 (d, J=16.8 Hz, 1H), 7.69 (d, J=16.8 Hz, 1H), 7.84 (d, J=8.1 Hz, 2H), 8.22 (d, J=8.1 Hz, 1H), 13.2 (br, 1H). APCI-MS (m/z); 419 [M+H]$^+$

EXAMPLE 142

(E)-4-[(piperidin-4-yl)carbonyl]-1-{4-[2-(1H-indazol-3-yl)vinyl]benzoyl}piperazine dihydrochloride (Compound 142)

The product obtained using dihydrochloride of Compound 18 (200 mg, 0.49 mmol), isonipecotic acid tert-butyl ester (122 mg, 0.49 mmol), 1-hydroxybenzotriazole monohydrate (86 mg, 0.64 mmol), 1-ethyl-3-(3-dimethylaminopropyl)carbodiimide hydrochloride (132 mg, 0.69 mmol) and N-methylmorpholine (0.1 mL, 0.98 mmol) in a similar manner to Example 5, was dissolved in methanol (2.00 mL), and the solution was added with 4 moL/L hydrogen chloride-methanol solution (1.50 mL), followed by heating under reflux at 60° C. for 30 minutes. The reaction mixture was concentrated under reduced pressure, and the residue was crystallized from acetone to obtain Compound 142 (0.09 mg, 41%).

$^1$H-NMR (270 MHz, DMSO-$d_6$) δ 1.76 (br, 6H), 2.94 (br, 2H), 3.25-3.63 (m, 9H), 7.22 (dd, J=7.4, 7.4 Hz, 1H), 7.40 (dd, J=7.4, 7.4 Hz, 1H), 7.46 (d, J=8.2 Hz, 2H), 7.54 (d, J=8.2 Hz, 1H), 7.55 (d, J=16.8 Hz, 1H), 7.66 (d, J=16.8 Hz, 1H), 7.81 (d, J=8.2 Hz, 2H), 8.21 (d, J=8.2 Hz, 1H), 8.56 (br, 1H), 8.83 (br, 1H). ESI-MS (m/z); 444 [M+H]$^+$

EXAMPLE 143

(E)-4-[(1-methylpiperidin-4-yl)carbonyl]-1-{4-[2-(1H-indazol-3-yl)vinyl]benzoyl}piperazine (Compound 143)

In a similar manner to Example 5, Compound 143 (0.02 mg, 9%) was obtained using dihydrochloride of Compound 18 (200 mg, 0.49 mmol), 1-methylpiperidin-4-carboxylic acid (70 mg, 0.49 mmol), 1-hydroxybenzotriazole monohydrate (86 mg, 0.64 mmol), 1-ethyl-3-(3-dimethylaminopropyl)carbodiimide hydrochloride (132 mg, 0.69 mmol) and N-methylmorpholine (0.10 mL, 0.98 mmol).

$^1$H-NMR (270 MHz, DMSO-$d_6$) δ 1.58-1.59 (m, 4H), 1.91 (br, 2H), 2.15 (s, 3H), 2.76-2.80 (m, 2H), 3.51 (br, 9H), 7.22 (dd, J=7.7, 7.7 Hz, 1H), 7.39 (dd, J=7.7, 7.7 Hz, 1H), 7.45 (d, J=8.4 Hz, 2H), 7.53 (d, J=8.4 Hz, 1H), 7.55 (d, J=16.6 Hz, 1H), 7.65 (d, J=16.6 Hz, 1H), 7.80 (d, J=8.4 Hz, 2H), 8.21 (d, J=8.4 Hz, 1H), 13.2 (br, 1H). ESI-MS (m/z); 458 [M+H]$^+$

EXAMPLE 144

(E)-4-[N,N-di(2-hydroxyethyl)aminoacetyl]-1-{4-[2-(1H-indazol-3-yl)vinyl]benzoyl}piperazine dihydrochloride (Compound 144)

The crude product obtained using dihydrochloride of Compound 18 (150 mg, 0.370 mmol) N-methylmorpholine (0.0812 mL, 0.740 mmol), 1-ethyl-3-(3-dimethylaminopropyl)carbodiimide hydrochloride (99.3 mg, 0.370 mmol), 1-hydroxybenzotriazole monohydrate (64.9 mg, 0.481 mmol) and di(hydroxyethyl)aminoacetic acid (60.4 mg, 0.370 mmol) in a similar manner to Example 5, was purified by C-18 column chromatography (water/methanol=67/33), followed by treating with 10% hydrogen chloride-methanol solution (0.775 mL) and triturating in ethyl acetate to obtain Compound 144 (43.5 mg, 21%).

$^1$H-NMR (270 MHz, DMSO-$d_6$) δ 2.72-7.76 (brm, 2H), 3.20-3.25 (brm, 4H), 3.22-3.26 (brm, 4H), 3.60-3.80 (br, 8H), 7.21 (t, J=8.1 Hz, 1H), 7.40 (d, J=8.1 Hz, 1H), 7.49 (d, J=7.8 Hz, 2H), 7.54 (d, J=18.6 Hz, 1H), 7.56 (d, J=9.4 Hz, 1H), 7.65 (d, J=18.6 Hz, 1H), 7.80 (d, J=7.8 Hz, 2H), 8.20 (d, J=9.4 Hz, 1H), 8.94 (brs, 1H). ESI-MS (m/z); 417 [M−$C_2H_4O_2$]$^+$

EXAMPLE 145

(E)-4-[(1-methylpyrrolidin-2-yl)carbonyl]-1-{4-[2-(1H-indazol-3-yl)vinyl]benzoyl}piperazine (Compound 145)

In a similar manner to Step 1 of Example 1, Compound 145 (97 mg, 87%) was obtained using Compound 18 (83 mg, 0.25 mmol), N-methylproline monohydrate (44 mg, 0.30 mmol), 1-hydroxybenzotriazole monohydrate (110 mg, 0.83 mmol), 1-ethyl-3-(3-dimethylaminopropyl)carbodiimide hydrochloride (160 mg, 0.85 mmol) and N-methylmorpholine (0.12 mL, 1.10 mmol).

$^1$H-NMR (270 MHz, CDCl$_3$) δ 1.75-2.31 (m, 6H), 2.38 (s, 3H), 3.16-3.22 (m, 1H), 3.30-4.00 (m, 8H), 7.21-7.28 (m, 1H), 7.36-7.42 (m, 1H), 7.43 (d, J=8.3 Hz, 2H), 7.50-7.52 (m, 3H), 7.61 (d, J=8.3 Hz, 2H), 8.02 (d, J=8.2 Hz, 2H). APCI-MS (m/z); 444 [M+H]$^+$

EXAMPLE 146

(E)-4-[(4-methylmorpholin-2-yl)carbonyl]-1-{4-[2-(1H-indazol-3-yl)vinyl]benzoyl}piperazine (Compound 146)

In a similar manner to Step 1 of Example 1, Compound 146 (60 mg, 52%) was obtained using Compound 18 (100 mg, 0.25 mmol), 4-methylmorpholine-2-carboxylic acid hydrochloride (56 mg, 0.30 mmol), 1-hydroxybenzotriazole monohydrate (96 mg, 0.40 mmol), 1-ethyl-3-(3-dimethylaminopropyl)carbodiimide hydrochloride (82 mg, 0.43 mmol) and N-methylmorpholine (0.16 mL, 1.4 mmol).

$^1$H-NMR (270 MHz, CDCl$_3$) δ 2.17-2.27 (m, 1H), 2.35-2.44 (m, 4H), 2.67 (brd, J=11.4 Hz, 1H), 2.90 (brd, J=11.8 Hz, 1H), 3.30-4.00 (m, 10H), 4.25-4.28 (m, 1H), 7.21-7.28 (m, 1H), 7.36-7.51 (m, 6H), 7.60 (d, J=8.2 Hz, 2H), 8.02 (d, J=8.2 Hz, 1H). APCI-MS (m/z); 460 [M+H]$^+$

EXAMPLE 147

(E)-4-Hydroxy-1-{4-[2-(1H-indazol-3-yl)vinyl]benzoyl}piperazine (Compound 147)

Compound 18 (0.35 g, 1.1 mmol) was dissolved in methanol (2.1 mL) and was added with a 31% hydrogen peroxide solution (0.13 g, 1.1 mmol), followed by stirring at room temperature for 1 hour. The reaction mixture was added with sodium hydrogen sulfite (0.1 g, 0.96 mmol), and then the deposited crystals were removed by filtration after confirming the disappearance of hydrogen peroxide using a potassium iodide-starch paper. The solvent of the filtrate was evaporated under reduced pressure, the crude product was purified by preparative silica gel chromatography [aminomodified chemically bound silica gel Chromatorex (registered trademark) NH, Fuji Silysia Chemical Ltd., methanol/chloroform=1/9] to obtain Compound 147 (57 mg, 15%).

$^1$H-NMR (270 MHz, DMSO-$d_6$) δ 2.44-2.52 (m, 4H), 2.95-3.29 (brm, 4H), 7.28 (brt, J=7.5 Hz, 1H), 7.44-7.50 (m, 3H), 7.60 (d, J=16.7 Hz, 1H), 7.61-7.63 (m, 1H), 7.70 (d, J=16.7 Hz, 1H), 7.84 (d, J=8.4 Hz, 2H), 8.27 (d, J=8.2 Hz, 1H), 8.30 (s, 1H), 13.1-13.4 (m, 1H). APCI-MS (m/z); 349 [M+H]$^+$

EXAMPLE 148

(E)-1-{4-+[2-(1H-indazol-3-yl)vinyl]benzoyl}-4-(tert-butyloxycarbonylamino)piperazine (Compound 148)

In a similar manner to Step 1 of Example 1, Compound 148 (97 mg, 87%) was obtained using (E)-4-[2-(1H-indazol-3-yl)vinyl]benzoic acid (66 mg, 0.25 mmol) obtained in Step 6 of Example 1, 1-(tert-butyloxycarbonylamino)piperazine (60 mg, 0.30 mmol) obtained in a similar manner to the method described in WO98/35951, 1-hydroxybenzotriazole monohydrate (44 mg, 0.32 mmol), 1-ethyl-3-(3-dimethylaminopropyl)carbodiimide hydrochloride (71 mg, 0.35 mmol) and N-methylmorpholine (55 µL, 0.50 mmol).

$^1$H-NMR (270 MHz, DMSO-$d_6$) δ 1.39 (s, 9H), 2.66-2.82 (m, 4H), 3.30-3.72 (m, 4H), 7.22 (brt, J=7.2 Hz, 1H), 7.38-7.43 (m, 3H), 7.54 (d, J=16.8 Hz, 1H), 7.56 (d, J=7.4 Hz, 1H), 7.64 (d, J=16.8 Hz, 1H), 7.79 (d, J=8.2 Hz, 2H), 8.20 (d, J=8.1 Hz, 1H), 13.2 (brs, 1H). APCI-MS (m/z); 448 [M+H]$^+$

EXAMPLE 149

(E)-1-{4-[2-(1H-indazol-3-yl)vinyl]benzoyl}-4-aminopiperazine (Compound 149)

In a similar manner to Example 18, Compound 149 (28 mg, 42%) was obtained using Compound 148 (85 mg, 0.19 mmol), methanol (0.19 mL) and 10% hydrogen chloride-methanol solution (0.38 mL).

$^1$H-NMR (300 MHz, CDCl$_3$) δ 2.46-2.82 (m, 4H), 3.40-4.00 (m, 4H), 7.22-7.27 (m, 1H), 7.37-7.48 (m, 4H), 7.51 (s, 2H), 7.59 (brd, J=8.1 Hz, 2H), 8.02 (d, J=8.1 Hz, 1H), 10.8-12.0 (m, 1H). APCI-MS (m/z); 348 [M+H]$^+$

EXAMPLE 150

(E)-1-{4-[2-(1H-indazol-3-yl)vinyl]benzoyl}-4-(morpholinocarbonylamino)piperazine (Compound 150)

In a similar manner to Step 1 of Example 1, Compound 150 (87 mg, 74%) was obtained using (E)-4-[2-(1H-indazol-3-yl)vinyl]benzoic acid (68 mg, 0.26 mmol) obtained in Step 6 of Example 1, 1-morpholinocarbonylaminopiperazine (65 mg, 0.30 mmol), 1-hydroxybenzotriazole monohydrate (46 mg, 0.33 mmol), 1-ethyl-3-(3-dimethylaminopropyl)carbodiimide hydrochloride (68 mg, 0.35 mmol) and N-methylmorpholine (56 µL, 0.51 mmol).

$^1$H-NMR (270 MHz, CD$_3$OD) δ 2.69-2.95 (m, 4H), 3.35-3.39 (m, 4H), 3.62-3.86 (m, 8H), 7.22-7.28 (m, 1H), 7.40-7.47 (m, 3H), 7.53-7.57 (m, 3H), 7.75 (brd, J=8.3 Hz, 2H), 8.12 (d, J=8.3 Hz, 1H). APCI-MS (m/z); 461 [M+H]$^+$

EXAMPLE 151

(E)-3-amino-4-{[4-(2-(1H-indazol-3-yl)vinyl)benzoyl]piperazin-1-yl}-3-cyclobutene-1,2-dione (Compound 151)

Step 1

(E)-1-{4-[2-(1H-indazol-3-yl)vinyl]benzoyl}piperazine (1.0 g, 2.5 mmol) obtained in Example 18 was dissolved in methanol (9.9 mL), and the solution was added with 3,4-diisopropoxy-3-cyclobutene-1,2-dione (0.69 g, 3.5 mmol) and triethylamine (0.69 mL, 4.9 mmol), followed by stirring at room temperature for 13 hours. The reaction mixture was concentrated under reduced pressure, and the crude product was added with ethanol, followed by stirring. The deposited crystal was collected by filtration to obtain (E)-3-{4-[4-(2-(1H-indazol-3-yl)vinyl)benzoyl]piperazin-1-yl}-4-isopropoxy-3-cyclobutene-1,2-dione (0.94 g, 81%).

Step 2

(E)-3-{4-[4-(2-(1H-indazol-3-yl)vinyl)benzoyl]piperazin-1-yl}-4-isopropoxy-3-cyclobutene-1,2-dione (87 mg, 0.19 mmol) obtained in Step 1 was dissolved in methanol (0.74 mL) and DMF (0.5 mL), and the solution was added with ammonium chloride (100 mg, 1.9 mmol) and triethylamine (0.26 mL, 1.9 mmol), followed by stirring, at 50° C. for 4 hours. The reaction was stopped by addition of saturated aqueous sodium hydrogencarbonate solution, and the reaction mixture was extracted with chloroform (100 mL×2). The organic layer was washed with saturated brine, and was dried over anhydrous sodium sulfate, and then the solvent was evaporated under reduced pressure. The crude product was crystallized from methanol (5 mL) to obtain Compound 151 (16.3 mg, 21%).

$^1$H-NMR (270 MHz, DMSO-$d_6$) δ 3.45-3.90 (m, 8H), 7.22 (brt, J=7.5 Hz, 1H), 7.41 (brt, J=7.2 Hz, 1H), 7.47 (d, J=8.3 Hz, 2H), 7.55 (d, J=16.7 Hz, 1H), 7.57 (d, J=10.0 Hz, 1H), 7.66 (d, J=16.7 Hz, 1H), 7.75 (br s, 2H), 7.81 (d, J=8.3 Hz, 2H), 8.21 (d, J=8.1 Hz, 1H), 13.2 (brs, 1H). APCI-MS (m/z); 426 [M–H]$^-$

EXAMPLE 152

(E)-3-methylamino-4-{[4-(2-(1H-indazol-3-yl)vinyl)benzoyl]piperazin-1-yl}-3-cyclobutene-1,2-dione (Compound 152)

In a similar manner to Step 2 of Example 151, Compound 152 (112 mg, 100%) was obtained using (E)-3-{4-[4-(2-(1H-indazol-3-yl)vinyl)benzoyl]piperazin-1-yl}-4-isopropoxy-3-cyclobutene-1,2-dione (120 mg, 0.25 mmol) obtained in Step 1 of Example 151, 40% methylamine-methanol solution (0.16 mL, 1.9 mmol) and DMF (0.99 mL).

$^1$H-NMR (270 MHz, DMSO-$d_6$) δ 3.18 (s, 3H), 3.50-3.82 (m, 8H), 7.19-7.24 (m, 1H), 7.37-7.43 (m, 1H), 7.47 (d, J=8.2 Hz, 2H), 7.55 (d, J=16.9 Hz, 1H), 7.56 (d, J=6.7 Hz, 1H), 7.66 (d, J=16.9 Hz, 1H), 7.80 (d, J=8.2 Hz, 2H), 8.21 (d, J=8.2 Hz, 1H). APCI-MS (m/z); 442 [M+H]$^+$

EXAMPLE 153

(E)-3-dimethylamino-4-{[4-(2-(1H-indazol-3-yl)vinyl)benzoyl]piperazin-1-yl}-3-cyclobutene-1,2-dione (Compound 153)

In a similar manner to Step 2 of Example 151, Compound 153 (94 mg, 87%) was obtained using (E)-3-{4-[4-(2-(1H-indazol-3-yl)vinyl)benzoyl]piperazin-1-yl}-4-isopropoxy-3-cyclobutene-1,2-dione (110 mg, 0.24 mmol) obtained in Step 1 of Example 151, 2.0 mol/L dimethylamine-methanol solution (0.90 mL, 1.8 mmol) and DMF (0.95 mL).

$^1$H-NMR (270 MHz, DMSO-$d_6$) δ 3.17 (s, 6H), 3.48-3.85 (m, 8H), 7.20-7.25 (m, 1H), 7.38-7.44 (m, 1H), 7.47 (d, J=8.2 Hz, 2H), 7.55 (d, J=16.6 Hz, 1H), 7.57 (d, J=9.7 Hz, 1H), 7.66 (d, J=16.6 Hz, 1H), 7.81 (d, J=8.2 Hz, 2H), 8.21 (d, J=8.1 Hz, 1H), 13.2 (brs, 1H). APCI-MS (m/z); 456 [M+H]$^+$

EXAMPLE 154

(E)-3-(pyrrolidin-1-yl)-4-{[4-(2-(1H-indazol-3-yl)vinyl)benzoyl]piperazin-1-yl}-3-cyclobutene-1,2-dione (Compound 154)

In a similar manner to Step 2 of Example 151, Compound 154 (97 mg, 93%) was obtained using (E)-3-{4-[4-(2-(1H-indazol-3-yl)vinyl)benzoyl]piperazin-1-yl}-4-isopropoxy- 3-cyclobutene-1,2-dione (100 mg, 0.22 mmol) obtained in Step 1 of Example 151, pyrrolidine (0.14 mL, 1.6 mmol) and DMF (0.86 mL).

$^1$H-NMR (270 MHz, DMSO-$d_6$) δ 1.84-1.89 (m, 4H), 3.49-3.91 (m, 12H), 7.19-7.25 (m, 1H), 7.38-7.43 (m, 1H), 7.47 (d, J=8.2 Hz, 2H), 7.55 (d, J=16.7 Hz, 1H), 7.57 (d, J=9.9 Hz, 1H), 7.66 (d, J=16.7 Hz, 1H), 7.81 (d, J=8.2 Hz, 2H), 8.21 (d, J=8.1 Hz, 1H), 13.2 (brs, 1H). APCI-MS (m/z); 482 [M+H]$^+$

EXAMPLE 155

(E)-3-piperidino-4-{[4-(2-(1H-indazol-3-yl)vinyl) benzoyl]piperazin-1-yl}-3-cyclobutene-1,2-dione (Compound 155)

In a similar manner to Step 2 of Example 151, Compound 155 (93 mg, 87%) was obtained using (E)-3-{4-[4-(2-(1H-indazol-3-yl)vinyl)benzoyl]piperazin-1-yl}-4-isopropoxy-3-cyclobutene-1,2-dione (100 mg, 0.22 mmol) obtained in Step 1 of Example 151, piperidine (0.16 mL, 1.6 mmol) and DMF (0.86 mL).

$^1$H-NMR (270 MHz, DMSO-$d_6$) δ 1.57-1.65 (m, 6H), 3.47-3.85 (m, 12H), 7.20-7.25 (m, 1H), 7.38-7.43 (m, 1H), 7.47 (d, J=8.2 Hz, 2H), 7.55 (d, J=16.7 Hz, 1H), 7.57 (d, J=9.7 Hz, 1H), 7.66 (d, J=16.7 Hz, 1H), 7.81 (d, J=8.2 Hz, 2H), 8.21 (d, J=8.2 Hz, 1H), 13.2 (brs, 1H). APCI-MS (m/z); 496 [M+H]$^+$

EXAMPLE 156

(E)-3-morpholino-4-{[4-(2-(1H-indazol-3-yl)vinyl) benzoyl]piperazin-1-yl}-3-cyclobutene-1,2-dione (Compound 156)

In a similar manner to Step 2 of Example 151, Compound 156 (79 mg, 74%) was obtained using (E)-3-{4-[4-(2-(1H-indazol-3-yl)vinyl)benzoyl]piperazin-1-yl}-4-isopropoxy-3-cyclobutene-1,2-dione (100 mg, 0.21 mmol) obtained in Step 1 of Example 151, morpholine (0.14 mL, 1.6 mmol) and DMF (0.86 mL).

$^1$H-NMR (270 MHz, DMSO-$d_6$) δ 3.57-3.83 (m, 16H), 7.19-7.25 (m, 1H), 7.37-7.43 (m, 1H), 7.46 (d, J=8.2 Hz, 2H), 7.55 (d, J=16.7 Hz, 1H), 7.57 (d, J=8.2 Hz, 1H), 7.66 (d, J=16.7 Hz, 1H), 7.81 (d, J=8.2 Hz, 2H), 8.21 (d, J=8.2 Hz, 1H). APCI-MS (m/z); 498 [M+H]$^+$

EXAMPLE 157

(E)-3-(4-methylpiperazin-1-yl)-4-{[4-(2-(1H-indazol-3-yl)vinyl)benzoyl]piperazin-1-yl}-3-cyclobutene-1,2-dione (Compound 157)

In a similar manner to Step 2 of Example 151, Compound 157 (49 mg, 45%) was obtained using (E)-3-{4-[4-(2-(1H-indazol-3-yl)vinyl)benzoyl]piperazin-1-yl}-4-isopropoxy-3-cyclobutene-1,2-dione (100 mg, 0.21 mmol) obtained in Step 1 of Example 151 and N-methylpiperazine (0.18 mL, 1.6 mmol) and DMF (0.86 mL).

$^1$H-NMR (270 MHz, DMSO-$d_6$) δ 2.20 (s, 3H), 2.38-2.42 (m, 4H), 3.52-3.82 (m, 12H), 7.19-7.25 (m, 1H), 7.37-7.43 (m, 1H), 7.46 (d, J=8.1 Hz, 2H), 7.55 (d, J=16.9 Hz, 1H), 7.57 (d, J=8.1 Hz, 1H), 7.66 (d, J=16.9 Hz, 1H), 7.81 (d, J=8.1 Hz, 2H), 8.21 (d, J=8.2 Hz, 1H). APCI-MS (m/z); 511 [M+H]$^+$

EXAMPLE 158

(R)-(E)-1-{4-[2-(1H-Indazol-3-yl)vinyl]benzoyl}-3-aminopyrrolidine (Compound 158)

The product obtained using (E)-4-[2-(1H-indazol-3-yl)vinyl]benzoic acid (700 mg, 2.65 mmol) obtained in Step 6 of Example 1, tert-butyl (R)-(pyrrolidin-3-yl)carbamate (740 mg, 3.98 mmol), 1-hydroxybenzotriazole monohydrate (470 mg, 3.46 mmol), 1-ethyl-3-(3-dimethylaminopropyl)carbodiimide hydrochloride (710 mg, 3.72 mmol) and N-methylmorpholine (0.608 mL, 5.32 mmol) in a similar manner to Example 5, was dissolved in methanol (1.5 mL), and the solution was added with a 4 mol/L solution of hydrogen chloride in methanol (1.50 mL), followed by heating under reflux at 60° C. for 60 minutes. The reaction mixture was concentrated under reduced pressure, the residue was added with saturated aqueous potassium carbonate solution and ethyl acetate and was extracted. The crude product was crystallized from ethyl acetate to obtain Compound 158 (506 mg, 58%).

$^1$H-NMR (270 MHz, DMSO-$d_6$) δ 1.59-1.99 (m, 4H), 3.08-3.18 (m, 1H), 3.67-3.78 (m, 4H), 7.22 (dd, J=7.6, 7.6 Hz, 1H), 7.40 (dd, J=7.6, 7.6 Hz, 1H), 7.51-7.57 (m, 4H), 7.64 (d, J=16.8 Hz, 1H), 7.77 (d, J=8.2 Hz, 2H), 8.21 (d, J=8.2 Hz, 1H), 13.2 (brs, 1H). APCI-MS (m/z); 333 [M+H]$^+$

EXAMPLE 159

(S)-(E)-1-{4-[2-(1H-indazol-3-yl)vinyl]benzoyl}-3-aminopyrrolidine (Compound 159)

The product obtained using (E)-4-[2-(1H-indazol-3-yl)vinyl]benzoic acid (700 mg, 2.65 mmol) obtained in Step 6 of Example 1, (S)-(pyrrolidin-3-yl)carbamic acid tert-butyl ester (740 g, 3.98 mmol), 1-hydroxybenzotriazole monohydrate (470 mg, 3.46 mmol), 1-ethyl-3-(3-dimethylaminopropyl)carbodiimide hydrochloride (710 mg, 3.72 mmol) and N-methylmorpholine (0.608 mL, 5.32 mmol) in a similar manner to Example 5, was dissolved in methanol (1.5 mL) and the solution was added with 4 moL/L hydrogen chloride-methanol solution (1.50 mL), followed by heating under reflux at 60° C. for 60 minutes. The reaction mixture was concentrated under reduced pressure, and the residue was added with saturated aqueous sodium hydrogencarbonate solution and ethyl acetate, followed by extraction. The crude product was crystallized from acetone to obtain Compound 159 (190 mg, 22%).

$^1$H-NMR (270 MHz, DMSO-$d_6$) δ 1.59-1.99 (m, 4H), 3.08-3.18 (m, 1H), 3.67-3.78 (m, 4H), 7.22 (dd, J=7.6, 7.6 Hz, 1H), 7.40 (dd, J=7.6, 7.6 Hz, 1H), 7.51-7.57 (m, 4H), 7.64 (d, J=16.8 Hz, 1H), 7.77 (d, J=8.2 Hz, 2H), 8.21 (d, J=8.2 Hz, 1H), 13.2 (brs, 1H).

APCI-MS (m/z); 333 [M+H]$^+$

EXAMPLE 160

Preparation Example (Tablet)

Tablet having the following formulation is prepared in a conventional manner.

| | |
|---|---|
| Compound 2 | 5 mg |
| Lactose | 60 mg |
| Potato starch | 30 mg |
| Poly(vinyl alcohol) | 2 mg |
| Magnesium stearate | 1 mg |
| Tar pigment | trace amount |

INDUSTRIAL APPLICABILITY

The present invention provides indazole derivatives or pharmaceutically acceptable salts thereof which have antitumor activities or the like.

The invention claimed is:

1. An indazole derivative represented by Formula (I)

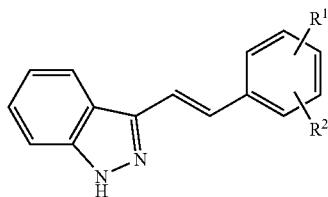

(I)

wherein $R^1$ represents $CONR^{1a}R^{1b}$ (wherein $R^{1a}$ and $R^{1b}$ may be the same or different and each represents a hydrogen atom, substituted or unsubstituted lower alkyl, substituted or unsubstituted aryl, substituted or unsubstituted aralkyl, or a substituted or unsubstituted heterocyclic group, or $R^{1a}$ and $R^{1b}$ are combined together with the adjacent nitrogen atom thereto to form a substituted or unsubstituted heterocyclic group) or $NR^{1c}R^{1d}$ (wherein $R^{1c}$ represents substituted or unsubstituted lower alkylsulfonyl or substituted or unsubstituted arylsulfonyl and $R^{1d}$ represents a hydrogen atom or substituted or unsubstituted lower alkyl); and $R^2$ represents a hydrogen atom, halogen, cyano, nitro, hydroxy, carboxy, lower alkoxycarbonyl, substituted or unsubstituted lower alkyl, substituted or unsubstituted lower alkoxy, substituted or unsubstituted lower alkanoyl, $CONR^{2a}R^{2b}$ (wherein $R^{2a}$ and $R^{2b}$ may be the same or different and each represents a hydrogen atom, substituted or unsubstituted lower alkyl, substituted or unsubstituted aryl, substituted or unsubstituted aralkyl or a substituted or unsubstituted heterocyclic group, or $R^{2a}$ and $R^{2b}$ are combined together with the adjacent nitrogen atom thereto to form a substituted or unsubstituted heterocyclic group) or $NR^{2c}R^{2d}$ (wherein $R^{2c}$ and $R^{2d}$ may be the same or different and each represents a hydrogen atom, substituted or unsubstituted lower alkyl, substituted or unsubstituted lower alkanoyl, substituted or unsubstituted aroyl, substituted or unsubstituted heteroaroyl, substituted or unsubstituted aralkyl, substituted or unsubstituted lower alkylsulfonyl or substituted or unsubstituted arylsulfonyl), or a pharmaceutically acceptable salt thereof.

2. The indazole derivative or the pharmaceutically acceptable salt thereof according to claim 1, wherein $R^1$ is $CONR^{1a}R^{1b}$ and $R^2$ is a hydrogen atom or substituted or unsubstituted lower alkoxy.

3. The indazole derivative or the pharmaceutically acceptable salt thereof according to claim 1, wherein $R^1$ is $NR^{1c}R^{1d}$ and $R^2$ is substituted or unsubstituted lower alkoxy.

4. The indazole derivative or the pharmaceutically acceptable salt thereof according to claim 1, wherein $R^1$ is $CONR^{1a}R^{1b}$ and $R^2$ is halogen or substituted or unsubstituted lower alkyl.

5. The indazole derivative or the pharmaceutically acceptable salt thereof according to claim 1, wherein $R^1$ is $NR^{1c}R^{1d}$ and $R^2$ is a hydrogen atom.

6. An indazole derivative represented by Formula (IA)

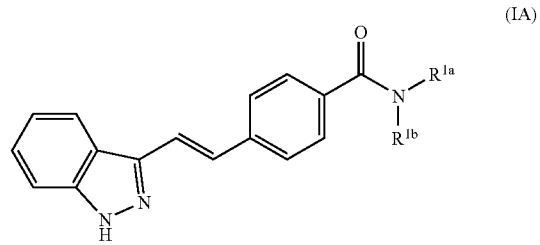

(IA)

wherein $R^{1a}$ and $R^{1b}$ may be the same or different and each represents a hydrogen atom, substituted or unsubstituted lower alkyl, substituted or unsubstituted aryl, substituted or unsubstituted aralkyl, or a substituted or unsubstituted heterocyclic group, or $R^{1a}$ and $R^{1b}$ are combined together with the adjacent nitrogen atom thereto to form a substituted or unsubstituted heterocyclic group, or a pharmaceutically acceptable salt thereof.

7. The indazole derivative or the pharmaceutically acceptable salt thereof according to claim 6, wherein $R^{1a}$ and $R^{1b}$ are combined together with the adjacent nitrogen atom thereto to form a substituted or unsubstituted heterocyclic group.

8. The indazole derivative or the pharmaceutically acceptable salt thereof according to claim 6, wherein $R^{1a}$ and $R^{1b}$ are combined together with the adjacent nitrogen atom thereto to form a substituted or unsubstituted piperazinyl.

9. (E)-1-{4-[2-(1H-indazol-3-yl)vinyl]benzoyl}piperazine or a pharmaceutically acceptable salt thereof.

10. (E)-4-{4-[2-(1H-indazol-3-yl)vinyl]benzoyl}piperazine-2-one or a pharmaceutically acceptable salt thereof.

11. (E)-1-{4-[2-(1H-indazol-3-yl)vinyl]benzoyl}-3-aminopyrrolidine or a pharmaceutically acceptable salt thereof.

12. The indazole derivative or the pharmaceutically acceptable salt thereof according to claim 1, wherein $R^1$ is $CONR^{1a}R^{1b}$, and $R^{1a}$ and $R^{1b}$ are combined together with the adjacent nitrogen atom thereto to form a substituted or unsubstituted heterocyclic group.

13. The indazole derivative or the pharmaceutically acceptable salt thereof according to claim 2, wherein $R^{1a}$ and $R^{1b}$ are combined together with the adjacent nitrogen atom thereto to form a substituted or unsubstituted heterocyclic group.

14. The indazole derivative or the pharmaceutically acceptable salt thereof according to claim 4, wherein $R^{1a}$ and $R^{1b}$ are combined together with the adjacent nitrogen atom thereto to form a substituted or unsubstituted heterocyclic group.

15. A pharmaceutical composition which comprises, as an active ingredient, the indazole derivative or the pharmaceutically acceptable salt thereof according to any of claims 1-5 or 6-14 together with a pharmaceutically acceptable carrier.

* * * * *

UNITED STATES PATENT AND TRADEMARK OFFICE
CERTIFICATE OF CORRECTION

PATENT NO. : 7,470,717 B2
APPLICATION NO. : 10/548475
DATED : December 30, 2008
INVENTOR(S) : Yoshihisa Ohta et al.

It is certified that error appears in the above--identified patent and that said Letters Patent is hereby corrected as shown below:

ON THE TITLE PAGE [56] REFERENCES CITED:

Foreign Patent Documents,
        "JP 32059 2/1990" should read --JP 2-32059 2/1990--.

ON THE TITLE PAGE [57] ABSTRACT:

Line 6, "ararkyl" should read --aralkyl--;
    Line 15, "ararkyl" should read --aralkyl--; and
    Line 23, "ararkyl," should read --aralkyl,--.

COLUMN 1:

Line 20, "mula (II)" should read --mula (II):--.

COLUMN 2:

Line 2, "formula (III)" should read --formula (III):--;
    Line 27, "mula (IV)" should read --mula (IV):--; and
    Line 45, "formula (V)" should read --formula (V):--.

COLUMN 3:

Line 1, "following" should read --the following--; and
    Line 2, "formula (I)" should read --formula (I):--.

COLUMN 5:

Line 30, "se c-butyl," should read --sec-butyl,--.

COLUMN 6:

Line 23, "tetrahydroquinoxalinyll" should read --tetrahydroquinoxalinyl,--; and
    Line 45, "include" should read --include:--.

COLUMN 7:

Line 26, "meaning (viii)" should read --meaning as (viii)--;
    Line 28, "ardyl," should read --aroyl,--; and
    Line 32, "include" should read --include:--.

COLUMN 9:

Line 4, "atom)" should read --atom).--;
Line 58, "each groups" should read --each of the groups--;
Line 59, "each groups" should read --each of the groups--; and
Line 65, "group" should read --groups--.

COLUMN 10:

Line 35, "each atoms" should read --each of the atoms--;
Line 37, "respectively)" should read --respectively).--;
Line 52, "have" should read --has--;
Line 54, "have other" should read --has another--; and
Line 57, "(kokai)" should read --(Kokai)--.

COLUMN 11:

Line 22, "(wherein" should read --(Wherein--;
Line 26, "to 2-5)" should read --to 2-5.)--;
Line 30, "carboxy)" should read --carboxy.)--;
Line 42, "amino)" should read --amino.)--; and
Line 67, "tively)]" should read --tively).]--.

COLUMN 12:

Line 10, "oxide.trifluo-" should read --oxide•trifluo- --;
Line 25, "aryl)]" should read --aryl).]--; and
Line 50, "above]" should read --above.]--.

COLUMN 13:

Line 5, "be use" should read --be used--.

COLUMN 14:

Line 3, "it is, where" should read --it is; where--.

COLUMN 41:

Line 59, "Test" should be deleted; and
Line 60, "Example:" should read --Test Example:--.

COLUMN 43:

Line 38, "Each-20" should read --Each 20--.

COLUMN 46:

Line 65, "solution-was" should read --solution was--.

COLUMN 49:

Line 53, "pressure. the" should read --pressure. The--.

COLUMN 51:

Line 32, "(300-MHz," should read --300 MHz,--.

COLUMN 54:

Line 1, "(m,.3H)," should read --(m, 3H),--.

COLUMN 58:

Line 26, "benzoic-acid" should read --benzoic acid--.

COLUMN 65:

Line 21, "(1H-indazol73-yl)" should read --(1H-indazol-3-yl)--.

COLUMN 66:

Line 24, "vinyl-]" should read --vinyl]--.

COLUMN 70:

Line 2, "(d, 7.9 Hz," should read --(d, J=7.9 Hz,--.

COLUMN 71:

Line 38, "and-the solution" should read --and the solution--.

COLUMN 74:

Line 40, "Example 5 Compound" should read --Example 5. Compound--.

COLUMN 75:

Line 21, "piperadin-2-one" should read --piperazin-2-one--; and
    Line 26, "piperadin-2-one" should read --piperazin-2-one--.

COLUMN 80:

Line 42, "1.40 mmol)-and" should read --1.40 mmol) and--.

COLUMN 82:

Line 19, "triphenylphosponioum" should read --triplenylphosphonium--.

COLUMN 90:

Line 34, "1H) 13.2" should read --1H), 13.2--.

COLUMN 91:

Line 3, "and-N-isopropyl-2-" should read --and N-isopropyl-2- --; and
    Line 67, "mmol) In a" should read --mmol) in a--.

COLUMN 95:

Line 2, "(E)-1-{4+[2-" should read --(E)-1-{4-[2- --.

COLUMN 96:

Line 9, "stirring," should read --stirring--.

COLUMN 99:

Line 18, "Formula (I)" should read --Formula (I):--.

COLUMN 100:

Line 11, "Formula (II)" should read --Formula (II):--;
Line 44, "piperazine-2-one" should read --piperazin-2-one--;
Line 63, "claims 1-5 or" should read --claims 1-14--; and
Line 64, "6-14" should be deleted.

Signed and Sealed this

Fifth Day of January, 2010

David J. Kappos
*Director of the United States Patent and Trademark Office*

UNITED STATES PATENT AND TRADEMARK OFFICE
CERTIFICATE OF CORRECTION

PATENT NO.          : 7,470,717 B2                                    Page 1 of 1
APPLICATION NO.  : 10/548475
DATED                  : December 30, 2008
INVENTOR(S)        : Yoshihisa Ohta et al.

It is certified that error appears in the above-identified patent and that said Letters Patent is hereby corrected as shown below:

COLUMN 74:

Line 40, "Example 5. Compound" should read --Example 5, Compound--.

COLUMN 100:

Line 11, "Formula (1A)" should read --Formula (IA):--.

Signed and Sealed this

Eighteenth Day of May, 2010

David J. Kappos
*Director of the United States Patent and Trademark Office*